(12) United States Patent
Roeder et al.

(10) Patent No.: US 9,101,455 B2
(45) Date of Patent: Aug. 11, 2015

(54) PRELOADED WIRE FOR ENDOLUMINAL DEVICE

(71) Applicant: Cook Medical Technologies LLC, Bloomington, IN (US)

(72) Inventors: Blayne A. Roeder, Bloomington, IN (US); Matthew S. Huser, West Lafayette, IN (US); Kelly Coverdale, Holland Park (AU)

(73) Assignee: Cook Medical Technologies LLC, Bloomington, IN (US)

( * ) Notice: Subject to any disclaimer, the term of this patent is extended or adjusted under 35 U.S.C. 154(b) by 414 days.

(21) Appl. No.: 13/718,915

(22) Filed: Dec. 18, 2012

(65) Prior Publication Data

US 2013/0123907 A1    May 16, 2013

Related U.S. Application Data

(63) Continuation-in-part of application No. 13/208,793, filed on Aug. 12, 2011.

(60) Provisional application No. 61/373,610, filed on Aug. 13, 2010, provisional application No. 61/579,027, filed on Dec. 22, 2011.

(51) Int. Cl.
*A61F 2/06* (2013.01)
*A61F 2/954* (2013.01)
(Continued)

(52) U.S. Cl.
CPC . *A61F 2/06* (2013.01); *A61F 2/954* (2013.01); *A61F 2/966* (2013.01); *A61M 25/09* (2013.01);
(Continued)

(58) Field of Classification Search
CPC .............. A61F 2/06; A61F 2/07; A61F 2/95; A61F 2/954; A61F 2/966; A61F 2002/061; A61F 2002/072; A61F 2002/075; A61F 2002/077; A61F 2002/9511; A61F 2002/9665
USPC ................ 606/108, 191–200; 623/1.11–1.13, 623/1.16, 1.23, 1.35
See application file for complete search history.

(56) References Cited

U.S. PATENT DOCUMENTS

| | | | |
|---|---|---|---|
| 4,502,159 | A | 3/1985 | Woodroof et al. |
| 4,675,361 | A | 6/1987 | Ward, Jr. |

(Continued)

FOREIGN PATENT DOCUMENTS

| | | |
|---|---|---|
| EP | 2 417 942 A1 | 2/2012 |
| EP | 2 517 671 A2 | 10/2012 |

(Continued)

OTHER PUBLICATIONS

"Simplified Method of Introducing Double-J Stent Catheters Using a Coaxial Sheath System," Mercado et al., http://www.ajronline.org/doi/pdf/10.2214/ajr.145.6.1271, American Roentgen Ray Society; Dec. 1985 (pp. 1271-1273).

(Continued)

*Primary Examiner* — David Eastwood
(74) *Attorney, Agent, or Firm* — Brinks Gilson & Lione

(57) ABSTRACT

A system may include an endoluminal prosthesis and a guide wire. The prosthesis may include a tubular body including a graft material wall, a proximal end opening, a distal end opening, and a lumen extending longitudinally therein. The prosthesis may include first and second fenestrations in the graft material wall. The first and second fenestrations may be spaced from one another circumferentially about the tubular body. The guide wire may have a first end and a second end both extending from a region proximal of the proximal end opening. The guide wire may enter the proximal end opening, exit the first fenestration, partially traverse an exterior surface of the prosthesis, enter the second fenestration, and exit the proximal end opening. No portion of the guide wire may extend distally beyond the distal end opening.

14 Claims, 30 Drawing Sheets

(51) Int. Cl.
- A61F 2/966 (2013.01)
- A61M 25/09 (2006.01)
- *A61F 2/07* (2013.01)
- *A61F 2/958* (2013.01)
- *A61F 2/95* (2013.01)

(52) U.S. Cl.
CPC .. *A61F 2/07* (2013.01); *A61F 2/958* (2013.01); *A61F 2002/061* (2013.01); *A61F 2002/9511* (2013.01)

(56) References Cited

U.S. PATENT DOCUMENTS

| | | | |
|---|---|---|---|
| 4,861,830 A | 8/1989 | Ward, Jr. | |
| 4,902,508 A | 2/1990 | Badylak et al. | |
| 5,017,664 A | 5/1991 | Grasel et al. | |
| 5,380,304 A | 1/1995 | Parker | |
| 5,542,434 A | 8/1996 | Imran et al. | |
| 5,554,183 A * | 9/1996 | Nazari | 623/1.49 |
| 5,554,389 A | 9/1996 | Badylak et al. | |
| 5,628,783 A | 5/1997 | Quiachon et al. | |
| 5,702,439 A | 12/1997 | Keith et al. | |
| 5,728,122 A | 3/1998 | Leschinsky et al. | |
| 5,733,337 A | 3/1998 | Carr, Jr. et al. | |
| 5,746,766 A | 5/1998 | Edoga | |
| 5,800,521 A * | 9/1998 | Orth | 623/1.23 |
| 5,984,955 A | 11/1999 | Wisselink | |
| 5,993,844 A | 11/1999 | Abraham et al. | |
| 6,099,548 A | 8/2000 | Taheri | |
| 6,099,567 A | 8/2000 | Badylak et al. | |
| 6,206,931 B1 | 3/2001 | Cook et al. | |
| 6,290,666 B1 * | 9/2001 | Devonec | 623/1.16 |
| 6,325,819 B1 | 12/2001 | Pavcnik et al. | |
| 6,358,284 B1 | 3/2002 | Fearnot et al. | |
| 6,379,710 B1 | 4/2002 | Badylak | |
| 6,416,499 B2 | 7/2002 | Paul, Jr. | |
| 6,485,515 B2 | 11/2002 | Strecker | |
| 6,524,335 B1 | 2/2003 | Hartley et al. | |
| 6,533,782 B2 | 3/2003 | Howell et al. | |
| 6,589,227 B2 | 7/2003 | Sønderskov Klint | |
| 6,666,892 B2 | 12/2003 | Hiles et al. | |
| 6,752,826 B2 | 6/2004 | Holloway et al. | |
| 6,939,377 B2 | 9/2005 | Jayaraman et al. | |
| 7,025,758 B2 | 4/2006 | Klint | |
| 7,105,020 B2 | 9/2006 | Greenberg et al. | |
| 7,172,580 B2 | 2/2007 | Hruska et al. | |
| 7,335,224 B2 | 2/2008 | Øhlenschlæger | |
| 7,407,509 B2 | 8/2008 | Greenberg et al. | |
| 7,435,253 B1 | 10/2008 | Hartley et al. | |
| 7,537,606 B2 | 5/2009 | Hartley et al. | |
| 7,591,843 B1 | 9/2009 | Escano et al. | |
| 7,611,529 B2 | 11/2009 | Greenberg et al. | |
| 7,637,920 B2 | 12/2009 | von Lehe et al. | |
| 7,651,519 B2 | 1/2010 | Dittman | |
| 7,674,239 B2 | 3/2010 | Sisken et al. | |
| 7,722,657 B2 | 5/2010 | Hartley | |
| 7,867,270 B2 | 1/2011 | Hartley et al. | |
| 7,976,575 B2 | 7/2011 | Hartley | |
| 8,034,094 B2 | 10/2011 | Aoba et al. | |
| 8,043,354 B2 | 10/2011 | Greenberg et al. | |
| 8,292,951 B2 | 10/2012 | Muzslay | |
| 8,974,518 B2 * | 3/2015 | Bruszewski et al. | 623/1.23 |
| 2001/0034514 A1 | 10/2001 | Parker | |
| 2002/0187288 A1 | 12/2002 | Lim et al. | |
| 2003/0050684 A1 * | 3/2003 | Abrams et al. | 623/1.11 |
| 2003/0149471 A1 | 8/2003 | Briana et al. | |
| 2004/0106974 A1 | 6/2004 | Greenberg et al. | |
| 2004/0116996 A1 * | 6/2004 | Freitag | 623/1.11 |
| 2004/0230287 A1 | 11/2004 | Hartley et al. | |
| 2006/0095118 A1 | 5/2006 | Hartley | |
| 2006/0184228 A1 | 8/2006 | Khoury | |
| 2006/0229707 A1 | 10/2006 | Khoury | |
| 2007/0043425 A1 | 2/2007 | Hartley et al. | |
| 2007/0078395 A1 | 4/2007 | Valaie | |
| 2007/0100427 A1 * | 5/2007 | Perouse | 623/1.11 |
| 2007/0233223 A1 * | 10/2007 | Styrc | 623/1.11 |
| 2007/0244547 A1 | 10/2007 | Greenan | |
| 2007/0299499 A1 * | 12/2007 | Hartley et al. | 623/1.11 |
| 2008/0262596 A1 * | 10/2008 | Xiao | 623/1.14 |
| 2008/0294234 A1 | 11/2008 | Hartley et al. | |
| 2009/0043377 A1 | 2/2009 | Greenberg et al. | |
| 2009/0099640 A1 | 4/2009 | Weng | |
| 2009/0171451 A1 | 7/2009 | Kuppurathanam et al. | |
| 2010/0057077 A1 | 3/2010 | Ducharme | |
| 2010/0262217 A1 * | 10/2010 | Bruszewski | 623/1.11 |
| 2010/0280592 A1 * | 11/2010 | Shin et al. | 623/1.15 |
| 2011/0040366 A1 * | 2/2011 | Goetz et al. | 623/1.12 |
| 2011/0307048 A1 * | 12/2011 | Ivancev et al. | 623/1.11 |
| 2012/0010696 A1 * | 1/2012 | Greenberg et al. | 623/1.12 |
| 2012/0041535 A1 | 2/2012 | Huser et al. | |
| 2012/0046728 A1 | 2/2012 | Huser et al. | |
| 2015/0073525 A1 * | 3/2015 | Aoba et al. | 623/1.11 |
| 2015/0082595 A1 * | 3/2015 | King | 29/401.1 |

FOREIGN PATENT DOCUMENTS

| | | |
|---|---|---|
| IE | 20000744 A1 | 5/2001 |
| JP | 2009-538698 A | 11/2009 |
| JP | 2012-040378 A | 3/2012 |
| WO | WO 9822158 A2 | 5/1998 |
| WO | WO 98/53761 | 12/1998 |
| WO | WO 2007/142962 A2 | 12/2007 |
| WO | WO 2010/127040 A1 | 4/2010 |
| WO | WO 2011/116308 A1 | 9/2011 |

OTHER PUBLICATIONS

Office Action, and English language translation thereof, in corresponding Japanese Application No. 2013-259823, dated Dec. 2, 2014, 8 pages.

Extended European Search Report, European Application No. EP 11275106.0, dated Dec. 14, 2011, pp. 1-6, European Patent Office, Germany.

Extended European Search Report, European Application No. EP 12197881.1, dated Apr. 9, 2013, pp. 1-5, European Patent Office, The Netherlands.

* cited by examiner

PRELOADED WIRE FOR ENDOLUMINAL DEVICE

CROSS-REFERENCE TO RELATED APPLICATIONS

This application is a continuation-in-part of U.S. patent application Ser. No. 13/208,793, filed Aug. 12, 2011, which claims priority and the benefit of U.S. provisional Patent Application Ser. No. 61/373,610, filed Aug. 13, 2010; this application also claims priority and the benefit of U.S. provisional Patent Application Ser. No. 61/579,027, filed Dec. 22, 2011. Each of these applications is incorporated herein by reference in its entirety.

TECHNICAL FIELD

The present disclosure relates generally to medical devices. More particularly, it relates to an endoluminal prosthesis for implantation within a human or animal body for repair of damaged vessels, ducts, or other physiological pathways and systems and methods for delivering such an endoluminal prosthesis.

BACKGROUND

The deployment of a medical device, such as an endoluminal prosthesis, into the vessel of a patient from a remote location by the use of a catheter delivery device is generally known. A catheter delivery device carrying an endoluminal prosthesis is delivered into a vessel over a guide wire previously placed within the vessel. Once the catheter device is positioned, the prosthesis is released and expanded to repair the vessel.

An endoluminal prosthesis can be used, for example, to repair diseased and/or damaged conduits, such as blood vessels, the esophagus, the trachea, and the like. Over the past decade, endoluminal prostheses have become a popular option for treating damage and disease to blood vessels, such as abdominal aortic and/or thoracic aneurysms.

In some cases, it may be necessary to deploy an endoluminal prosthesis in a major vessel (e.g., the aorta) at or near an intersecting branch vessel (e.g., innominate, carotid, subclavian, celiac, SMA, and renal arteries). In these cases, an endoluminal prosthesis may be provided with one or more fenestrations so that the prosthesis can overlap the branch vessels without blocking flow to these vessels. Once the prosthesis is placed in the main vessel, it may be necessary to provide interventional access between the main vessel and a branch vessel. For example, a physician may desire to deliver additional interventional catheters carrying balloons, stents, grafts, imaging devices, and the like through the fenestration.

Before such a catheter device can be delivered through the fenestration to a target vessel, however, a guide wire must be provided and delivered through the fenestration to the target vessel. Typically, this requires multiple steps. First, the physician must deliver and navigate a set of catheters and wires to pass a guide wire through the fenestration. Once the fenestration is cannulated, the physician must then deliver and navigate a separate set of catheters and wires to pass a guide wire into the target vessel. These procedures are labor intensive, involve manipulating multiple wires in a vessel at the same time, and depend heavily on the skill of the physician to cannulate both the fenestration and the target vessel. The steps become even more complicated and numerous when the physician needs to cannulate more than one fenestration and more than one target vessel. In addition, the complexity of the procedure increases as the number of cannulating wires increases, since the physician must take precaution to ensure that the multiple wire ends do not become entangled, or that they do not inadvertently contact and damage the prosthesis or a vessel wall.

The present disclosure is directed to devices and systems that overcome these, and other issues involved with cannulating fenestrated devices. In particular, the present disclosure is directed to devices, systems, and methods for delivering and deploying a prosthesis comprising a fenestration, where such devices, systems, and methods include a precannulated fenestration. The precannulated fenestration reduces the potential number of steps and devices, and decreases the complexity of performing endoluminal procedures involving fenestrated prosthetic devices.

SUMMARY

The present embodiments provide an endoluminal prosthesis for implantation within a human or animal body for repair of damaged vessels, ducts, or other physiological pathways and systems and method for delivering such an endoluminal prosthesis.

In one example, a system may include an endoluminal prosthesis and a guide wire. The prosthesis may include a tubular body including a graft material wall, a proximal end opening, a distal end opening, and a lumen extending longitudinally therein. The prosthesis may include a first fenestration in the graft material wall and a second fenestration in the graft material wall. The first fenestration and the second fenestration may be spaced from one another circumferentially about the tubular body. The guide wire may have a first end and a second end both extending from a region proximal of the proximal end opening. The guide wire may enter the proximal end opening, exit the first fenestration, partially traverse an exterior surface of the prosthesis, enter the second fenestration, and exit the proximal end opening. No portion of the guide wire may extend distally beyond the distal end opening.

In another example, a system may include an endoluminal prosthesis and a guide wire. The prosthesis may include a tubular body including a graft material wall, a proximal end opening, a distal end opening, and a lumen extending longitudinally therein. The prosthesis may include a first fenestration in the graft material wall and a second fenestration in the graft material wall and spaced circumferentially from the first fenestration. The guide wire may have a first end and a second end both extending proximal of the proximal end opening. The guide wire may enter the proximal end opening, exit the first fenestration, partially traverse an exterior surface of the prosthesis, enter the second fenestration, and exit the proximal end opening. A segment of the guide wire extending between the first fenestration and the second fenestration may be positioned longitudinally between the proximal end opening and the distal end opening of the prosthesis.

In another example, a method of deploying a branch prosthesis in a main prosthesis may include providing the main prosthesis and a guide wire. The main prosthesis may include a tubular body including a graft material wall, a proximal end opening, a distal end opening, a first fenestration in the graft material wall, and a second fenestration in the graft material wall. The guide wire may enter the proximal end opening, exit the first fenestration, partially traverse an exterior surface of the prosthesis, enter the second fenestration, and exit the proximal end opening. No portion of the guide wire may extend distally beyond the distal end opening. The method may include guiding an introducer over a first end of the guide wire and through the first fenestration of the prosthesis. The method may include guiding an introducer over a second end of the guide wire and through the second fenestration of the prosthesis.

Other systems, methods, features, and advantages of the invention will be, or will become, apparent to one with skill in the art upon examination of the following figures and detailed description. It is intended that all such additional systems, methods, features, and advantages be within the scope of the invention, and be encompassed by the following claims.

BRIEF DESCRIPTIONS OF THE DRAWINGS

DETAILED DESCRIPTION OF THE DRAWINGS AND THE PRESENTLY PREFERRED EMBODIMENTS

Figure 1:
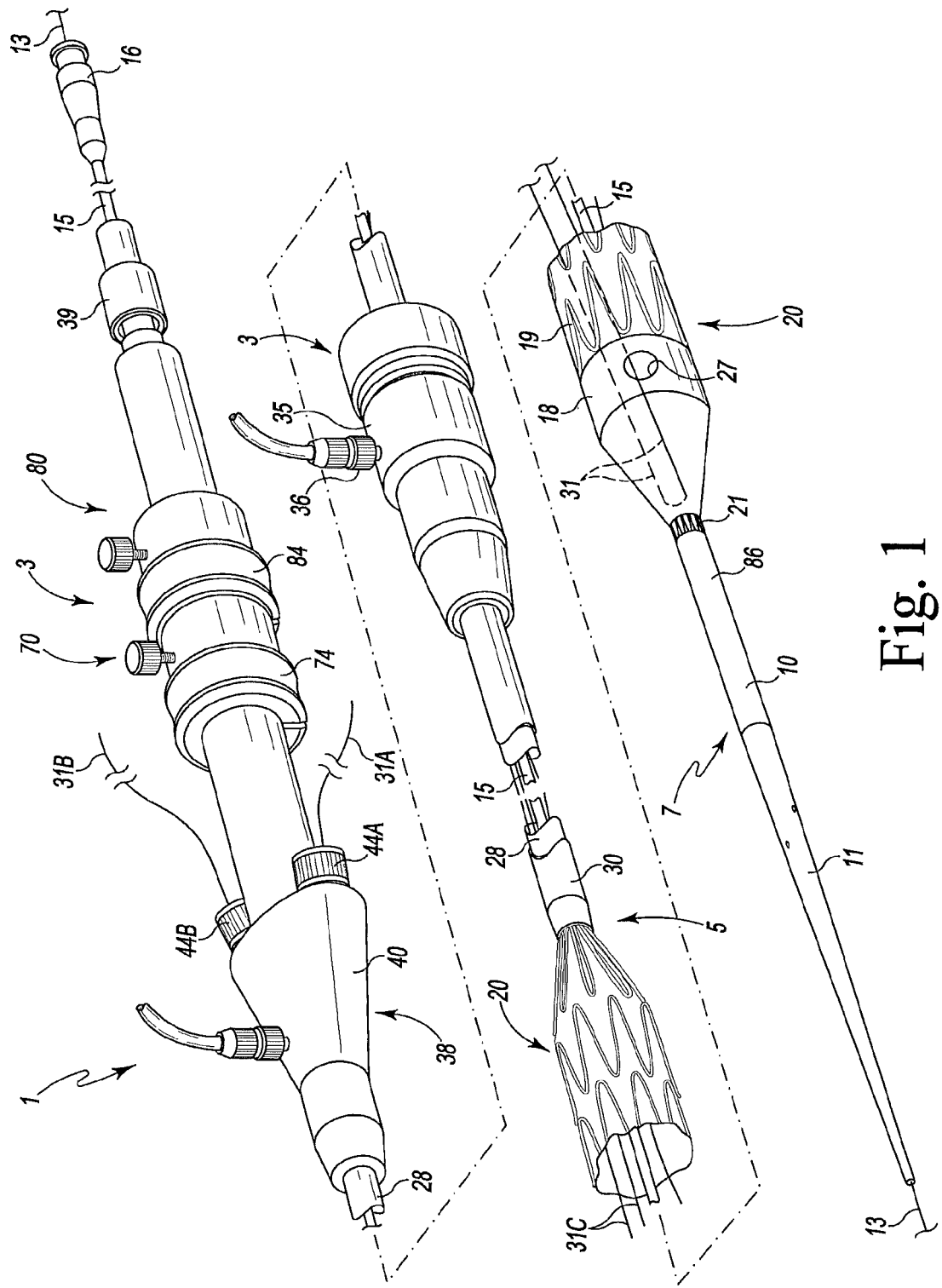
FIG. 1 depicts one example of a device for delivering and deploying an endoluminal prosthesis.

The present disclosure relates to an endoluminal prosthesis for implantation within a human or animal body for repair of damaged vessels, ducts, or other physiological pathways and systems and methods for delivering such an endoluminal prosthesis.

Throughout the specification, when referring to any portion of an endoluminal prosthesis or a device or system for delivering an endoluminal prosthesis, the terms "proximal" and "proximally" shall denote a position, direction, or orientation that is generally toward, or in the direction of, the operator of the device or system. The terms "distal" and "distally" shall denote a position, direction, or orientation that is generally toward, or in the direction of, the patient.

Throughout the specification, unless the context requires otherwise, the words "comprise," "include," "and have," and variations such as "comprising," "including," and "having," imply the inclusion of an item or group of items, without the exclusion of any other item or group of items.

The term "prosthesis" means any device, object, or structure that supports, repairs, or replaces, or is configured to support, repair, or replace a body part or a function of that body part. The term prosthesis also can mean a device that enhances or adds functionality to a physiological system. The term prosthesis may include, for example and without limitation, a stent, stent graft, filter, valve, balloon, embolization coil, and the like.

The term "stent" means any device or structure that provides or is configured to provide rigidity, expansion force, or support to a body part, for example, a diseased, damaged, or otherwise compromised body lumen. A stent may include any suitable biocompatible material, including, but not limited to fabrics, metals, plastics, and the like. Examples of suitable materials may include metals such as stainless steel and nitinol, and plastics such as polyethylene terephthalate (PET), polytetrafluoroethylene (PTFE), and polyurethane.

A stent may be "expandable," that is, it may be capable of being expanded to a larger-dimension configuration. A stent may expand by virtue of its own resilience (i.e., self-expanding), upon the application of an external force (i.e., balloon-expandable), or by a combination of both. In one example, a stent may have one or more self-expanding portions and one or more balloon-expandable portions. An example of a suitable self-expanding stent includes Z-STENTS®, which are available from Cook Medial Incorporated, Bloomington, Ind., USA.

The term "graft" describes an object, device, or structure that is joined or that is capable of being joined to a body part to enhance, repair, or replace a portion or a function of that body part. Grafts that can be used to repair body vessels may include, for example, films, coatings, or sheets of material that are formed or adapted to conform to the body vessel that is being enhanced, repaired, or replaced. A stent may be attached to or associated with a graft to form a "stent graft."

A graft material may include a biocompatible synthetic or biological material. Examples of suitable synthetic materials may include fabrics, woven and non-woven materials, and porous and non-porous sheet materials. One exemplary synthetic graft material includes a woven polyester having a twill weave and a porosity of about 350 ml/min/cm$^2$, and is available from VASCUTEK® Ltd., Renfrewshire, Scotland, UK. Other synthetic graft materials may include biocompatible materials such as polyester, polytetrafluoroethylene (PTFE), polyurethane, and the like. Examples of suitable biological materials may include, for example, pericardial tissue and extracellular matrix materials such as SIS.

Examples of suitable graft materials are described in U.S. Pat. Nos. 4,502,159, 4,675,361, 4,861,830, 4,902,508, 5,017,664, 5,733,337, 6,206,931, 6,358,284, 6,379,710, 6,666,892, 6,752,826, and 6,939,377, in U.S. Patent Application Publication Nos. 2002/0187288 and 2003/0149471, and in International Patent Application Publication No. WO 98/22158, each of which is incorporated by reference herein in its entirety.

The term "vessel" refers to a tube, cavity, duct, or canal in which fluid may be contained, conveyed, and/or circulated. A body vessel (as opposed to a prosthetic vessel) is a vessel that exists naturally, or is formed naturally in the body. Examples of body vessels may include, but are not limited to, blood vessels such as the aorta and the femoral artery, the esophagus, the trachea, the ureter, the bile duct, and the like. Examples of prosthetic vessels may include, but are not limited to, stents, grafts, stent grafts, venous or aortal valves, vena cava filters, and the like.

The term "lumen" describes a space within a vessel in which fluid may be contained, conveyed, and/or circulated. The term "endoluminal" means within a lumen, and can refer to objects that are found or that can be placed within a lumen, or methods or processes that occur within a lumen. An "endoluminal prosthesis" is a prosthesis that is found or that can be placed within a lumen. Examples of endoluminal prostheses may include, but are not limited to, stents, grafts, stent grafts, venous or aortal valves, vena cava filters, and the like. An endoluminal prosthesis may be generally tubular and include one or more lumens. Examples of tubular prostheses may include, but are not limited to, straight, curved, branched, and bifurcated prostheses.

The term "fenestration" refers to an opening provided through a surface of a prosthesis from the interior of the prosthesis to the exterior of the prosthesis. A fenestration may have any suitable geometry including, for example, circular, semi-circular, oval, oblong, or any other shape.

FIG. 1 shows a device for delivering and deploying an endoluminal prosthesis 20 in a vessel of a patient. The device includes a delivery catheter 1 comprising an external manipulation section 3, a proximal positioning mechanism or attachment region 5, and a distal positioning mechanism or attachment region 7. The proximal and distal attachment regions 5, 7 are positioned inside the patient's body during a medical procedure, whereas the external manipulation section 3 is positioned outside the patient's body. During a procedure, the operator controls or manipulates the external manipulation section 3 to position the proximal and distal attachment regions 5, 7 and to release the prosthesis 20 into the vessel.

The delivery and deployment device includes an endoluminal prosthesis 20 disposed at a distal end portion of the delivery catheter 1 between the proximal and distal attachment regions 5, 7. The prosthesis 20 may comprise a tubular graft material 18, as described above. The prosthesis 20 may additionally or alternatively comprise one or more expandable stents 19 disposed at least partly coextensive with the graft material 18. Each stent 19 may be coupled to an interior and/or an exterior surface of the graft material 18. The prosthesis 20 shown in FIG. 1 comprises a graft material 18 and a plurality of expandable stents 19 disposed coextensive with the graft material 18. In addition, the prosthesis 20 shown in FIG. 1 includes a stent 21 extending from the distal end of the graft material 18 so that it is at least partially uncovered from the graft material 18. The bare stent 21 expands and engages the body lumen, thereby anchoring the prosthesis 20 and preventing the prosthesis from moving after implantation. The stent 21 may comprise anchoring means such as, for example, barbs (not shown) that are configured to grasp the walls of the body lumen.

The prosthesis 20 shown in FIG. 1 further comprises a fenestration 27 disposed in the graft material between proximal and distal end openings of the tubular graft 18. The fenestration 27 provides a fluid pathway through the side wall of the graft tube and allows the prosthesis 20 to be placed in a main vessel in overlapping relationship with an intersecting branch vessel, without interrupting flow to the branch vessel.

The prosthesis 20 is disposed at a distal end portion of the delivery catheter 1. The prosthesis 20 is retained over the delivery catheter 1 by an elongate sheath 30. The sheath 30 comprises an elongate tubular body having an axial lumen (not shown). The sheath 30 extends proximally to the manipulation region 3. The prosthesis 20 is disposed within an axial lumen of the sheath 30 in a radially-compressed configuration. In FIG. 1, the prosthesis 20 is depicted in a partially deployed state, whereby the sheath 30 is partially retracted over the prosthesis, exposing the prosthesis and allowing it to radially expand.

The sheath 30 preferably comprises a flexible structure that is able to bend and flex to negotiate complex and tortuous inner body lumina. The sheath 30 may comprise a biocompatible plastic such as PTFE, polyethylene, nylon, or the like. Examples of suitable sheath devices and materials are disclosed in U.S. Pat. Nos. 5,380,304, 6,589,227, and 7,025,758, and in U.S. Patent Application Publication Nos. 2001/0034514, 2002/0032408 and 2006/01555302, each of which is incorporated herein by reference in its entirety.

The delivery catheter shown in FIG. 1 further comprises an inner cannula 15 that extends distally from the manipulation region 3 to the distal attachment region 7. The inner cannula 15 has an axial lumen that is configured to receive a guide wire 13. The inner cannula 15 extends distally from a proximal end portion of the delivery catheter 1 to a distal end portion of the catheter. A tapered extension 11 is coupled to the distal end of the cannula 15 and forms the distal end of the delivery catheter 1. Connection means 16 is coupled to the proximal end of the cannula 15. Connection means 16 is adapted to accept a syringe and may be used to introduce reagents into the body lumen.

The cannula 15 is slidingly disposed within the lumen of the sheath 30. The prosthesis 20 is retained over a distal portion of the cannula 15 by the sheath 30. The cannula 15 is preferably flexible so that the device can be advanced within a relatively tortuous vessel, such as a femoral artery or the aortic arch. The cannula 15 may comprise metal, for example aluminum, stainless steel, or nitinol. The cannula 15 is in mechanical communication with the flexible extension 11. This allows the operator to control the flexible extension 11 remotely during a procedure. For example, the operator can rotate or slide the flexible extension 11 relative to the prosthesis 20 by manipulating the cannula 15.

The delivery catheter 1 shown in FIG. 1 further comprises an elongate tubular pusher 28 that extends distally from the manipulation region 3 to the proximal attachment region 5. The cannula 15 is slidably disposed within an axial lumen (not shown) of the pusher 28. The sheath 30 is slidably disposed over a distal end portion of the pusher 28. The pusher 28 may comprise any suitable biocompatible material including metal or plastic. The pusher 28 may comprise a radiopaque material. Suitable materials include, but are not limited to aluminum, nitinol, nylon, polypropylene, and polyethylene. The pusher 28 preferably has high longitudinal column strength to ensure adequate energy transfer between the user and the prosthesis during deployment.

The delivery and deployment device further comprises a haemostatic sealing means 35 for controlling blood loss through the delivery and deployment device. The sealing means 35 is fixedly connected to the sheath 30 and couples the sheath and the pusher 28. The sealing means 35 comprises one or more haemostatic valves (not shown) that provide a haemostatic seal between the sheath 30 and the pusher 28. Suitable haemostatic valves include, for example, disk valves, iris valves, and the like. The haemostatic sealing means 35 also may include a side tube 36 that facilitates the introduction of medical reagents between the pusher 28 and the sheath 30. U.S. Pat. Nos. 6,416,499 and 7,651,519, and U.S. Patent Application Publication Nos. 2005/0171479 and 2007/0078395 describe examples of suitable haemostatic sealing devices that can be used with a delivery catheter described in the present disclosure. Each of these patent references is incorporated by reference herein in its entirety.

The distal end of the pusher 28 is disposed adjacent the proximal end of the prosthesis 20. To deploy the prosthesis 20, the operator slides the sheath 30 proximally while applying distal pressure to the pusher 28 in the user manipulation region 3. The pusher prevents the prosthesis 20 from sliding proximally with the sheath 30 when the sheath is withdrawn. As a result, the sheath 30 retracts proximally over the prosthesis 20, exposing the prosthesis, thereby allowing it to expand radially outwardly.

The proximal end of the pusher 28 is connected to an auxiliary access device 38. The access device 38 comprises a housing 40, a channel 42 extending generally axially through the housing, and a port 44 coupled to the channel 42. The port 44 provides fluid and mechanical communication between the user manipulation section 3 and the channel 42, which provides fluid and mechanical communication with an axial lumen 33 of the pusher 28 which, in turn, provides fluid and mechanical communication with the prosthesis 20.

Figure 3:
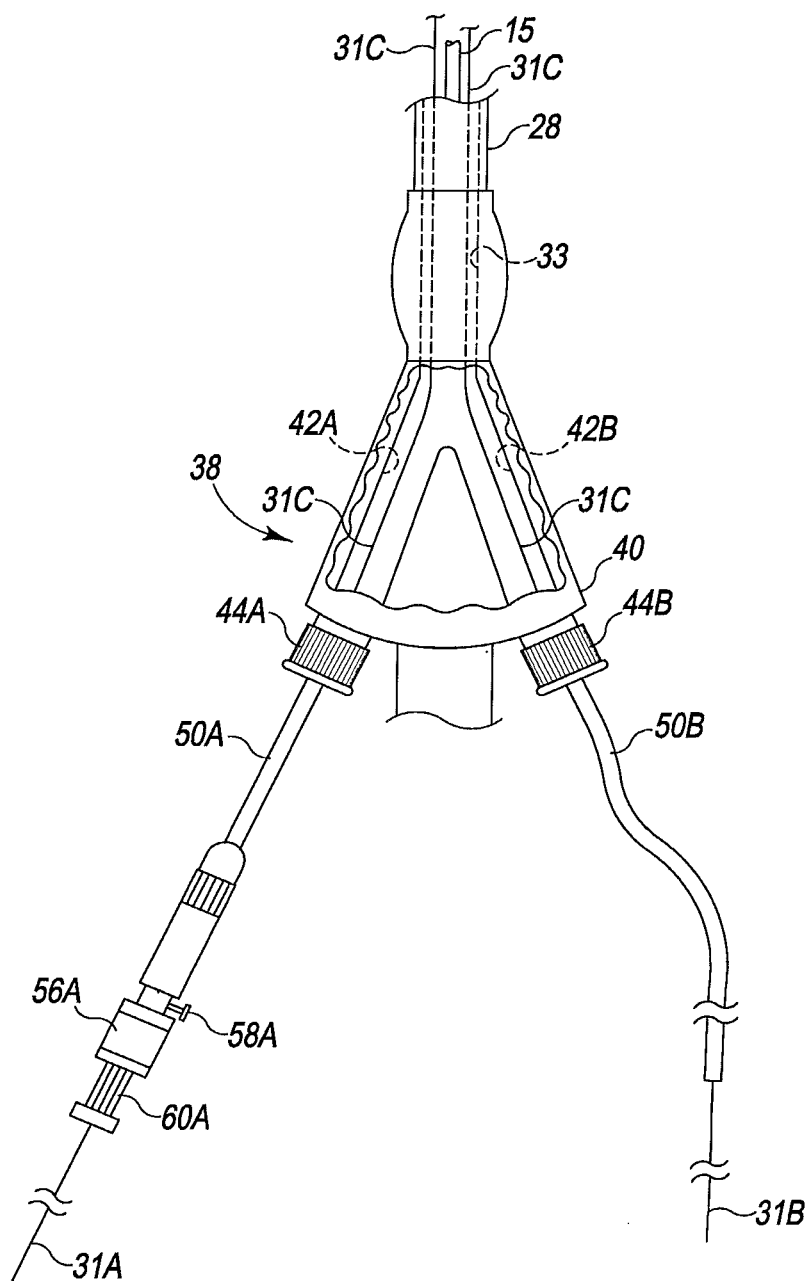
FIG. 3 depicts a proximal portion of one example of a device for delivering and deploying an endoluminal prosthesis, including one example of a prosthesis with a precannulated fenestration.

FIG. 3 depicts an exemplary access device 38 with multiple channels 42A, 42B in communication with multiple ports 44A, 44B. The ports 44A, 44B may be used, for example, to introduce medical reagents to the prosthesis through the pusher 28. Alternatively or additionally, the ports 44A, 44B may be used to introduce auxiliary medical devices such as guide wires or interventional catheters to the prosthesis through the pusher 28.

The access device 38 preferably includes one or more haemostatic valves (not shown), as described above, to control blood loss during a procedure. For example, one or more ports 44A, 44B may comprise one or more disk valves, iris valves, or the like. Alternatively or additionally one or more such valves may be placed within the channel 42 to control blood loss through the access device 38.

Figure 13:
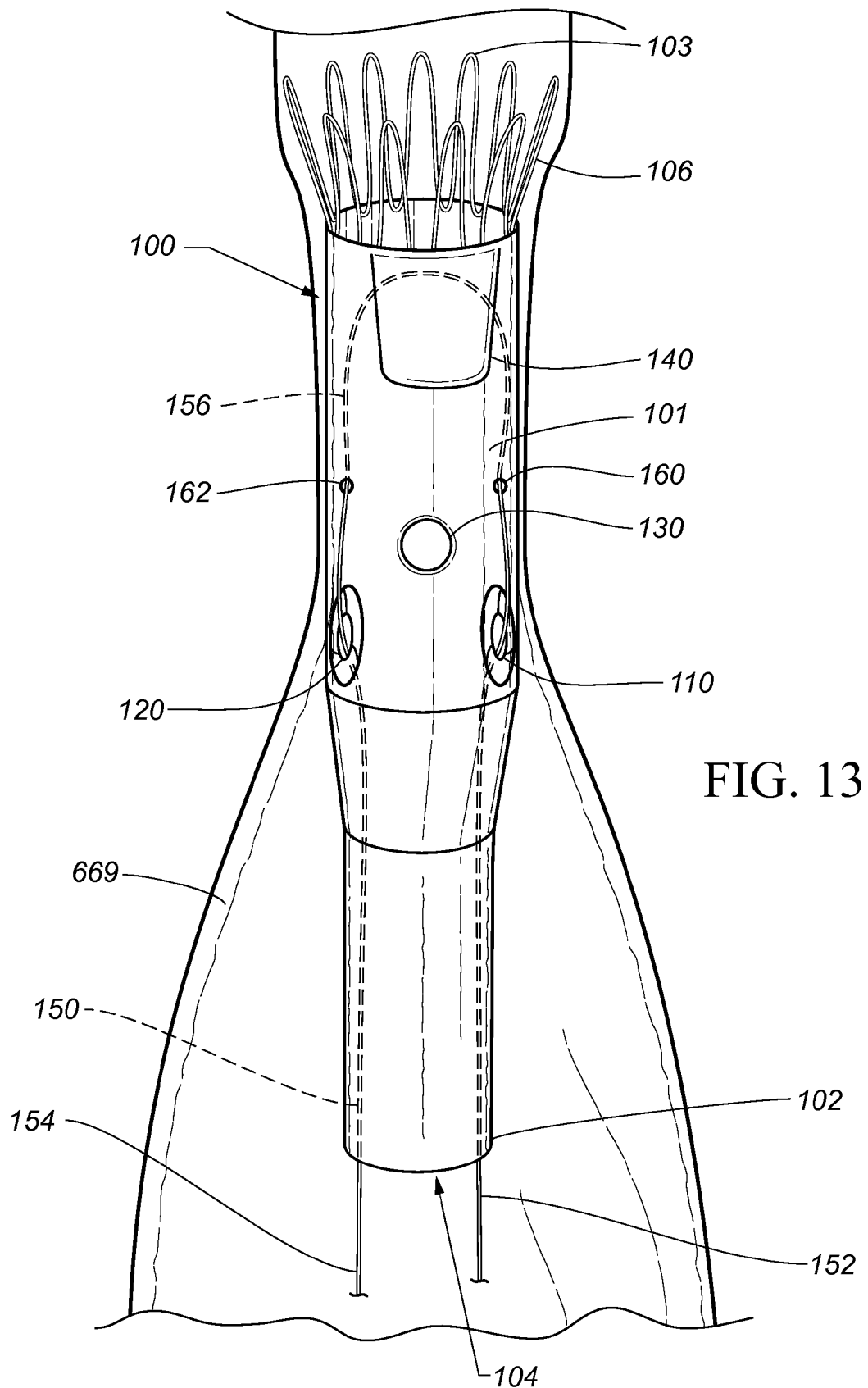
FIG. 13 illustrates one example of an endoluminal prosthesis and a guide wire received in the prosthesis in one example of a preloaded configuration.
Figure 16:
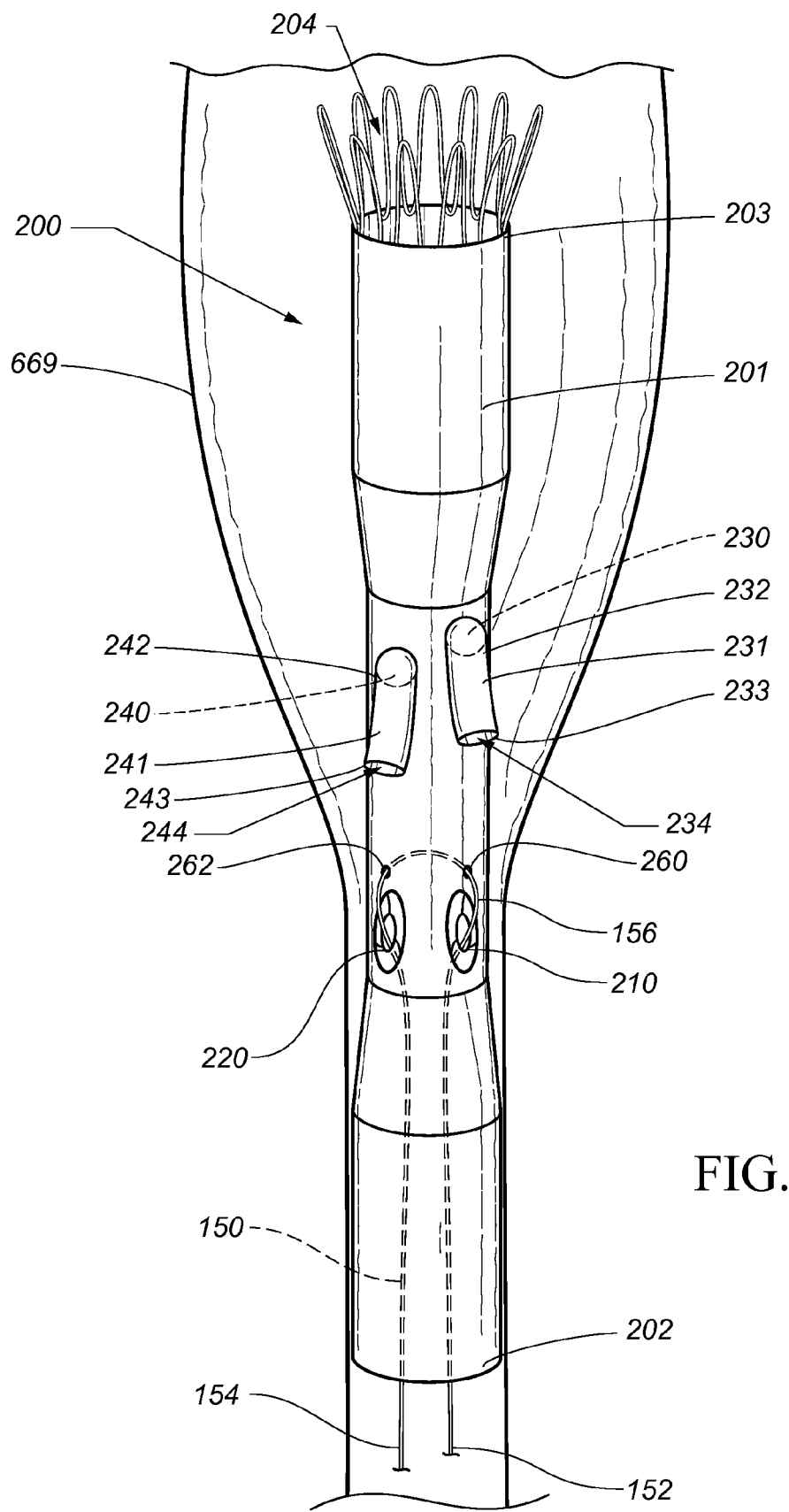
FIG. 16 illustrates one example of an endoluminal prosthesis and a guide wire received in the prosthesis in one example of a preloaded configuration.
Figure 17:
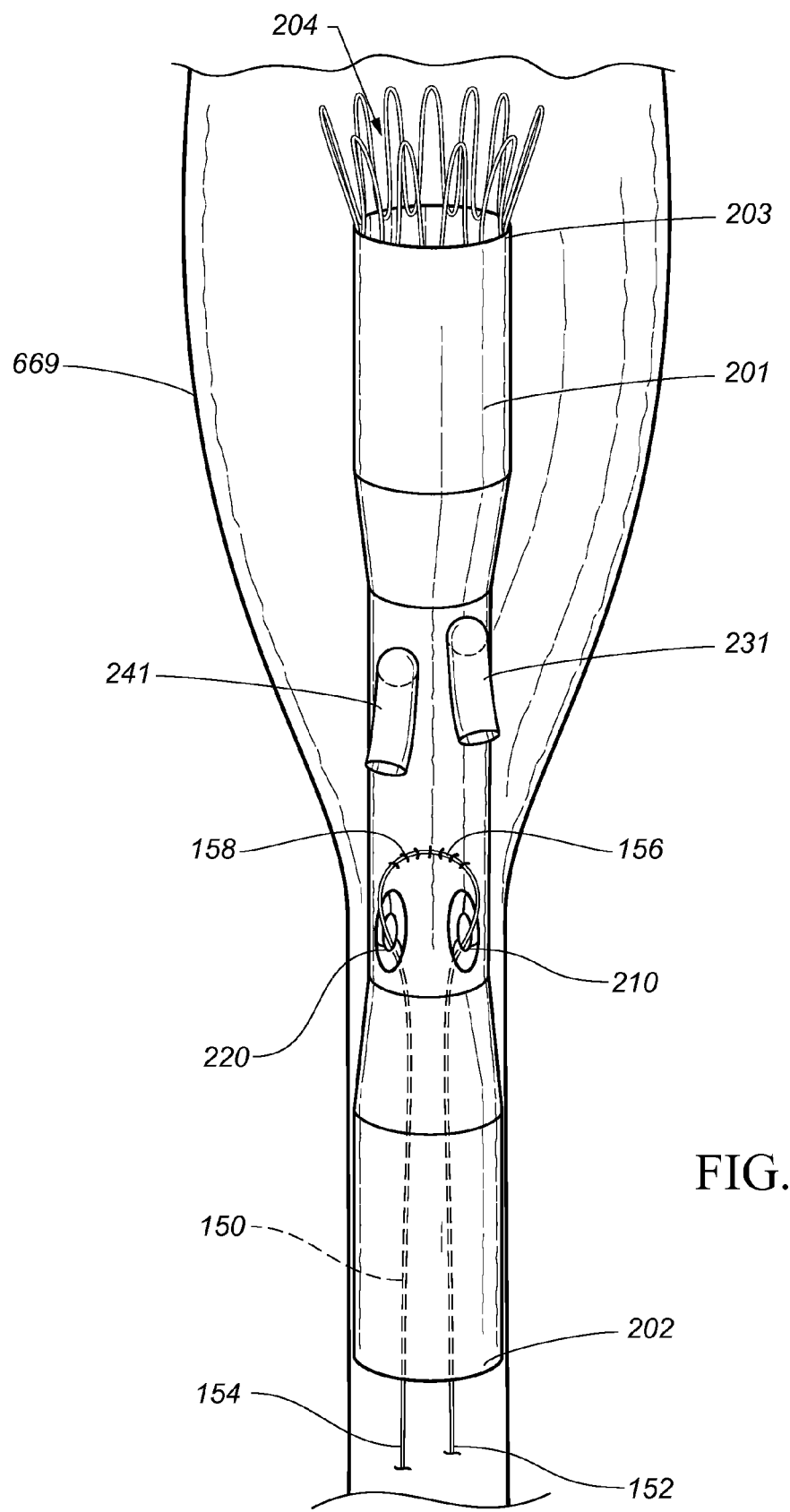
FIG. 17 illustrates one example of an endoluminal prosthesis and a guide wire received in the prosthesis in one example of a preloaded configuration.
Figure 25:
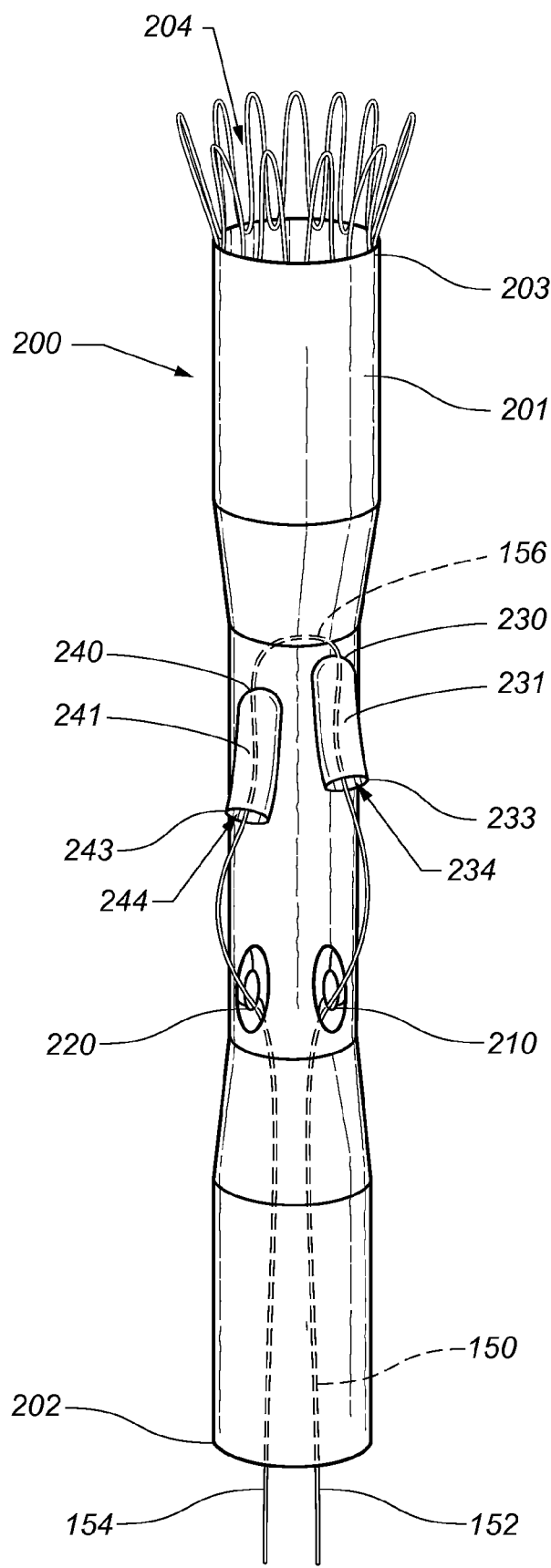
FIG. 25 illustrates one example of an endoluminal prosthesis and a guide wire received in the prosthesis in one example of a preloaded configuration.

FIGS. 1-4 depict delivery and deployment devices comprising a prosthesis 20 with at least one precannulated fenestration 27. The devices comprise a wire 31 having a first end 31A, a second end 31B, and a body portion or intermediate segment 31C disposed between the ends. The wire 31 may be formed from any suitable material, such as a biocompatible metal or plastic, and with dimensions suitable for the particular application. In one example, a wire comprises a highly elastic metal, such as nitinol or the like, and has a diameter in the range of about 0.016 to about 0.018 inches. Wires made of other materials, and having other diameters are also contemplated. Although the delivery catheter 1 is described in connection with delivery of the prosthesis 20 with the wire 31 preloaded therein, the delivery catheter is equally suitable for use with other prostheses (e.g., the prosthesis 100 and/or the prosthesis 200) and wires in other configurations (e.g., the guide wire 150 preloaded in the prostheses 100 as shown in FIG. 13 or the guide wire 150 preloaded in the prosthesis 200 as shown in FIG. 16-17 or 25).

The wire 31 traverses the delivery catheter 1 between proximal and distal end portions of the catheter. Each wire end 31A, 31B is disposed at the external manipulation section 3 of the delivery catheter 1 and can be directly manipulated by the operator during a procedure. The wire 31 extends distally from the first end 31A through the port 44A, through the axial lumen 33 (shown, for example, in FIG. 3) of the delivery catheter, into the lumen of the prosthesis 20 (shown, for example, in FIG. 2), and through the fenestration 27, 27A to the exterior of the graft 18 (shown, for example, in FIGS. 1 and 2). The wire 31 then extends proximally through the lumen of the prosthesis 20, through the axial lumen 33 (shown, for example, in FIG. 3), and through the port 44B toward the second wire end 31B.

In some examples, the lumen 33 may comprise a single lumen structure, and the wire 31 will extend proximally and distally along the delivery catheter through the single lumen structure. In other examples, the lumen 33 may comprise a multi-lumen structure, and the wire 31 will extend proximally and distally along the delivery catheter through separate lumen structures.

The wire 31 is slidably disposed within the fenestration 27, 27A. Consequently, the operator can move the wire 31 proximally through the fenestration 27, 27A by pulling proximally on the first wire end 31A or by pushing distally on the second wire end 31B. Similarly, the operator can move the wire 31 distally through the fenestration 27, 27A by pulling proximally on the second wire end 31B or by pushing distally on the first wire end 31A. This feature provides the operator with control over the positioning and configuration of the wire 31 with respect to the fenestration 27, 27A. For example, it may be possible to manipulate the angle of the wire 31 as it passes through the fenestration 27, 27A by fixing the position of the first wire end 31A and manipulating the second wire end 31B, or vice versa. Other advantages of this feature will be apparent to one of ordinary skill in the art.

Figure 2:
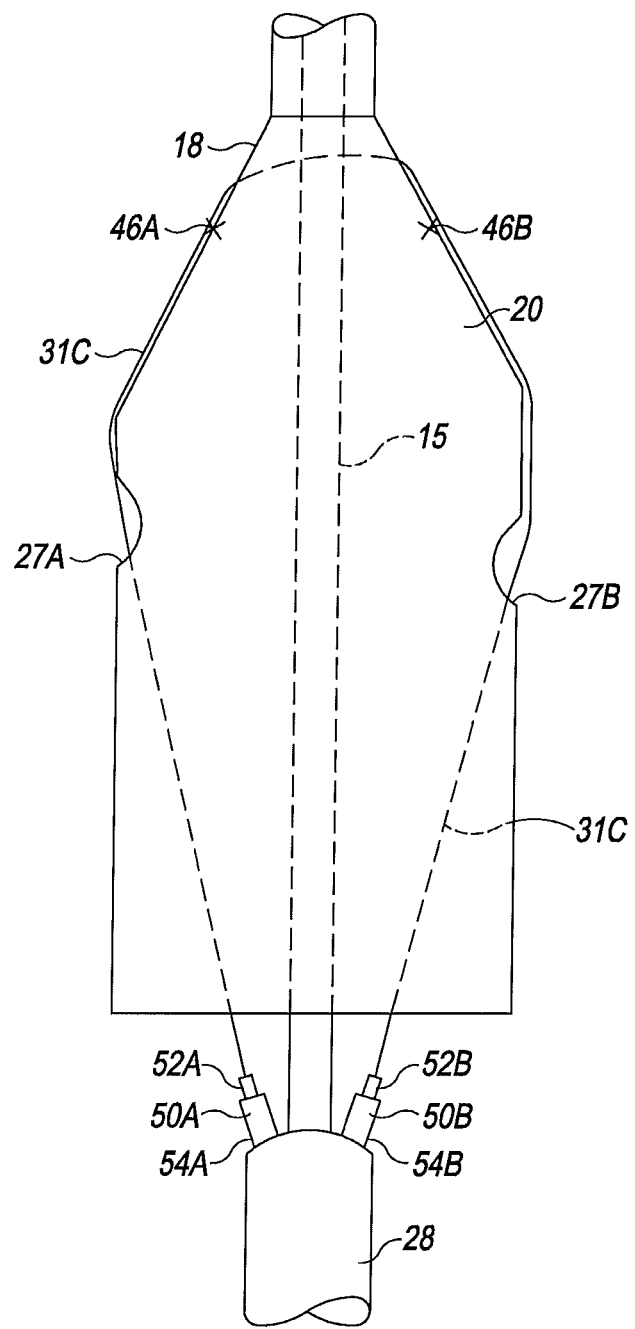
FIG. 2 depicts a distal portion of one example of a device for delivering and deploying an endoluminal prosthesis, including one example of a prosthesis with a precannulated fenestration.

FIG. 2 depicts a prosthesis 20 with multiple (more than one) precannulated fenestrations 27A, 27B. The wire 31 extends distally from the first wire end 31A through the axial lumen 33 of the delivery catheter, into the lumen of the prosthesis 20, and through the fenestration 27A to the exterior of the graft 18. The wire 31 extends proximally from the exterior of the graft 18 through the fenestration 27B into the lumen of the prosthesis 20, and through the axial lumen 33 toward the second wire end 31B. As shown in FIG. 2, one or more stabilizing sutures 46A, 46B may be provided along the prosthesis 20 to attach the wire 31 to the graft material and/or to the stent structure. The sutures 46A, 46B preferably limit lateral movement of the wire, but allow the wire to slide axially through the fenestrations 27A, 27B, as described above.

As shown in FIG. 2, the wire 31 may pass through the lumen of the prosthesis 20 as it traverses the fenestrations 27A, 27B. A segment of the wire 31 extending between the fenestrations 27A, 27B may traverse or extend along the exterior surface of the graft 18. In some examples, the wire extends approximately 3 cm or more away from a fenestration and then passes through the graft material into the lumen of the prosthesis. In other examples, the wire extends approximately 6 cm or less away from a fenestration and then passes through the graft material into the lumen of the prosthesis. In other examples, the wire 31 traverses the fenestrations 27A, 27B without passing through the lumen of the prosthesis 20. In other words, the wire 31 traverses the fenestrations 27A, 27B along the exterior of the graft 18. The wire 31 may at least partially circumferentially traverse the exterior surface of the graft 18 between the fenestrations 27A, 27B. Additionally, or alternatively, the wire 31 may be positioned such that no portion of the wire extends distally beyond the distal end of the prosthesis 20.

Figure 4:
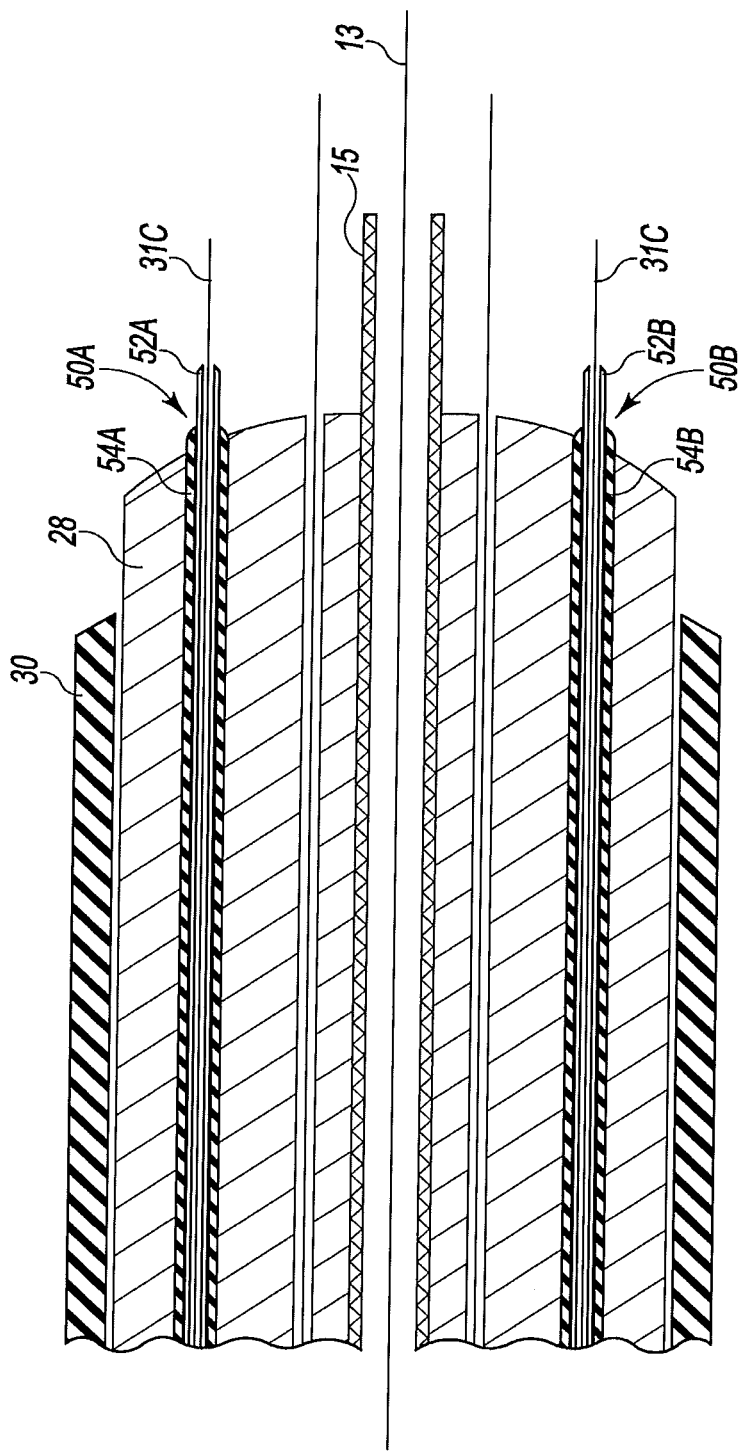
FIG. 4 is a cross-sectional view of a distal portion of one example of a pusher comprising auxiliary catheters and a precannulating wire structure.

As shown in FIGS. 2-4, auxiliary catheters 50A, 50B may be provided and delivered to the prosthesis 20 through the auxiliary access device 38. The auxiliary catheters 50A, 50B may comprise, for example, an elongate sheath 54A, 54B, and an elongate dilator 52A, 52B slidably disposed within an axial lumen of the sheath 54A, 54B. The auxiliary catheters 50A, 50B also may comprise haemostatic sealing means 56A, 56B, as described above, to limit or prevent blood loss through the auxiliary catheters. In addition, the catheters 50A, 50B may comprise side tubes 58A, 58B for introducing medical reagents through the auxiliary catheters. The dilators 52A, 52B terminate proximally at connection means 60A, 60B. The connection means 60A, 60B may be configured for introducing medical reagents through the auxiliary catheters. The auxiliary catheters 50A, 50B are delivered to the prosthesis over the wire ends 31A, 31B through the lumen 33 of the pusher 28, as described above.

The auxiliary catheters 50A, 50B may be used to deliver medical devices, such as guide wires, balloons, stents, stent grafts, imaging devices, and the like, from the user manipulation section 3 to the prosthesis 20. For example, as described in greater detail below, the auxiliary catheters 50A, 50B may be used to cannulate target vessels through the fenestrations 27A, 27B.

Figure 5:
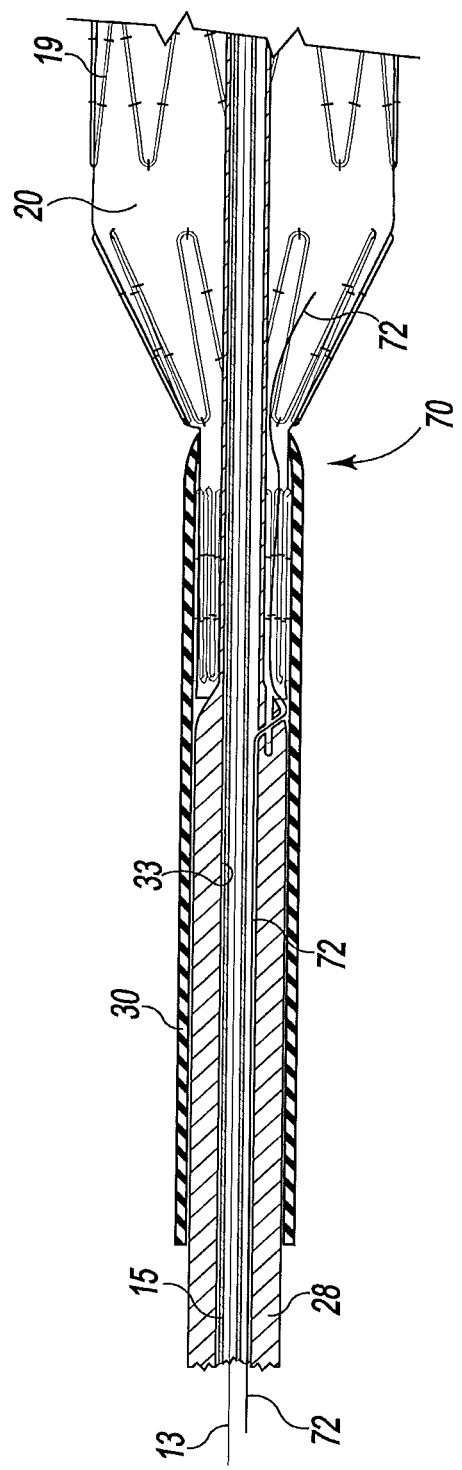
FIG. 5 is a cross-sectional view of one example of a proximal attachment region for a delivery and deployment device.
Figure 6:
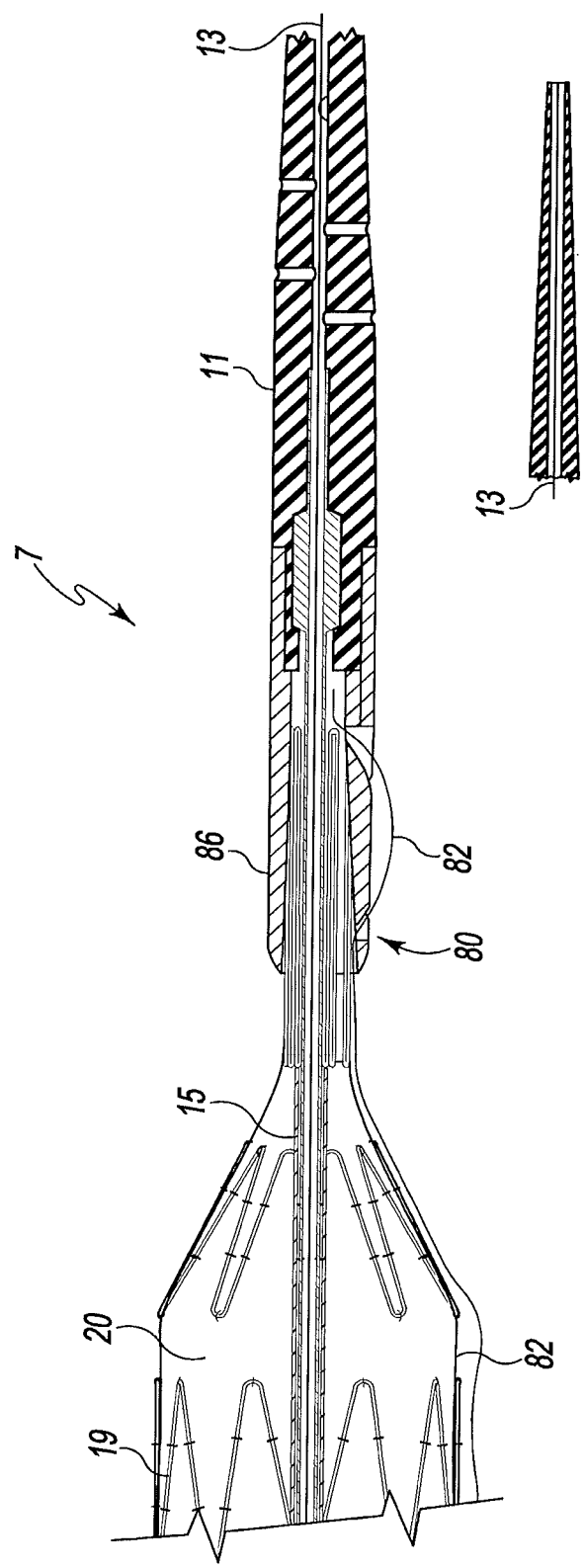
FIG. 6 is a cross-sectional view of one example of a distal attachment region for a delivery and deployment device.

As shown in FIGS. 1, 5, and 6, a device for delivering and deploying a prosthesis may optionally comprise one or more retention devices for retaining at least a portion of the prosthesis. For example, a delivery catheter 1 may comprise a proximal prosthesis retention device 70 for retaining a proximal end of the prosthesis 20 and a distal prosthesis retention device 80 for retaining a distal end of the prosthesis. FIGS. 1 and 5 depict an exemplary proximal prosthesis retention device 70 comprising a proximal trigger wire 72. The trigger wire 72 extends between the prosthesis 20 and the external manipulation section 3 through an axial lumen 33 of the pusher 28. The trigger wire 72 preferably is disposed in an axial lumen separate from the cannulating wire 31 to prevent entanglement between the wires. A proximal end of the wire 72 is connected to control member 74 (FIG. 1). A distal end of the wire 72 is removably connected to the proximal end of the prosthesis 20 (FIG. 5) and limits axial displacement of the prosthesis. The trigger wire 72 can be disconnected from the proximal end of the prosthesis 20 by manipulating the control member 74, for example by sliding the control member proximally to pull the wire away from the prosthesis. Clamping screw 75 may be provided to clamp the control member 74 to prevent inadvertent disengagement of the trigger wire 72.

FIGS. 1 and 6 depict an exemplary distal prosthesis retention device 80 comprising a distal trigger wire 82 and a top cap 86. The cap 86 is fixedly coupled to the inner cannula 15 and holds the distal end of the prosthesis 20 in a radially constrained configuration. The cap 86 prevents the distal end of the prosthesis 20 from expanding during use. The trigger wire 82 extends between the prosthesis 20 and the external manipulation section 3 through an axial lumen 33 of the pusher 28. The trigger wire 82 preferably is disposed in an axial lumen separate from the cannulating wire 31 to prevent entanglement of the wires. A proximal end of the wire 82 is connected to the control member 84 (FIG. 1). A distal end of the wire 82 is removably connected to the distal end of the prosthesis 20 and to the cap 86. The trigger wire 82 can be disconnected from the prosthesis 20 and the cap 86 by manipulating the control member 84, for example, by sliding the control member proximally to pull the wire away from the prosthesis and the cap. A clamping screw 85 may be provided to clamp the control member 84 to prevent inadvertent disengagement of the trigger wire 82. Once the wire 82 disengages the prosthesis 20 and the cap 86, the cap can be removed from the prosthesis by sliding the inner cannula 15 distally with respect to the pusher 28.

Various devices and systems for retaining proximal, distal, and medial portions of a prosthesis are disclosed in the patent literature. For example, U.S. Pat. Nos. 6,524,335, 7,335,224, 7,435,253, 7,537,606, 7,611,529, 7,651,519, and 7,722,657, and U.S. Patent Application Publication Nos. 2004/230287, 2006/0004433, 2007/0043425, and 2008/0294234 disclose devices and systems that are suitable for use with the present invention. Each of these patent references is incorporated herein by reference in its entirety.

FIGS. 7-12 depict various stages of a method for delivering and deploying a prosthesis comprising a precannulated fenestration into the aorta. Although the method is described in relation to a device for treating the aorta, it can readily be applied to other devices and indications.

A delivery catheter 1, as described, for example with respect to FIG. 1, is provided and comprises a pusher 28 and an inner cannula 15 slidingly disposed within an axial lumen of the pusher. The delivery catheter 1 is slidingly disposed within an axial lumen of the sheath 30. The prosthesis 20 is disposed over a distal end portion of the delivery catheter 1 within the axial lumen of sheath 30. A top cap 86 retains a distal end portion of the prosthesis 20 to prevent premature radial expansion of the distal end of the prosthesis as the sheath 30 is retracted proximally over the delivery catheter 1. Although not shown in FIGS. 7-12, the prosthesis 20 may comprise one or more expandable stents, as described above.

Figure 7:
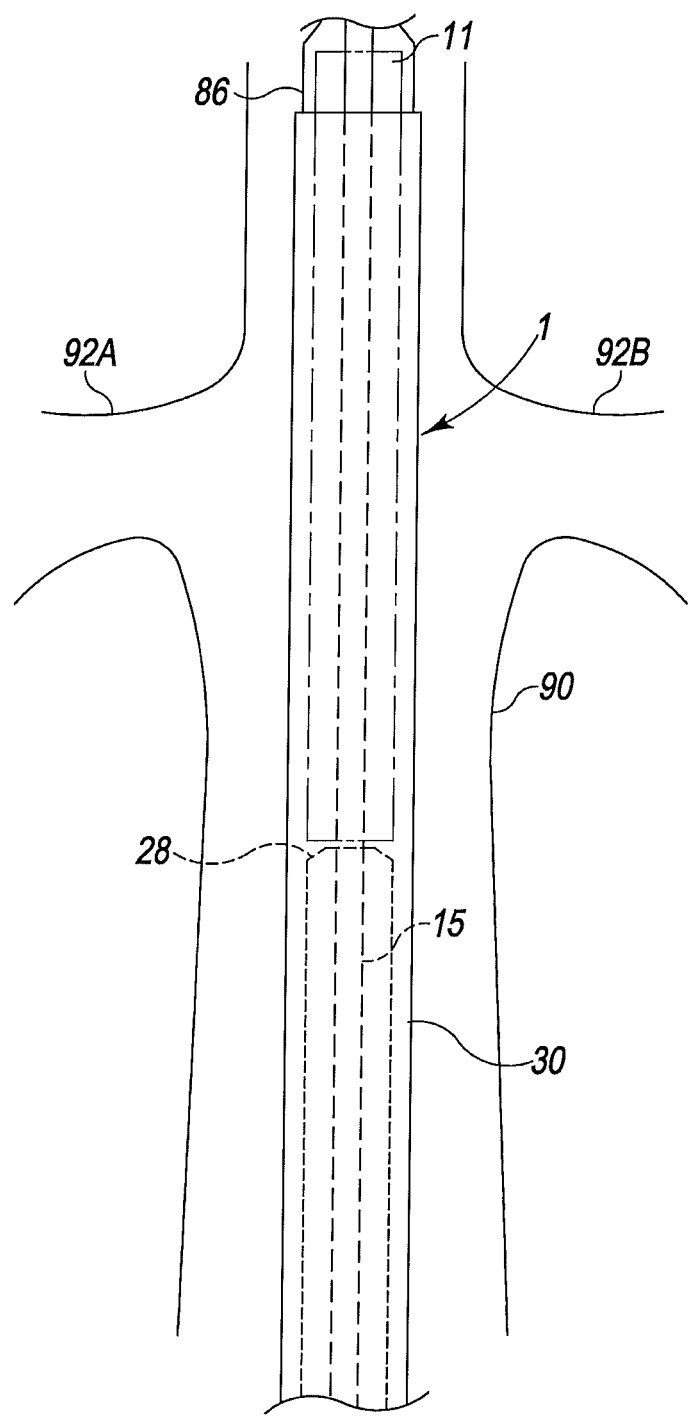
FIGS. 7-12 depict various stages of one example of a method of using a delivery and deployment device including one example of a prosthesis with precannulated fenestrations.

FIG. 7 depicts the delivery and deployment device disposed in an undeployed configuration within a vessel 90 (such as the aorta). The device comprises a prosthesis 20 with multiple fenestrations 27A, 27B sized and configured to provide fluid communication between the lumen of the prosthesis 20 and the branch vessels 92A, 92B (such as renal arteries) after the prosthesis is deployed. Consequently, the prosthesis 20 can be placed within the vessel 90 so that it overlaps the branch vessels 92A, 92B without occluding the branch vessels. The prosthesis comprises precannulated fenestrations 27A, 27B, as described above. In particular, a wire 31 is provided having a first end 31A, a second end 31B, and a wire body 31C. The wire 31 extends distally from the first wire end 31A through the axial lumen 33 of the delivery catheter, into the lumen of the prosthesis 20, and through the fenestration 27A to the exterior of the graft 18. The wire 31 extends proximally from the exterior of the graft 18 through the fenestration 27B into the lumen of the prosthesis 20, and through the axial lumen 33 toward the second wire end 31B.

The delivery catheter 1 may be delivered within the vessel 90 in a conventional manner. A guide wire (not shown) is introduced, for example, into a femoral artery and advanced into the vessel until the tip of the guide wire extends beyond the region in which the prosthesis 20 will be placed. The delivery and deployment device is then inserted over the guide wire 13, via the inner cannula 15, into the vessel 90 and positioned by radiographic techniques generally known in the art. Provision may be made for a separate angiographic catheter (not shown) at the level of the branch vessels 92.

At this stage, the prosthesis 20 is disposed in a compressed configuration within the top cap 86 and an axial lumen of the sheath 30. An auxiliary catheter 50A may be provided and inserted over the first wire end 31A and through the port 44A into an axial lumen of the delivery catheter 1. Likewise, an auxiliary catheter 50B may be provided and inserted over the second wire end 31B and through port 44B into an axial lumen of the delivery catheter 1.

Figure 8:
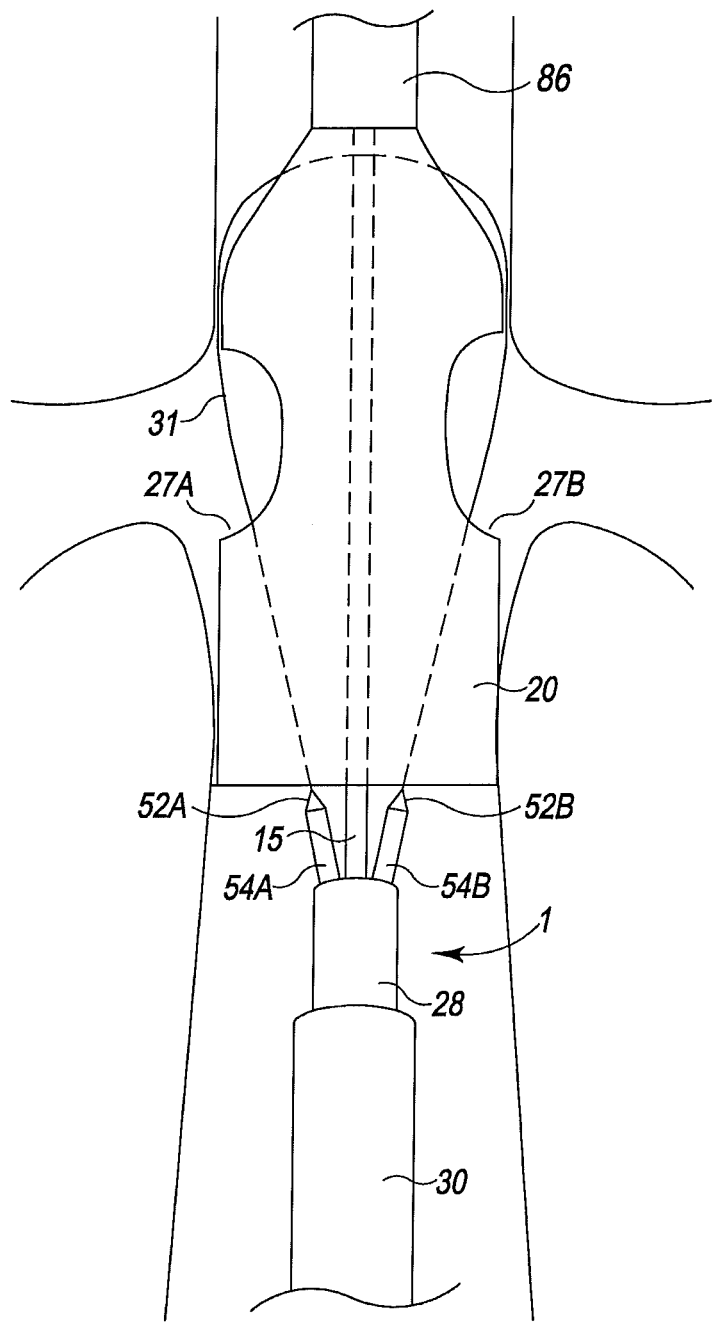

The delivery and deployment device is positioned within the vessel by radiographic means so that the prosthesis 20 overlaps the ostia of, and fenestrations 27A, 27B align with, the branch vessels 92A, 92B. Once the device is in a proper position, the sheath 30 is retracted to expose the prosthesis 20. This action releases the prosthesis so that it can expand radially toward the vessel walls, as shown in FIG. 8. The top cap 86 retains the distal end of the prosthesis 20, however, and prevents it from expanding at this stage. The operator may release the distal end of the prosthesis 20 at a desired stage by sliding the top cap 86 distally with respect to the prosthesis.

Figure 9:
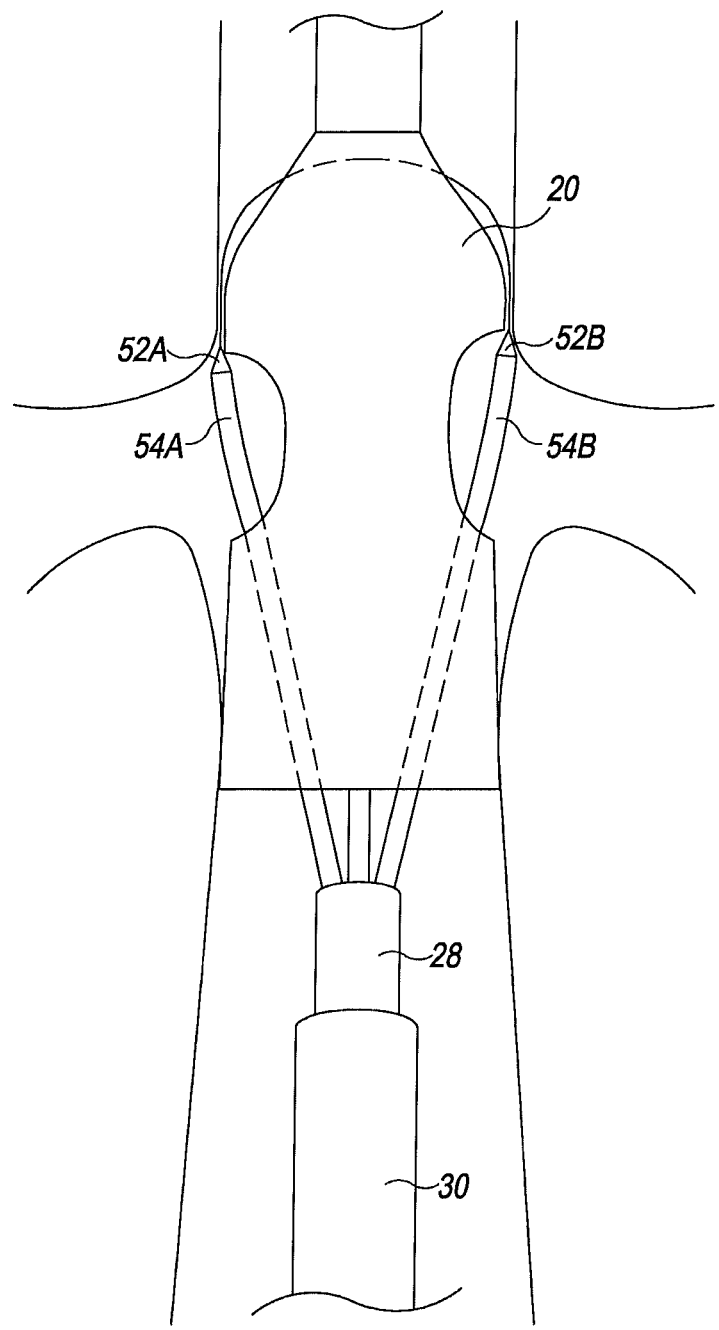
Figure 10:
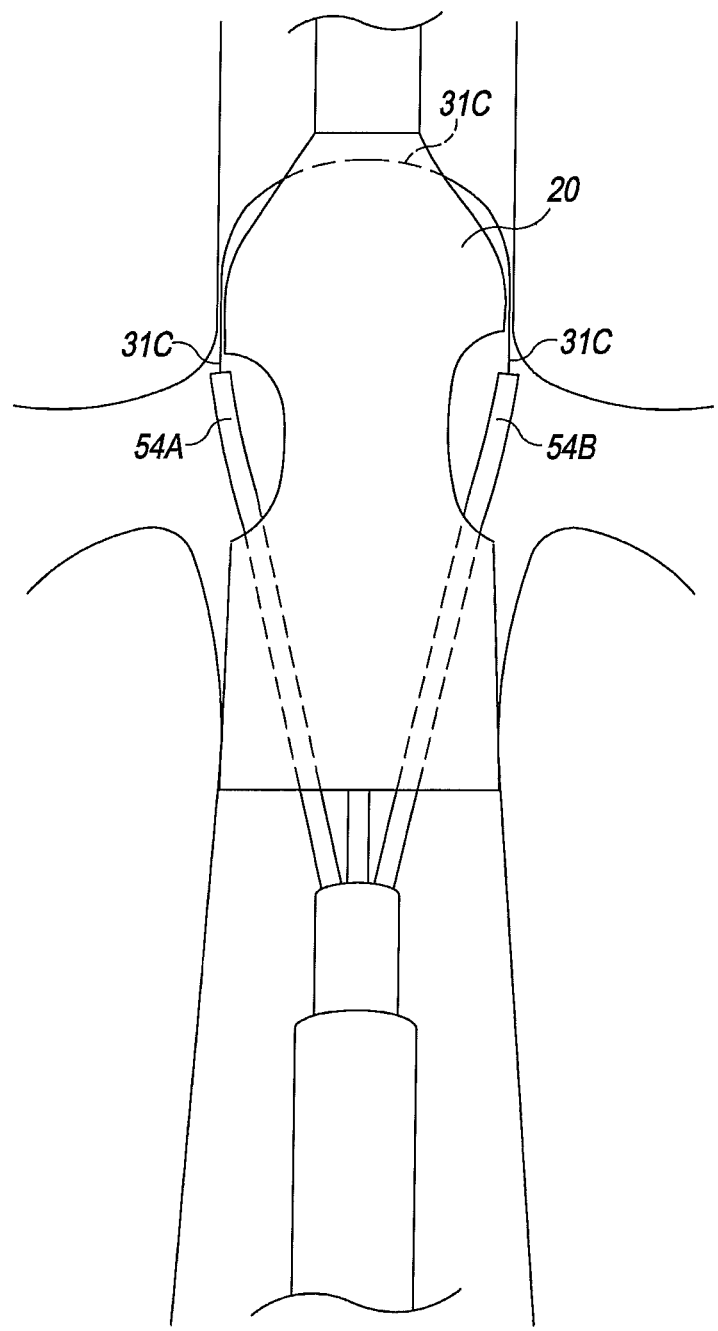

In FIG. 9, the auxiliary catheter 50A is advanced distally over the wire 31 within the lumen of the prosthesis 20 until the distal end of the sheath 54A passes through the fenestration 27A. Similarly, the auxiliary catheter 50B is advanced distally over the wire 31 within the lumen of the prosthesis 20 until the distal end of the sheath 54B passes through the fenestration 27B. In FIG. 10, the dilators 52A, 52B of the auxiliary catheters 50A, 50B have been removed by withdrawing them proximally through the sheaths 54A, 54B.

Figure 11:
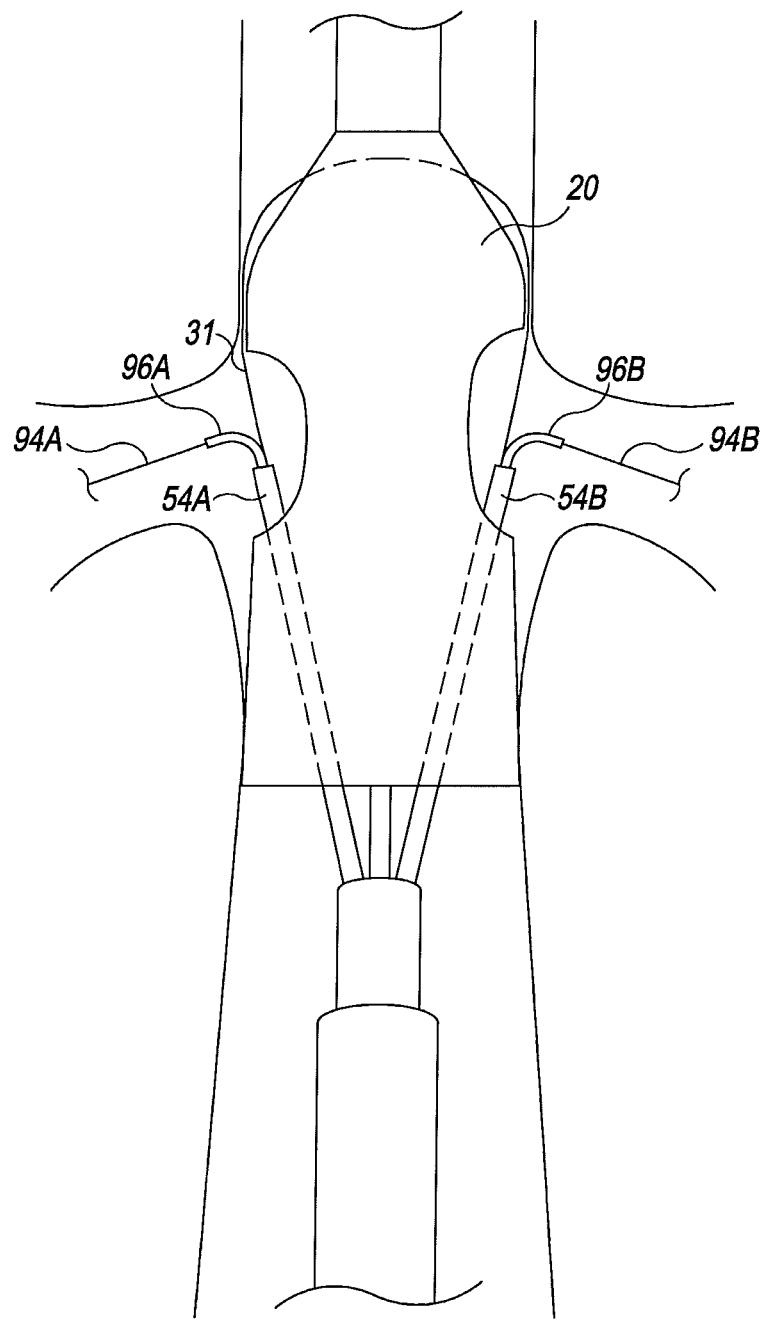

Next, branch guide wires 94A, 94B are provided for cannulating the branch vessels. As shown in FIG. 11, the branch guide wire 94A is delivered through the sheath 54A alongside a first end portion of the wire 31, and the branch guide wire 94B is delivered through the sheath 54B alongside a second end portion of the wire 31. Branch access catheters 96A, 96B are then introduced over the guide wires 94A, 94B, respectively. The access catheters 96A, 96B preferably have steerable distal end portions that can be used to guide the branch wires 94A, 94B through the fenestrations 27A, 27B and into respective branch vessels 92A, 92B. Suitable catheters are commercially available and include, for example, the Torcon NB® Advantage Catheters available from Cook Medical Incorporated, Bloomington Ind., USA.

Once the branch vessels are cannulated, the catheters 96A, 96B are removed by withdrawing them proximally through the sheaths 54A, 54B. At this point, the preloaded wire 31 is no longer needed and may be removed by pulling proximally on the first wire end 31A until the second wire end 31B exits the port 44A, or by pulling on the second wire end until the first wire end exits the port 44B.

Figure 12:
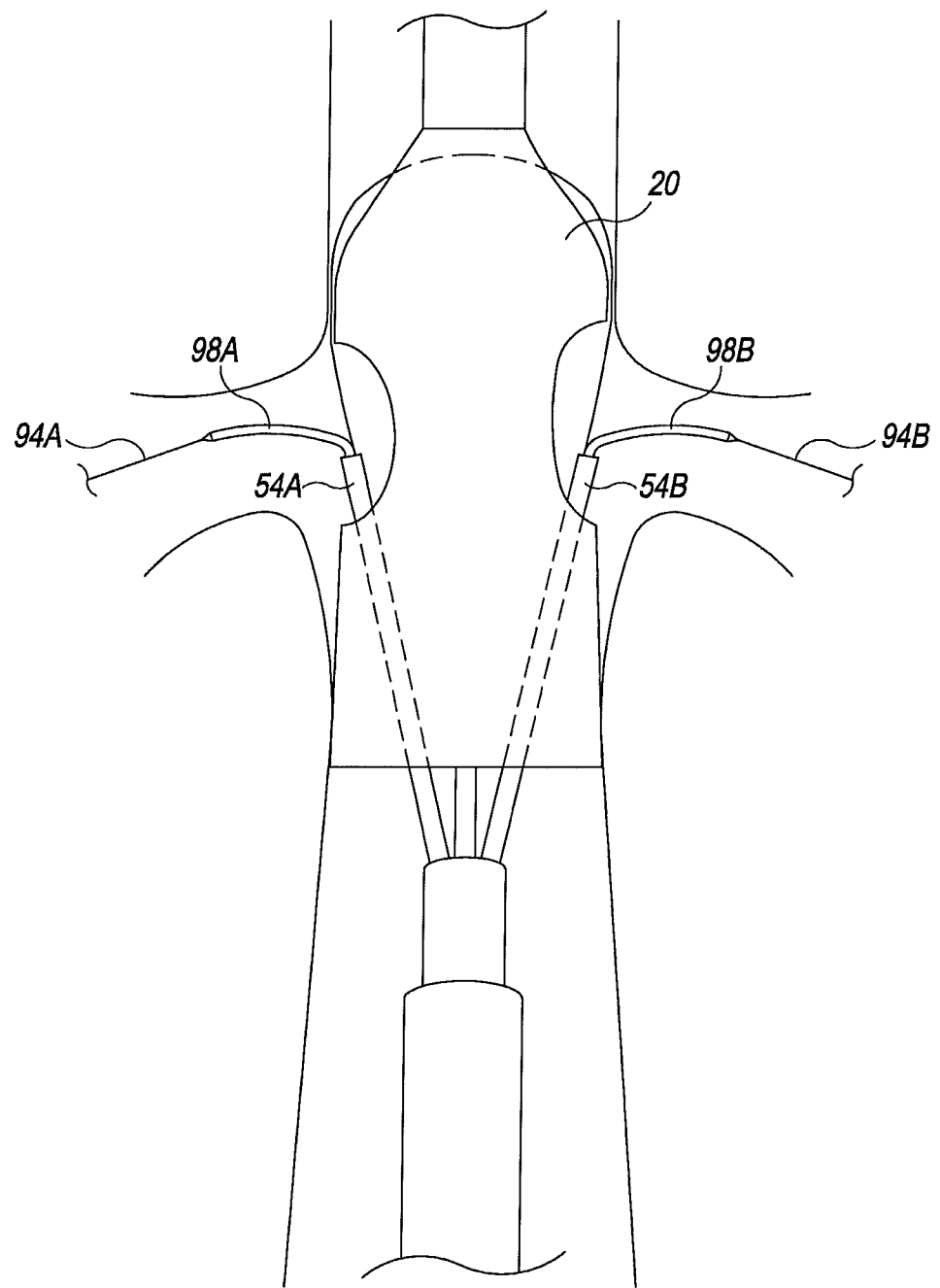

With the guide wires 94A, 94B in place, the operator may now deliver one or more interventional catheters 98A, 98B (including, for example, catheters carrying balloons, stents, grafts, imaging devices, and the like) into the branch vessels 92A, 92B through fenestrations 27A, 27B, as shown in FIG. 12.

FIG. 13 illustrates one example of a prosthesis 100. The prosthesis 100 may be configured as a stent graft. To that end, the prosthesis 100 may include a tubular body 101 of a biocompatible graft material. The tubular body 101 may be configured as a tubular main graft body of the prosthesis 100. The biocompatible graft material may form a sidewall of the tubular body 101. The prosthesis 100 may have a proximal end 102 and a distal end 103. The tubular body 101 may include a proximal end opening at the proximal end 102 and a distal end opening at the distal end 103. A lumen 104 may extend generally longitudinally within the prosthesis 100. The lumen 104 may extend from the proximal end opening to the distal end opening to permit passage of blood or other body fluid through the tubular body from the distal end to the proximal end.

An anterior side of the prosthesis 100 may extend circumferentially around approximately half of the circumference of the tubular body 101 of the prosthesis. A posterior side of the prosthesis 100 may extend circumferentially around approximately the other half of the circumference of the tubular body 101. The posterior side of the prosthesis 100 may be positioned opposite the anterior side with respect to the circumference of the prosthesis. In other words, a plane may be defined to include the longitudinal axis of the prosthesis 100. The anterior side of the prosthesis 100 may be positioned on one side of the plane, and the posterior side of the prosthesis may be positioned on the opposite side of the plane from the anterior side. The anterior side and the posterior side may cooperatively form the tubular body 101 of the prosthesis 100.

The prosthesis 100 may include one or more stents 105 (see FIG. 14) coupled to the graft material of the tubular body 101. The stents 105 may be conventional stents having any configuration known in the art. The stents 105 may be self-expanding or balloon expandable. Preferably, the stents 105 are self-expanding. The stents 105 may be coupled to an internal surface of the graft material and/or an external surface of the graft material. The prosthesis 100 may include an attachment mechanism such as an attachment stent 106 at either or both ends of the prosthesis. The attachment mechanism may aid in securing the prosthesis 100 within the body vessel to prevent migration of the prosthesis within the body vessel.

The prosthesis 100 may include one or more fenestrations or openings formed through the graft material of the prosthesis. For example, the prosthesis 100 may include one or more fenestrations formed in the sidewall of the tubular body 101. Any of the fenestrations described herein may be configured as any type of opening providing a fluid pathway through the graft material between the lumen 104 of the prosthesis 100 and a point external to the prosthesis. Additionally, or alternatively, any of the fenestrations described herein may be configured to receive a branch extension prosthesis to couple the prosthesis 100 to a branch vessel as further described below. Additionally, or alternatively, any of the fenestrations described herein may be in fluid communication with a branch extending from the tubular body 101 of the prosthesis 100 as further described below. Additionally, or alternatively, any of the fenestrations described herein may be pivotable or non-pivotable.

In one example, the prosthesis 100 may include a first fenestration 110, a second fenestration 120, a third fenestration 130, and a scallop 140 as shown in FIG. 13. The first and second fenestrations 110, 120 may be pivotable fenestrations, while the third fenestration 130 may be non-pivotable. Although the prosthesis 100 is generally described as including two pivotable fenestrations 110, 120 and a non-pivotable fenestration 130, the disclosure is not so limited. In other examples, any of the fenestrations may be pivotable or non-pivotable, and such examples are within the scope of this disclosure. The first and second fenestrations 110, 120 may be positioned on the prosthesis 100 to align with, for example, the renal arteries. It will be recognized by one of ordinary skill in the art that the prosthesis 100 may include any number of openings of any type. Also, the openings may be arranged on the prosthesis in any manner. Preferably, the openings may be arranged to correspond to a particular position within the anatomy into which the prosthesis is intended to be placed.

The prosthesis 100 illustrated in FIG. 13 may be configured for placement in an abdominal aorta of a patient. The prosthesis 100 may be configured to extend between a point proximal of the renal arteries and a point distal of the renal arteries. To that end, the scallop 140 may be configured to align with the celiac artery, the third fenestration 130 may be configured to align with the superior mesenteric artery, and the first and second fenestrations 110, 120 may be configured to align with the renal arteries. The scallop 140 may be positioned circumferentially on an anterior point of the prosthesis 100 and longitudinally near the distal end 103 of the prosthesis. The anterior point of the prosthesis 100 may extend generally longitudinally along the tubular body 101 of the prosthesis and may be substantially circumferentially centered on the anterior side of the prosthesis. The third fenestration 130 may be positioned circumferentially on the anterior point of the prosthesis 100 and longitudinally proximal of the scallop 140. The first and second fenestrations 110, 120 may be spaced from one another around the circumference of the prosthesis 100. For example the first fenestration 110 may be configured to align with the right renal artery and may be spaced a first circumferential distance from the anterior point of the prosthesis 100. The second fenestration 120 may be configured to align with the left renal artery and may be spaced a second circumferential distance from the anterior point of the prosthesis 100. The first and second circumferential distances may be of substantially equal lengths in opposite directions relative to the anterior point of the prosthesis 100. Alternatively, the first and second circumferential distances may be different from one another, for example, to correspond to the anatomy of a particular patient. The first and second fenestrations 110, 120 may be positioned at substantially the same longitudinal position along the tubular body 101 of the prosthesis 100. Alternatively, the first and second fenestrations 110, 120 may be offset longitudinally with respect to one another, for example, to correspond to the anatomy of a particular patient. The first and second fenestrations 110, 120 may be positioned longitudinally proximal of the third fenestration 130 and the scallop 140.

The lumen 104 of the prosthesis 100 may be in fluid communication with a point external to the prosthesis through each of the first and second fenestrations 110, 120. Each of the first and second fenestrations 110, 120 may be configured to receive a branch extension prosthesis to couple the prosthesis 100 to a branch vessel within the body of the patient. For example, the first fenestration 110 may be configured to receive a branch extension prosthesis to couple the prosthesis 100 to the left renal artery, and the second fenestration 120 may be configured to receive a branch extension prosthesis to couple the prosthesis to the right renal artery as further described below. In one example, the first and/or second fenestrations 110, 120 may be configured as pivotable fenestrations such as, for example, those described in U.S. Patent Application Publication No. 2012/0046728, which is incorporated by reference herein in its entirety. To that end, each of the first and second fenestrations 110, 120 may be configured to move or pivot relative to the tubular body 101 of the prosthesis 100 to account for any misalignment between the fenestration and the corresponding branch vessel.

Figure 14:
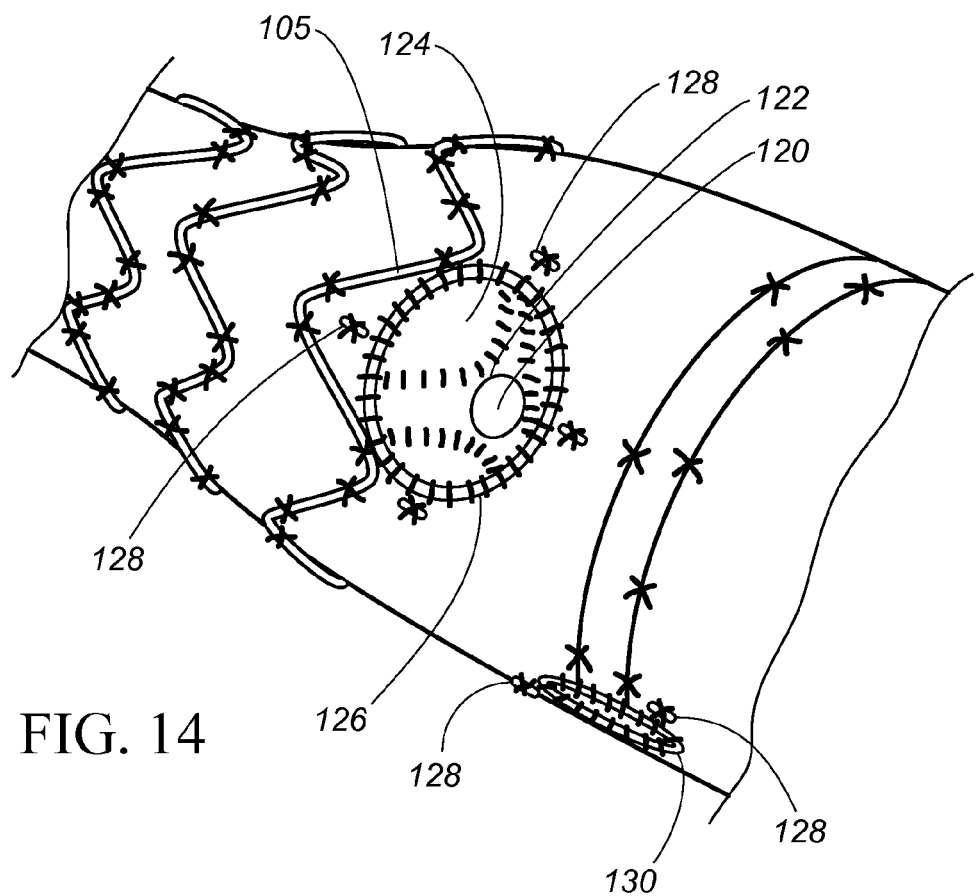
FIG. 14 illustrates a close up view of one example of a pivotable fenestration in a concave orientation.
Figure 15:
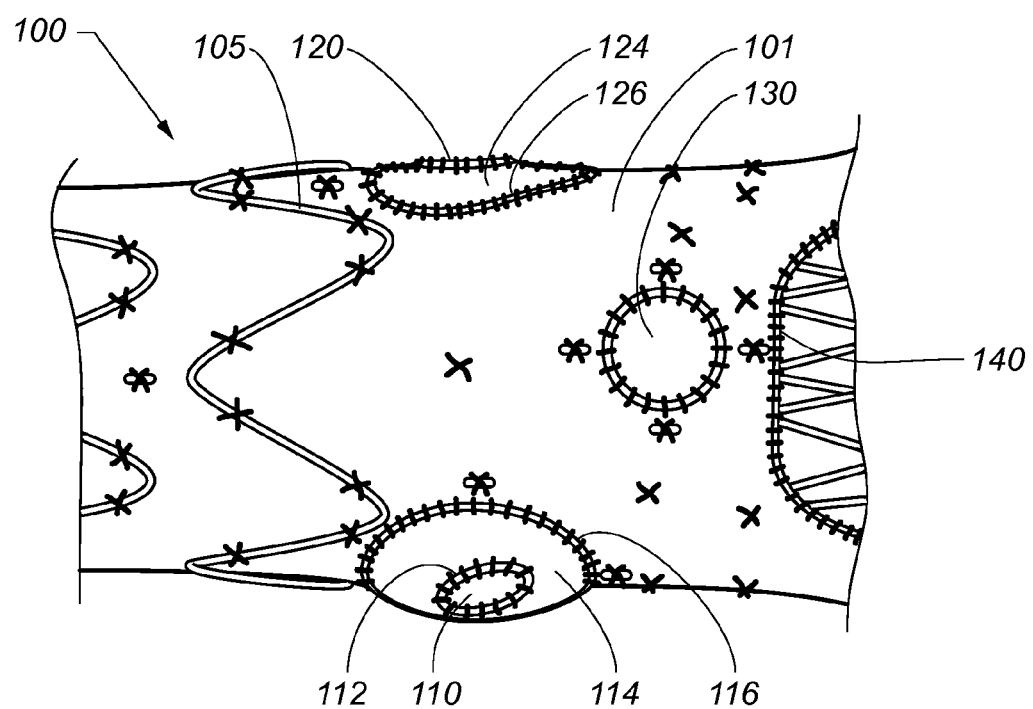
FIG. 15 illustrates a close up view of one example of a pivotable fenestration in a convex orientation.

FIG. 14 shows a close-up view of the second fenestration 120, which may be configured as a pivotable fenestration. In this example, the second fenestration 120 may include an inner perimeter 122 surrounding the fenestration 120, a band 124 surrounding the inner perimeter 122, and an outer perimeter 126 surrounding the band 124. The outer perimeter 126 may have a diameter that is greater than a diameter of the inner perimeter 122. The inner perimeter 122, the band 124, and the outer perimeter 126 may be substantially concentric with one another if brought into the same plane, for example, the surface plane of the tubular body 101. The band may have a first diameter that is substantially the same as the diameter of the inner perimeter 122 and a second diameter that is substantially the same as the diameter of the outer perimeter 126. The diameter of the band may decrease in a direction away from the exterior surface of the tubular body 101 from the outer perimeter 126 to the inner perimeter 122. In this manner, the inner perimeter 122, the band 124, and the outer perimeter 126 may form an extension having a protruding shape, resembling a dome, or a frustoconical cone extending from the surface of the tubular body 101. The second fenestration 120 may be positioned at the peak or top of the extension. The pivotable fenestration may be placed in a concave orientation or a convex orientation. In the concave orientation, the extension may extend into the lumen 104 of the prosthesis 100 as shown in FIGS. 13-14. In the convex orientation, the extension may extend away from the lumen 104 as shown in FIG. 15. The pivotable fenestration may be movable between the concave orientation and the convex orientation. Additionally, or alternatively, the pivotable fenestration may be placed in any position between the concave orientation and the convex orientation. For example, the band 124 may be folded, bent, gathered, pleated, or otherwise manipulated such that the second fenestration 120 is generally aligned with the surface plane of the prosthesis 100.

The outer perimeter 126 may be affixed to the graft material of the tubular body 101 by any attachment method including suturing circumferentially about an aperture disposed through the graft material. The band 124 may be sufficiently flexible to permit the second fenestration 120 to move such that a branch prosthesis disposed in the fenestration may be oriented upwardly, downwardly, laterally, diagonally, and the like relative to the surface of the tubular body 101 of the prosthesis 100. In some examples, the band 124 may permit the second fenestration 120 to move up to about 180 degrees relative to the surface plane of the prosthesis 100. Accordingly, the pivotable fenestration may enable the prosthesis 100 to be used in a variety of patients due to its ability to adapt to the variance in the positioning of the diseased branch vessels. For example, if a branch vessel is or becomes offset longitudinally or axially from the pivotable fenestration, the pivotable fenestration may pivot the branch prosthesis in the necessary direction and to the necessary degree to maintain the branch prosthesis in place in the branch vessel.

The first fenestration 110 may be configured as a pivotable fenestration as shown in FIG. 15. To that end, the first fenestration 110 may include an inner perimeter 112 surrounding the fenestration 110, a band 114 surrounding the inner perimeter 112, and an outer perimeter 116 surrounding the band 114. In this example, the first fenestration 110 may be configured generally as described above with reference to the second fenestration 120.

As shown throughout FIGS. 14-15, imageable markers 128 may be placed at various positions on the prosthesis 100 to identify certain aspects of the prosthesis and locations of those aspects during implantation of the prosthesis within the vasculature of a patient. The markers 128 may be viewed during and after placement of the prosthesis 100 to facilitate correct placement of the first, second, and/or third fenestrations 110, 120, 130, the scallop 140, the ends 102, 103 of the prosthesis, and the like. For example, as shown in FIG. 14, markers 128 may be placed about the circumference of the outer perimeter 126 of the pivotable fenestration. The markers 128 may be, for example, sewn or sutured to the graft material of the tubular body 101 or woven into the graft material. Additionally, or alternatively, the markers 128 may be placed on the struts of one or more stents 105. For example, radiopaque marker tubes may be placed about one or more struts of any of the stents. The markers 128 may be formed from any material that may be imaged by way of fluoroscopy, 3D imaging, MRI, or the like. For example, one suitable material may be gold.

The prosthesis 100 may be sized and shaped for placement within the vasculature of a patient as further described below. The preferred size and shape of the prosthesis 100 may depend on the anatomy in which it is to be implanted. Physiological variables, deployment characteristics, and other factors also may contribute to the determination of a proper size and shape of the prosthesis 100. For example, the prosthesis 100 may have a size and shape suitable for placement in the abdominal aorta. To that end, the tubular body 101 of the prosthesis 100 may have a diameter, for example, ranging from about 10 mm to about 38 mm, typically from about 19 mm to about 31 mm. The diameter of the tubular body 101 may be generally constant along the length thereof. Alternatively, the tubular body 101 may be tapered such that the diameter of the tubular body may generally increase or decrease along the length thereof. The first and second fenestrations 110, 120 may be configured to align with the renal arteries. Accordingly, the first and second fenestrations 110, 120 may have a diameter, for example, ranging from about 6 mm to about 24 mm, typically from about 6 mm to about 8 mm. The prosthesis 100 may be deployed in combination with various other prostheses to effectively bridge an aneurysmal portion of the vasculature.

The tubular body and the bands of the pivotable fenestrations may be made of any material known in the art. The tubular body may be made of the same or a different material as the bands of the pivotable fenestrations. Preferably, the tubular body and the bands may be formed from a biocompatible material that is substantially non-toxic in the in vivo environment of its intended use and substantially unrejected by the patient's physiological system (i.e., is non-antigenic). For example, the tubular body and/or the bands of the pivotable fenestrations may be made of an expanded polytetrafluoroethylene (ePTFE), polytetrafluoroethylene (PTFE), silicone, polyurethane, polyamide (nylon), polyethylene, polypropylene, polyaramids, polyacrylonitrile, cellulose, or another flexible biocompatible material. Additionally, or alternatively, the tubular body and/or the bands of the pivotable fenestrations may be made of known fabric graft materials, e.g., woven polyester such as DACRON® from Invista, Wichita, Kans., USA, polyetherurethanes such as THORALON® from Thoratec Corporation, Pleasanton, Calif., USA, or polyethylene such as an ultra-high molecular weight polyethylene (UHMwPE) such as DYNEEMA® from DSM Dyneema LLC, Stanley, N.C., USA. In addition, materials that are not inherently biocompatible may be subjected to surface modifications to render the materials biocompatible. Examples of surface modifications include, for example, graft polymerization of biocompatible polymers on the surface, coating of the surface with a crosslinked biocompatible polymer, chemical modification with biocompatible functional groups, or immobilization of a compatibilizing agent such as heparin or other biocompatible substances. Thus, any fibrous material having sufficient strength to survive in the in vivo environment may be used to form a textile graft, provided the final textile is biocompatible.

The tubular body and/or the bands of the pivotable fenestrations may include a bioremodelable material such as reconstituted or naturally-derived collagenous materials. Suitable remodelable materials may be provided by collagenous extracellular matrix (ECM) materials possessing biotropic properties. For example, suitable collagenous materials may include ECM materials such as those comprising submucosa, renal capsule membrane, dermal collagen, dura mater, pericardium, fascia lata, serosa, peritoneum or basement membrane layers, including liver basement membrane. Suitable submucosa materials for these purposes may include, for instance, intestinal submucosa including small intestinal submucosa, stomach submucosa, urinary bladder submucosa, and uterine submucosa. Collagenous matrices including submucosa (potentially along with other associated tissues) useful in the present invention can be obtained by harvesting such tissue sources and delaminating the submucosa-containing matrix from smooth muscle layers, mucosal layers, and/or other layers occurring in the tissue source. For additional information as to some of the materials useful in the present invention, and their isolation and treatment, reference can be made, for example, to U.S. Pat. Nos. 4,902,508, 5,554,389, 5,993,844, 6,206,931, and 6,099,567. Non-limiting examples of suitable remodelable materials may include SURGISIS® BIODESIGN™ from Cook Medical Incorporated, Bloomington, Ind., USA or the graft prosthesis material described in U.S. Pat. No. 6,206,931 to Cook et al., which is incorporated herein by reference in its entirety. The graft bodies also may be made of any of the materials described in U.S. Pat. No. 7,407,509 to Greenberg et al. or U.S. Patent Application Publication No. 2009/0171451 by Kuppurathanam et al., which are incorporated herein by reference in their entirety.

The stents described herein may have any suitable stent pattern known in the art. One example of a stent pattern is the Z-stent or Gianturco stent design. Each Z-stent may include a series of substantially straight segments or struts interconnected by a series of bent segments or bends. The bent segments may include acute bends or apices. The Z-stents are arranged in a zigzag configuration in which the straight segments are set at angles relative to one another and are connected by the bent segments. This design provides both significant radial force as well as longitudinal support. In tortuous anatomy, branches, or fenestrations, it may be preferable to use alternative stents or modifications to the Z-stent design to avoid stent-to-stent contact. Alternative stents may include, for example, annular or helical stents. Furthermore, in complex anatomical situations, external stents may have the potential to become intertwined with the wires or other devices utilized to ensure branch vessel access, sealing, and fixation. Thus, in some instances, it may be desirable to affix some of the stents to the internal surface of the prosthesis. The stents may be balloon expandable. Preferably, the stents may be self-expandable. The stents can maintain the patency of the prosthesis and ensure adequate sealing against the surrounding vascular tissue. Stent amplitude, spacing, and stagger may be adjusted for each prosthesis design. Any of the stents mentioned herein may include barbs and/or other anchoring members to help reduce the potential for prosthesis migration.

The stents described herein may be made from any suitable material known in the art. In one example, the stents may be made from standard medical grade stainless steel and soldered using silver standard solder (0 lead/0 tin). In other examples, the stents may be made from a metallic material including any type of stainless steel, silver, platinum, palladium, gold, titanium, tantalum, iridium, tungsten, cobalt, chromium, cobalt-chromium alloy 1058, cobalt-based 35N alloy, nickel-based alloy 625, a molybdenum alloy, a molybdenum alloy including about 0.4% to about 0.8% of lanthanum oxide ($La_2O_3$), and a nickel-titanium alloy, or other suitable materials known in the art. Additionally, or alternatively, the stents may be made from nitinol or other shape-memory metal. Moreover, the stents may be configured in a variety of ways to provide a suitable intraluminal support structure. For example, one or more stents may be made from a woven wire structure, a laser-cut cannula, individual interconnected rings, or another pattern or design.

Returning to FIG. 13, the prosthesis 100 may be provided as part of a preloaded system that includes a guide wire 150. The guide wire 150 may enable delivery of one or more branch extension prostheses as further described below. In some examples, a single guide wire may enable delivery of a branch extension prosthesis into multiple openings in the prosthesis.

FIG. 13 illustrates one example of the guide wire 150 received within the prosthesis 100 in a preloaded configuration. The guide wire 150 may include a first end segment 152 positioned at a first end of the guide wire and a second end segment 154 positioned at a second end of the guide wire opposite the first end. The guide wire 150 also may include a body portion or intermediate segment 156 positioned between the first end segment 152 and the second end segment 154. The first end segment 152 of the guide wire 150 may extend distally from a proximal end of a delivery device (e.g., the delivery catheter 1 described above). The first end segment 152 may enter the lumen 104 through the proximal end 102 of the prosthesis 100. The first end segment 152 may extend distally within the lumen 104 and exit the tubular body 101 of the prosthesis 100 through the first fenestration 110.

The intermediate segment 156 of the guide wire 150 may extend distally from the first end segment 152 and external of the tubular body 101 of the prosthesis 100. The intermediate segment 156 may reenter the tubular body 101 of the prosthesis 100 through a first guide wire opening 160. The first guide wire opening 160 may be configured as an opening through the graft material of the tubular body 101. The first guide wire opening 160 may be aligned with the first fenestration 110 with respect to the circumference of the prosthesis 100 and positioned distal of the third fenestration 130 with respect to the longitudinal axis of the prosthesis as shown in FIG. 13. In other examples, the first guide wire opening 160 may be positioned at any suitable location on the tubular body 101 of the prosthesis 100. The lumen 104 of the prosthesis 100 may be in fluid communication with a point external of the prosthesis through the first guide wire opening 160.

A portion of the intermediate segment 156 of the guide wire 150 may be disposed within the lumen 104 of the prosthesis 100 and extend between the first guide wire opening 160 and a second guide wire opening 162. The second guide wire opening 162 may be configured generally as described above with respect to the first guide wire opening 160. The second guide wire opening 162 may be aligned with the second fenestration 120 with respect to the circumference of the prosthesis 100 and positioned distal of the third fenestration 130 with respect to the longitudinal axis of the prosthesis. The portion of the intermediate segment 156 positioned between the first guide wire opening 160 and the second guide wire opening 162 may be substantially U-shaped. The opening of the U-shaped portion of the intermediate segment 156 may face proximally as shown in FIG. 13. One leg of the U-shaped portion of the intermediate segment 156 may extend distally from the first guide wire opening 160, and the other leg may extend proximally to the second guide wire opening 162. The curved portion of the U-shaped portion of the intermediate segment 156 between the two legs may be positioned distal of the third fenestration 130 with respect to the longitudinal axis of the prosthesis 100. In one example, the curved portion of the U-shaped portion of the intermediate segment 156 may overlap with the scallop 140 as shown in FIG. 13.

The intermediate segment 156 of the guide wire 150 may exit the lumen 104 of the prosthesis 100 through the second guide wire opening 162 and extend proximally external of the tubular body 101 of the prosthesis 100. The second end segment 154 of the guide wire 150 may extend proximally from the intermediate segment 156 and enter the tubular body 101 of the prosthesis 100 through the second fenestration 120. The second end segment 154 of the guide wire 150 may extend proximally within the lumen 104 and exit the lumen 104 through the proximal end 102 of the prosthesis 100. The second end segment 154 of the guide wire 150 may extend proximally to the proximal end of the delivery device. The first end segment 152 of the guide wire 150 may enable introduction of a branch prosthesis into the first fenestration 110 to couple the prosthesis 100 to the left renal artery, and the second end segment 154 of the guide wire 150 may enable introduction of a branch extension prosthesis into the second fenestration 120 to couple the prosthesis to the right renal artery.

FIGS. 16-17 illustrate another example of an endoluminal prosthesis 200. The prosthesis 200 may be configured as a stent graft and may be similar to the prosthesis 100 except for the differences described below. For example, the prosthesis 200 may include a tubular body 201 of a biocompatible graft material. The prosthesis 200 may have a proximal end 202, a distal end 203, and a lumen 204 extending generally longitudinally within the prosthesis to permit passage of blood or other body fluid from the distal end to the proximal end. The prosthesis 200 may have an anterior side extending circumferentially around approximately half of the circumference of the tubular body 201 and a posterior side positioned opposite the anterior side with respect to the circumference of the prosthesis. The anterior side and the posterior side may cooperatively form the tubular body 201 of the prosthesis 200.

The prosthesis 200 may include one or more stents (not shown) coupled to the graft material. The stents may be conventional stents having any configuration known in the art as described above with respect to the stents 105 of the prosthesis 100. The prosthesis 200 may include an attachment mechanism such as an attachment stent at either or both ends of the prosthesis as described above with respect to the attachment mechanism 106 of the prosthesis 100.

The prosthesis 200 may include a first fenestration 210 and a second fenestration 220. The first and second fenestrations 210, 220 may be pivotable fenestrations as described above with reference to the first and second fenestrations 110, 120 of the prosthesis 100. Although the prosthesis 200 is generally described as including two pivotable fenestrations 210, 220, this disclosure is not so limited. In other examples, any of the fenestrations may be pivotable or non-pivotable, and such examples are within the scope of this disclosure. The first and second fenestrations 210, 220 may be positioned on the prosthesis 200 to align with, for example, the renal arteries.

The prosthesis 200 may include a third fenestration 230, and a fourth fenestration 240, as shown in FIGS. 16-17. Each of the third fenestration 230 and the fourth fenestration 240 may be configured as a branch. In other words, the prosthesis 200 may include a first branch 231 extending outward from the tubular body 201 and in fluid communication with the third fenestration 230 and a second branch 241 extending outward from the tubular body 201 and in fluid communication with the fourth fenestration 240. Although the prosthesis 200 is generally described as having four fenestrations 210, 220, 230, 240, two of which are configured as branches 231, 241, this disclosure is not so limited. It will be recognized by one of ordinary skill in the art that the prosthesis 200 may include any number of openings of any type. For example, the first branch and/or the second branch may be omitted. Additionally, or alternatively, the openings may be arranged on the prosthesis in any manner. Preferably, the openings may be arranged to correspond to a particular position within the anatomy into which the prosthesis is intended to be placed.

The prosthesis 200 illustrated in FIGS. 16-17 may be configured for placement in an abdominal aorta of a patient. Additionally, or alternatively, the prosthesis 200 may be configured to extend between a point distal of the renal arteries and a point proximal of the renal arteries. To that end, the first branch 231 may be configured to align with the celiac artery, the second branch 241 may be configured to align with the superior mesenteric artery, and the first and second fenestrations 210, 220 may be configured to align with the renal arteries.

The first branch 231 may include a first end 232 adjacent to the third fenestration 230, a second end 233, and a lumen 234 extending generally longitudinally between the first and second ends of the first branch. The first end 232 of the first branch 231 may be attached to the tubular body 201 of the prosthesis 200 in any conventional manner. In one example, the first end 232 of the first branch 231 may be sutured to the graft material of the tubular body 201. In another example, the first branch 231 and the tubular body 201 may be formed as a unitary piece of graft material. The lumen 204 of the tubular body 201 may be in fluid communication with a point external to the prosthesis 200 through the lumen 234 of the first branch 231. The second branch 241 may include a first end 241 adjacent to the fourth fenestration 240, a second end 243, and a lumen 244 extending generally longitudinally between the first and second ends of the second branch. The first end 242 of the second branch 241 may be attached to the tubular body 201 as described above with reference to the first branch 231. The lumen 204 of the tubular body 201 may be in fluid communication with a point external to the prosthesis 200 through the lumen 244 of the second branch 241.

The first ends 232, 242 of the first and second branches 231, 241, respectively, may be spaced from one another around the circumference of the tubular body 201 of the prosthesis 200. In one example, the first ends 232, 242 of the first and second branches 231, 241, respectively, may be disposed between about 0 and about 310 degrees apart relative to one another, and more preferably, about 30 degrees apart. Additionally, or alternatively, the first ends 232, 242 of the first and second branches 231, 241, respectively, may be disposed at a predetermined distance from one another along the longitudinal axis of the tubular body 201 of the prosthesis 200. The first end 232 may be distal of the first end 242 as shown in FIGS. 16-17, or vice versa. Alternatively, the first ends 232, 242 may be disposed in close proximity to one another along the longitudinal axis of the tubular body 201.

Each of the first and second branches 231, 241 may be configured to receive a branch extension prosthesis to couple the branch to a branch vessel within the body of the patient. For example, the first branch 231 may be configured to receive a branch extension prosthesis to couple the first branch to the celiac artery, and the second branch 241 may be configured to receive a branch extension prosthesis to couple the second branch to the superior mesenteric artery, as further described below. The first branch 231 and/or the second branch 241 may extend outward away from the tubular body 201 of the prosthesis 200. The first branch 231 and/or the second branch 241 may extend proximally with respect to the tubular body 201 as shown in FIGS. 16-17. In other examples, the first branch 231 and/or the second branch 241 may extend distally with respect to the tubular body 201. Alternatively, or additionally, the first branch 231 and/or the second branch 241 may extend at least partially circumferentially around the tubular body 201. In other words, the first branch 231 and/or the second branch 241 may include a helical shape. Such a helical shape may facilitate insertion of a component such as a branch extension prosthesis into the first branch 231 and/or the second branch 241. Such a helical shape also may reduce torsion imposed by blood flow at the juncture between the prosthesis 200 and the branch vessels. Various exemplary helical branches that extend from a main body of a prosthesis, which may be used in conjunction with the present embodiments, are provided in U.S. Pat. No. 7,407,509 to Greenberg et al., which is incorporated by reference herein in its entirety.

The first and second fenestrations 210, 220 may be spaced from one another around the circumference of the prosthesis 200. For example the first fenestration 210 may be configured to align with the left renal artery and may be spaced a first circumferential distance from the anterior point of the prosthesis 200. The second fenestration 220 may be configured to align with the right renal artery and may be spaced a second circumferential distance from the anterior point of the prosthesis 200. The first and second circumferential distances may be of substantially equal lengths in opposite directions relative to the anterior point of the prosthesis 200. Alternatively, the first and second circumferential distances may be different from one another, for example, to correspond to the anatomy of a particular patient. In one example, the first and second fenestrations 210, 220 may be disposed between about 50 and about 310 degrees apart relative to one another, and more preferably, about 150 degrees apart. The first and second fenestrations 210, 220 may be positioned at substantially the same longitudinal position along the tubular body 201 of the prosthesis 200. Alternatively, the first and second fenestrations 210, 220 may be offset longitudinally with respect to one another, for example, to correspond to the anatomy of a particular patient. Additionally, or alternatively, the first and second fenestrations 210, 220 may be positioned longitudinally proximal of the first branch 231 and the second branch 241.

The prosthesis 200 may be provided as part of a preloaded system that includes the guide wire 150. FIG. 16 illustrates one example of the guide wire 150 received within the prosthesis 200 in a preloaded configuration. The first end segment 152 of the guide wire 150 may extend distally from the proximal end of the delivery device. The first end segment 152 may enter the lumen 204 through the proximal end 202 of the prosthesis 200. The first end segment 152 may extend distally within the lumen 204 and exit the tubular body 201 of the prosthesis 200 through the first fenestration 210. The intermediate segment 156 of the guide wire 150 may extend distally external of the tubular body 201 and reenter the lumen 204 of the prosthesis 200 through a first guide wire opening 260. The first guide wire opening 260 may be configured generally as described above with reference to the first guide wire opening 160 of the prosthesis 100. The first guide wire opening 260 may be aligned with the first fenestration 210 with respect to the circumference of the prosthesis 200 and positioned proximal of the first and second branches 231, 241 with respect to the longitudinal axis of the prosthesis as shown in FIG. 16. In other examples, the first guide wire opening 260 may be positioned at any suitable location on the tubular body 201 of the prosthesis 200. The lumen 204 of the prosthesis 200 may be in fluid communication with a point external of the prosthesis through the first guide wire opening 260.

A portion of the intermediate segment 156 of the guide wire 150 may be disposed within the lumen 204 of the prosthesis 200 and extend between the first guide wire opening 260 and a second guide wire opening 262. The second guide wire opening 262 may be configured generally as described above with reference to the first guide wire opening 160 of the prosthesis 100. The second guide wire opening 262 may be aligned with the second fenestration 220 with respect to the circumference of the prosthesis 200 and positioned proximal of the first and second branches 231, 241 with respect to the longitudinal axis of the prosthesis.

The intermediate segment 156 of the guide wire 150 may exit the lumen 204 of the prosthesis 200 through the second guide wire opening 262 and extend proximally external of the tubular body 201 of the prosthesis 200. The second end segment 154 of the guide wire 150 may enter the tubular body 201 of the prosthesis 200 through the second fenestration 220. The second end segment 154 of the guide wire 150 may extend proximally within the lumen 204 and exit the lumen 204 through the proximal end 202 of the prosthesis 200. The second end segment 154 of the guide wire 150 may extend proximally to the proximal end of the delivery device. The first end segment 152 of the guide wire 150 may enable introduction of a branch prosthesis into the first fenestration 210 to couple the prosthesis 200 to the left renal artery, and the second end segment 154 of the guide wire 150 may enable introduction of a branch extension prosthesis into the second fenestration 220 to couple the prosthesis to the right renal artery. Additionally, or alternatively, the guide wire 150 may be positioned such that no portion of the guide wire extends distally beyond the distal end 203 of the prosthesis 200.

In each of the examples illustrated in FIGS. 13 and 16, the guide wire 150 may extend through a guide wire opening (e.g., the first and second guide wire openings 160, 162 of the prosthesis 100 or the first and second guide wire openings 260, 262 of the prosthesis 200). When the guide wire 150 is removed following deployment of the prosthesis within a body vessel, the guide wire openings may remain as holes in the graft material of the prosthesis. If the holes are positioned within an aneurysmal portion 669 (or another damaged portion) of the body vessel, as shown in FIG. 16, blood or other body fluid may leak through the holes in the graft material and into the aneurysmal portion of the body vessel. In other words, the guide wire openings in the prosthesis may lead to an endoleak into the aneurysmal portion 669 of the body vessel. Such leakage may cause further damage to the body vessel. Thus, it may be desirable to provide a prosthesis that is free of guide wire openings. In other words, it may be desirable to provide a guide wire in a preloaded configuration in which the guide wire does not extend through guide wire openings in the tubular body of the prosthesis.

FIG. 17 illustrates another example of the guide wire 150 received within the prosthesis 200 in a preloaded configuration. In this example, the prosthesis 200 may be substantially free of guide wire openings. In other words, the prosthesis 200 may not include the first and second guide wire openings 260, 262 as described above with reference to FIG. 16. The first end segment 152 of the guide wire 150 may extend distally from the proximal end of the delivery device. The first end segment 152 may enter the lumen 204 through the proximal end 202 of the prosthesis 200. The first end segment 152 may extend distally within the lumen 204 and exit the tubular body 201 of the prosthesis 200 through the first fenestration 210.

The intermediate segment 156 of the guide wire 150 may extend between the first fenestration 210 and the second fenestration 220 of the prosthesis 200. The intermediate segment 156 may be disposed on the exterior surface of the tubular body 201 of the prosthesis 200. The intermediate segment 156 may be substantially U-shaped with the opening of the U-shaped intermediate segment facing proximally as shown in FIG. 17. One leg of the U-shaped intermediate segment 156 may extend distally from the first fenestration 210, and the other leg may extend proximally to the second fenestration 220. The curved portion of the U-shaped intermediate segment 156 may be positioned longitudinally proximal of the first and second branches 231, 241 as shown in FIG. 17. In this manner, the intermediate segment 156 may extend at least partially circumferentially around the exterior surface of the tubular body 201 of the prosthesis 200. The curve of the U-shaped intermediate segment 156 may be positioned between the first and second fenestrations 210, 220 and the first and second branches 230, 240 with respect to the longitudinal axis of the prosthesis 200. In other words, the intermediate segment 156 of the guide wire 150 may be positioned just distal of the first and second fenestrations 210, 220 of the prosthesis 200 as shown in FIG. 17. In other examples, the curved portion of the U-shaped intermediate segment 156 may be positioned longitudinally at any suitable position on the tubular body 201 of the prosthesis 200. For example, the legs of the U-shaped intermediate segment 156 may have a sufficient length such that the curved portion may be positioned distal of the first and/or second branches 231, 241.

The second end segment 154 of the guide wire 150 may enter the tubular body 201 of the prosthesis 200 through the second fenestration 220. The second end segment 154 may extend proximally within the lumen 204 and exit the lumen 204 through the proximal end 202 of the prosthesis 200. The second end segment 154 of the guide wire 150 may extend proximally to the proximal end of the delivery device. The first end segment 152 of the guide wire 150 may enable introduction of a branch prosthesis into the first fenestration 210 to couple the prosthesis 200 to the left renal artery, and the second end segment 154 of the guide wire 150 may enable introduction of a branch prosthesis into the second fenestration 220 to couple the prosthesis to the right renal artery. Additionally, or alternatively, the guide wire 150 may be positioned such that no portion of the guide wire extends distally beyond the distal end 203 of the prosthesis 200.

The intermediate segment 156 of the guide wire 150 may extend at least partially circumferentially around the anterior side of the prosthesis, the posterior side of the prosthesis, or both the anterior and posterior sides of the prosthesis. Preferably, the intermediate segment 156 of the guide wire 150 may be disposed on the anterior side of the prosthesis between the first and second fenestrations 210, 220 as shown in FIG. 17. This configuration may reduce the length of the guide wire 150 which may be disposed on the exterior surface of the tubular body 201 of the prosthesis 200. Such a reduced length of the guide wire 150 which may be exposed outside of the prosthesis 200 may reduce the potential of catching or snagging the guide wire 150 on components of the delivery system which may be used to deploy the prosthesis within the body vessel. Such a reduced length also may enable a physician to control the diameter of the prosthesis 200 (e.g., by applying tension to the guide wire 150) as further described below. Additionally, or alternatively, this configuration may enable adjustment of the circumferential positions of the first and second fenestrations 210, 220 also as further described below.

The intermediate segment 156 of the guide wire 150 may be attached to the tubular body 201 of the prosthesis 200. The intermediate segment 156 may be attached to the prosthesis 200 using any suitable attachment mechanism. For example, the intermediate segment 156 may be releasably attached to the exterior surface of the tubular body 201 by one or more sutures 158 as shown in FIG. 17. The sutures 158 may be stitched into the graft material of the tubular body 201 of the prosthesis 200, and the guide wire 150 may be received between each suture and the exterior surface of the tubular body. In this example, the guide wire 150 may be removed from the prosthesis 200 by sliding the guide wire out of engagement with the sutures 158. In another example, the intermediate segment 156 of the guide wire 150 may be stitched in and out of the graft material of the tubular body 201. In yet another example, the intermediate segment 156 may be attached to the exterior surface of the prosthesis 200 by a releasable adhesive. In another example, the intermediate segment 156 may be received within a pocket, which may be attached to the exterior surface of the prosthesis 200. The pocket may include a piece of graft material that is folded or rolled to create an interior passage to receive the intermediate segment 156. The pocket may be integral with or separate from the tubular body 201 of the prosthesis 200. Alternatively, or additionally, the pocket may include a tube or catheter, which may be attached to the exterior surface of the graft material. The pocket may be positioned radially between the graft material of the tubular body 201 and an external stent of the prosthesis 200. In other words, the pocket may be sandwiched between the graft material and the stent. Alternatively, or additionally, the stent may include an aperture configured to receive the pocket and/or the intermediate segment 156 of the guide wire 150.

FIGS. 18-24 illustrate a method of using the prosthesis 200 of FIG. 17 to treat a condition (e.g., an aneurysm) in the area of an abdominal aorta and/or branch vessels of a patient. In a first step, the prosthesis 200 may be provided with the guide wire 150 coupled to the prosthesis in the preloaded configuration as shown in FIG. 17. The prosthesis 200 may be compressed into a delivery state and delivered into an abdominal aorta 660 of a patient using any suitable deployment system or introducer (e.g., the delivery catheter 1 described above with reference to FIGS. 1-12). Additionally, or alternatively, an introducer such as that described in International Patent Application Publication No. WO98/53761, entitled "A Prosthesis and a Method and Means of Deploying a Prosthesis," which is incorporated herein by reference in its entirety, may be used to deploy the prosthesis 200. WO98/53761 describes a deployment system for an endoluminal prosthesis whereby the prosthesis may be radially compressed onto a delivery catheter and covered by an outer sheath. To deploy the prosthesis, the operator may slide or retract the outer sheath over the delivery catheter, thereby exposing the prosthesis. The prosthesis may expand outwardly upon removal of the sheath. The operator may directly manipulate the sheath and the delivery catheter, which may provide the operator with a relatively high degree of control during the procedure. Further, such delivery devices may be compact and may have a relatively uniform, low-diameter radial profile, which may enable atraumatic access and delivery.

Figure 18:
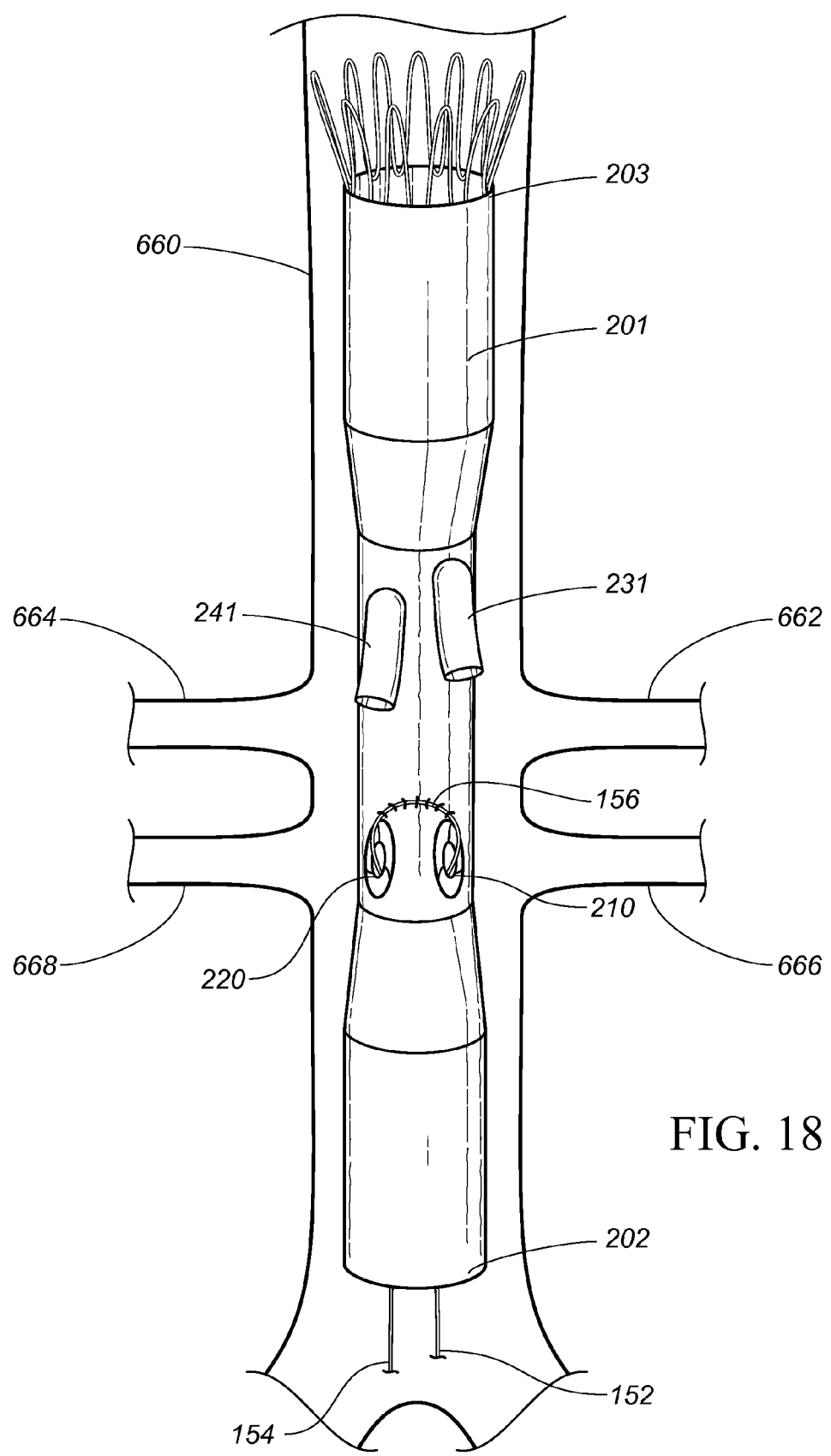
FIG. 18 illustrates the prosthesis of FIG. 17 deployed within an abdominal aorta of a patient.

Using a suitable introducer, a physician may obtain access to the abdominal aorta 660 via a femoral cut-down with the prosthesis 200 in the compressed state. The prosthesis 200 may be positioned within the abdominal aorta 660 in the compressed state, for example, using the radiopaque markers 128, such that the first and second branches 231, 241 may be generally aligned in the vicinity of the ostia of the celiac artery 662 and the superior mesenteric artery 664, respectively, as shown in FIG. 18. Additionally, the first and second fenestrations 210, 220 may be generally aligned in the vicinity of the ostia of the left renal artery 666 and the right renal artery 668, respectively, as shown in FIG. 18. At this time, the sheath of the introducer that constrains the prosthesis 200 may be retracted proximally relative to the delivery catheter to enable the prosthesis to expand to the deployed configuration shown in FIG. 18.

It should be noted that, in FIGS. 18-24, outer surfaces of the prosthesis 200 are shown as being spaced from inner surfaces of the abdominal aorta 660 solely for illustrative purposes. In use, the prosthesis 200 may be sized and configured so that at least a portion of the outer surface of the tubular body 201 securely engages at least a portion of the inner surface of the abdominal aorta 660 to hold the prosthesis 200 in place relative to the vasculature. Optionally, additional modular prostheses may be coupled to the prosthesis 200 (e.g., extending into one or more of the iliac arteries), and the modular prostheses may include outer surfaces dimensioned to securely engage inner surfaces of the iliac arteries or other vasculature.

With the prosthesis 200 positioned within the abdominal aorta 660, tension may be applied to the guide wire 150 to manipulate the prosthesis 200. For example, tension may be applied to the first end segment 152 and/or the second end segment 154 of the guide wire from the proximal end of the introducer. This may cause a reduction in the circumference of a portion of the tubular body 201 of the prosthesis 200 near the intermediate segment 156 of the guide wire 150 and/or the first and second fenestrations 210, 220. In other words, the tension on the guide wire 150 may cause the graft material of the tubular body 201 to be gathered, bunched, pleated, or otherwise manipulated such that a portion of the tubular body may at least partially collapse. This may create space between the prosthesis 200 and the inner surface of the abdominal aorta 660, which may enable further manipulation or positioning of the prosthesis 200 within the body vessel. With the intermediate segment 156 of the guide wire 150 positioned on the anterior side of the prosthesis 200, as shown in FIG. 18, such tension also may cause the fenestrations 210, 220 to be pulled closer to one another along the circumference of the prosthesis 200 in an anterior direction. This may aid the physician in aligning the first and second fenestrations 210, 220 with the left and right renal arteries 666, 668, respectively, which may be positioned on an anterior portion of the abdominal aorta 660. In other examples, the intermediate segment 156 may be positioned on the posterior side of the prosthesis 200. In these examples, tension on the guide wire 150 may cause the fenestrations 210, 220 to be pulled closer to one another along the circumference of the prosthesis 200 in a posterior direction.

Figure 19:
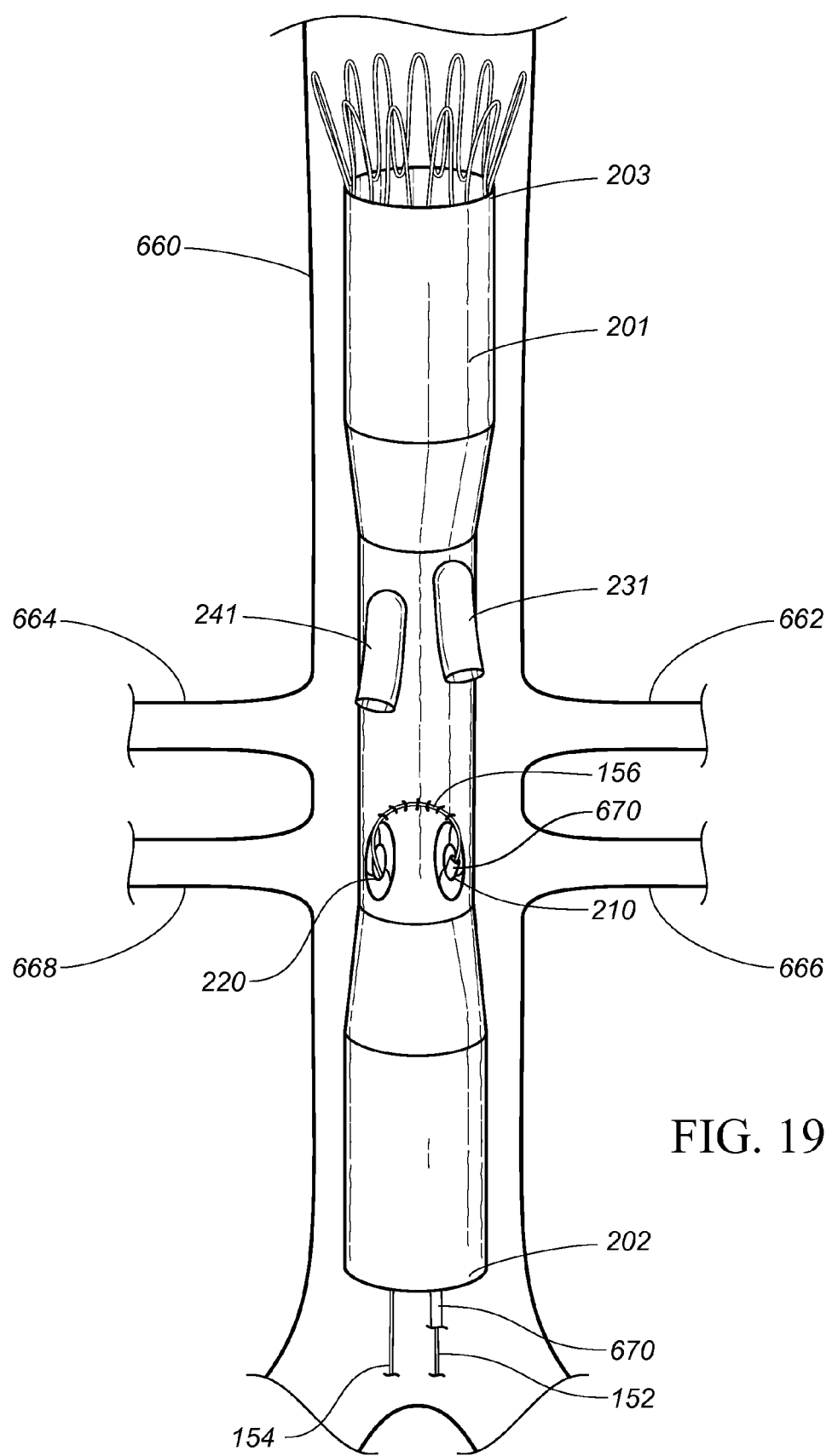
FIG. 19 illustrates one example of a sheath introduced over a segment of the guide wire and into a fenestration of the prosthesis shown in FIG. 18.
Figure 20:
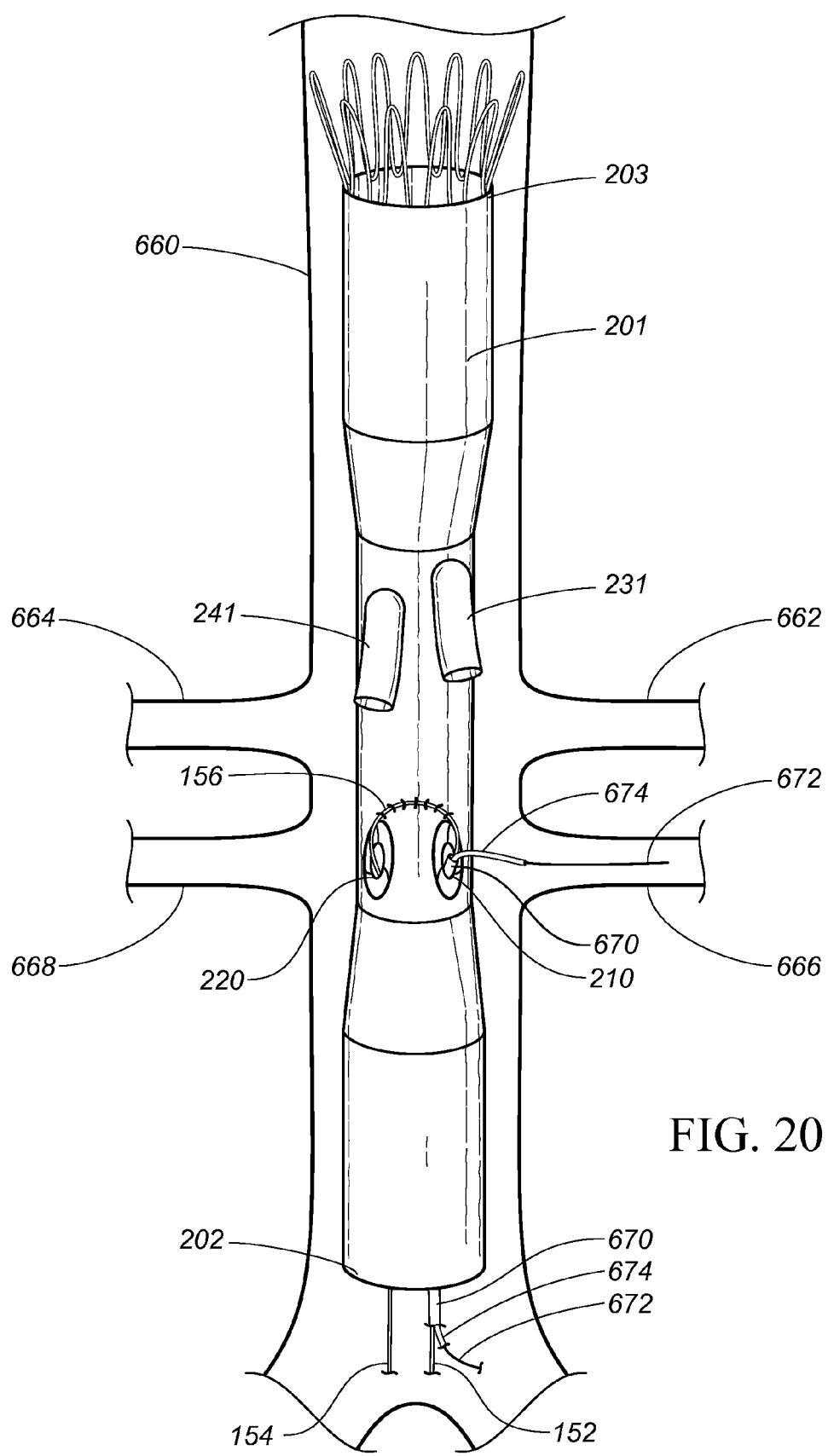
FIGS. 20-21 illustrate one example of a catheter and a wire guide introduced within the sheath shown in FIG. 19 and into a renal artery.

In a next step, a sheath may be guided over the first end segment 152 of the guide wire 150 and through the first fenestration 210. For example, a sheath 670 may be advanced over the first end segment 152 of the guide wire 150 in a distal direction as shown in FIG. 19. The sheath 670 may be configured as described above with reference to the catheters 50A, 50B. To that end, the sheath 670 may include a sheath and a dilator as shown in FIG. 2. The sheath 670 may be advanced distally through the lumen 204 of the prosthesis 200 and out through the first fenestration 210 as shown in FIG. 19. A dilator (not shown) may be positioned within the sheath 670 to aid in advancing the sheath over the guide wire 150. At this stage, the distal end of the sheath 670 may be positioned adjacent to the left renal artery 666. A wire guide 672 may be introduced via the sheath 670. The wire guide 672 may be advanced within the sheath 670, within the prosthesis 200, and out the first fenestration 210 to exit the sheath 670 and enter the left renal artery 666 as shown in FIG. 20. The wire guide 672 may be received within a catheter 674, which may be introduced with the wire guide 672 via the sheath 670. The catheter 674 may aid in guiding the wire guide 672 into the left renal artery 666. To that end, the catheter 674 may be advanced such that the distal end of the catheter 674 is positioned near the ostium of the left renal artery 666 as shown in FIG. 20. The wire guide 672 and the catheter 674 may be further advanced into the left renal artery 666.

Figure 21:
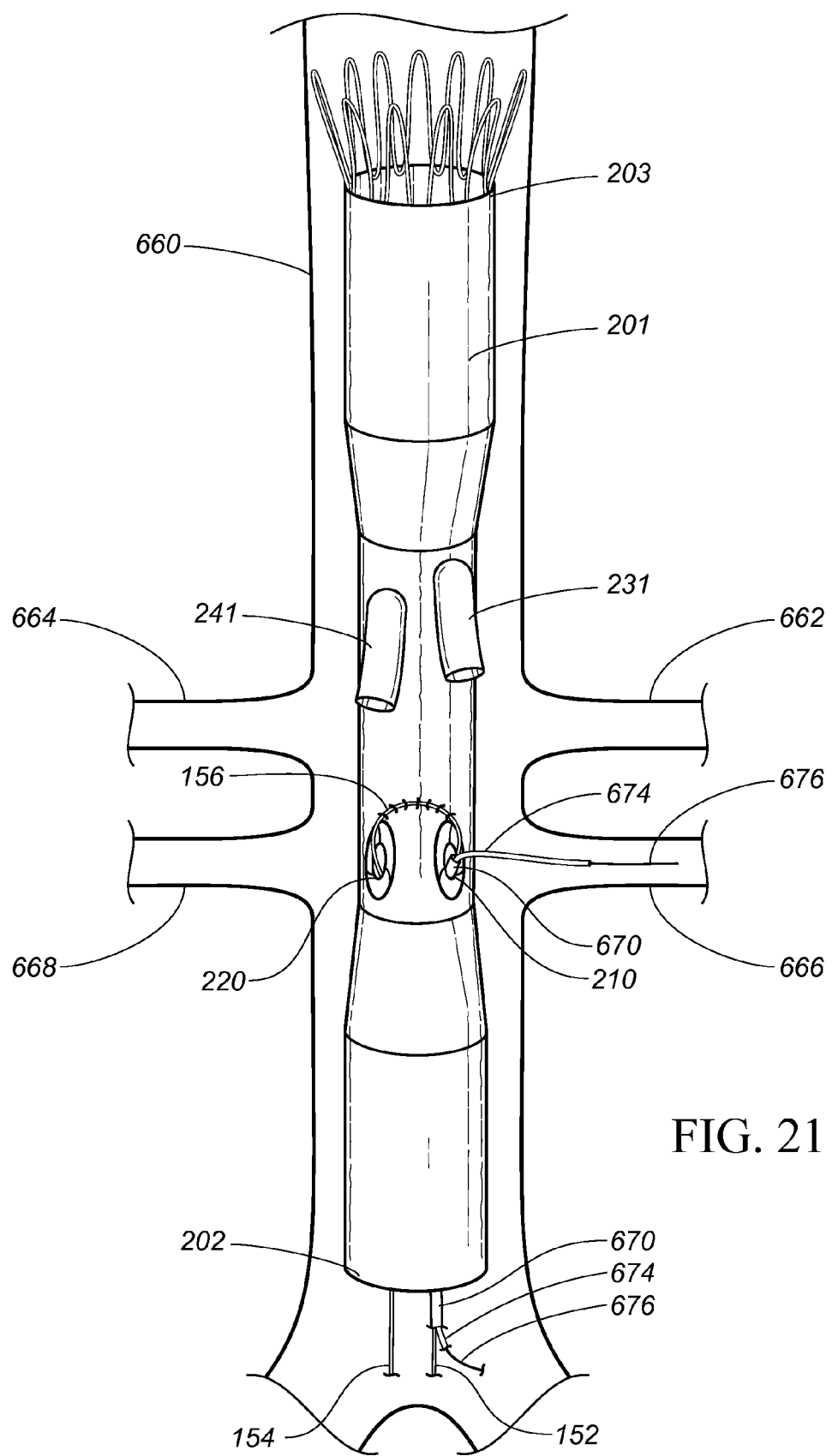

The wire guide 672 may be retracted proximally relative to the catheter 674 and the sheath 670 to remove the wire guide 672 from the patient's body. A wire guide 676 may be introduced through the catheter 674 and the sheath 670 in a distal direction and ultimately into the left renal artery 666 as shown in FIG. 21. In other words, the wire guide 672 may be replaced with the wire guide 676. The wire guide 676 may have a stiffness that is greater than a stiffness of the wire guide 672. The relatively stiff wire guide 676 may aid in deploying a branch prosthesis in the first fenestration 210 as further described below.

Figure 22:
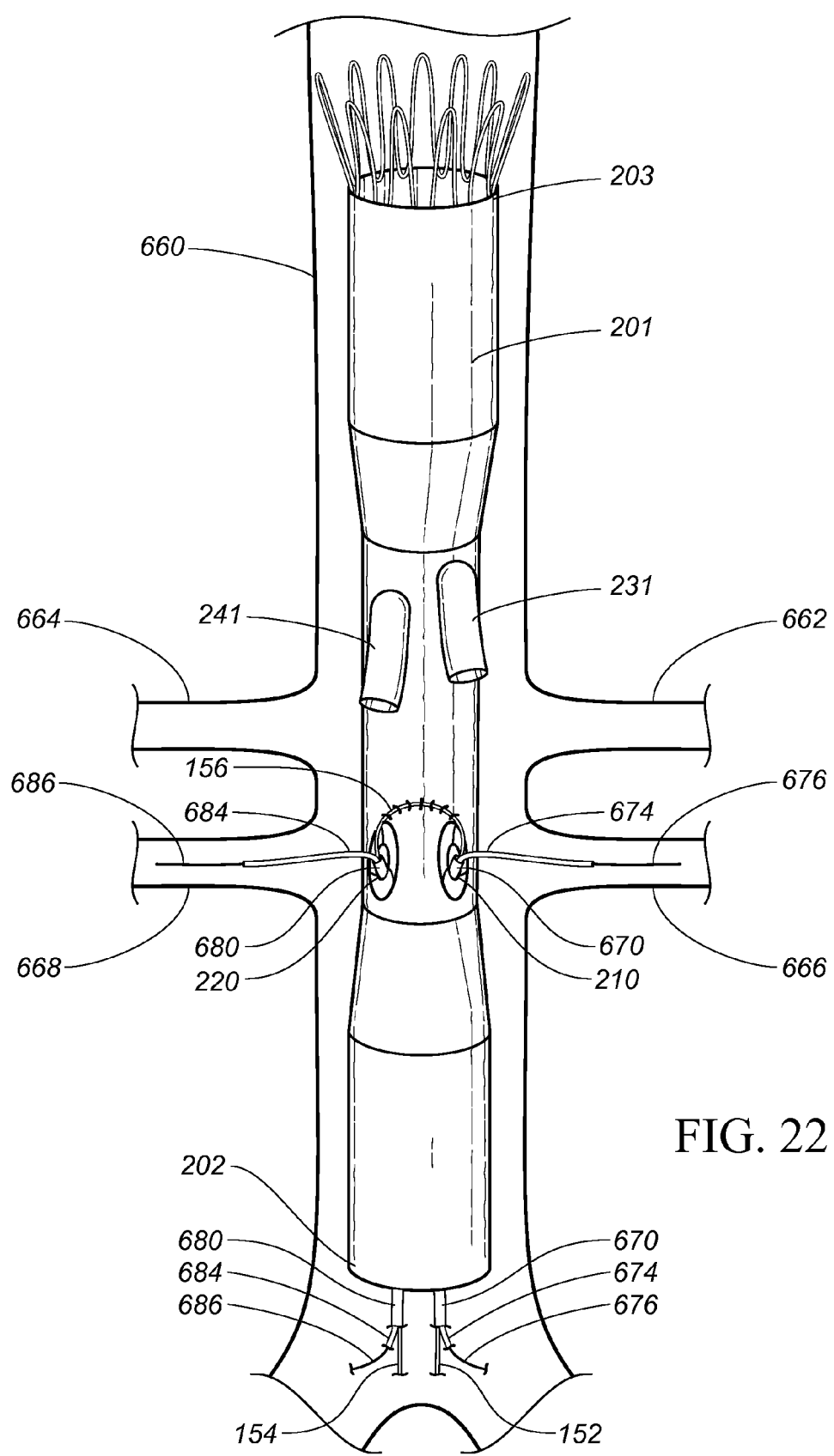
FIG. 22 illustrates one example of a sheath introduced over another segment of the guide wire and into another fenestration of the prosthesis shown in FIG. 18 and one example of a catheter and a wire guide introduced within the sheath and into another renal artery.

In a next stage, the sequence shown in FIGS. 19-21 may be repeated to cannulate the right renal artery 668 as shown in FIG. 22. A sheath may be guided over the second end segment 154 of the guide wire 150 and through the second fenestration 220. For example, a sheath 680 may be advanced over the second end segment 154 of the guide wire 150 in a distal direction, through the lumen 204 of the prosthesis 200, and out through the second fenestration 220. A dilator may be positioned within the sheath 680 to aid in advancing the sheath over the guide wire 150. At this stage, the distal end of the sheath 680 may be positioned adjacent to the right renal artery 668. A first wire guide (not shown) may be introduced via the sheath 680 and advanced within the sheath 680, within the prosthesis 200, and out the second fenestration 220 to exit the sheath 680 and enter the right renal artery 668. The first wire guide may be received within a catheter 684, which may be introduced with the first wire guide via the sheath 680. The first wire guide and the catheter 684 may be further advanced into the right renal artery 668. The first wire guide may be replaced with a wire guide 686, which may have a stiffness that is greater than a stiffness of the first wire guide. The relatively stiff wire guide 686 may aid in deploying a branch prosthesis in the second fenestration 220 as further described below.

The position of the first end segment 152 of the guide wire 150 in the first fenestration 210 may aid in cannulation of the left renal artery 666. Similarly, the position of the second end segment 154 of the guide wire 150 in the second fenestration 220 may aid in cannulation of the right renal artery 668. For example, the first and second end segments 152, 154 of the guide wire 150 may extend to the proximal end of the introducer, and the intermediate segment 156 may be attached to the tubular body 201 of the prosthesis to provide stability to the guide wire and/or the prosthesis during introduction or movement of various components (e.g., sheaths, wire guides, or catheters) as described herein. In other words, the guide wire 150 may provide a relatively stable platform for the introduction of various components within the fenestrations of the prosthesis 200. With the catheter 674 and the wire guide 676 in place within the left renal artery 666 and the catheter 684 and the wire guide 686 in place within the right renal artery 668, the guide wire 150 may be removed from the patient's body. One of the first end segment 152 and the second end segment 154 of the guide wire 150 may be retracted proximally relative to the prosthesis 200 to slide the guide wire out of engagement with the sutures 158 (or other mechanism which may secure the guide wire to the tubular body 201). The respective end segment may be retracted a sufficient distance to remove the guide wire 150 from the patient's body.

Figure 23:
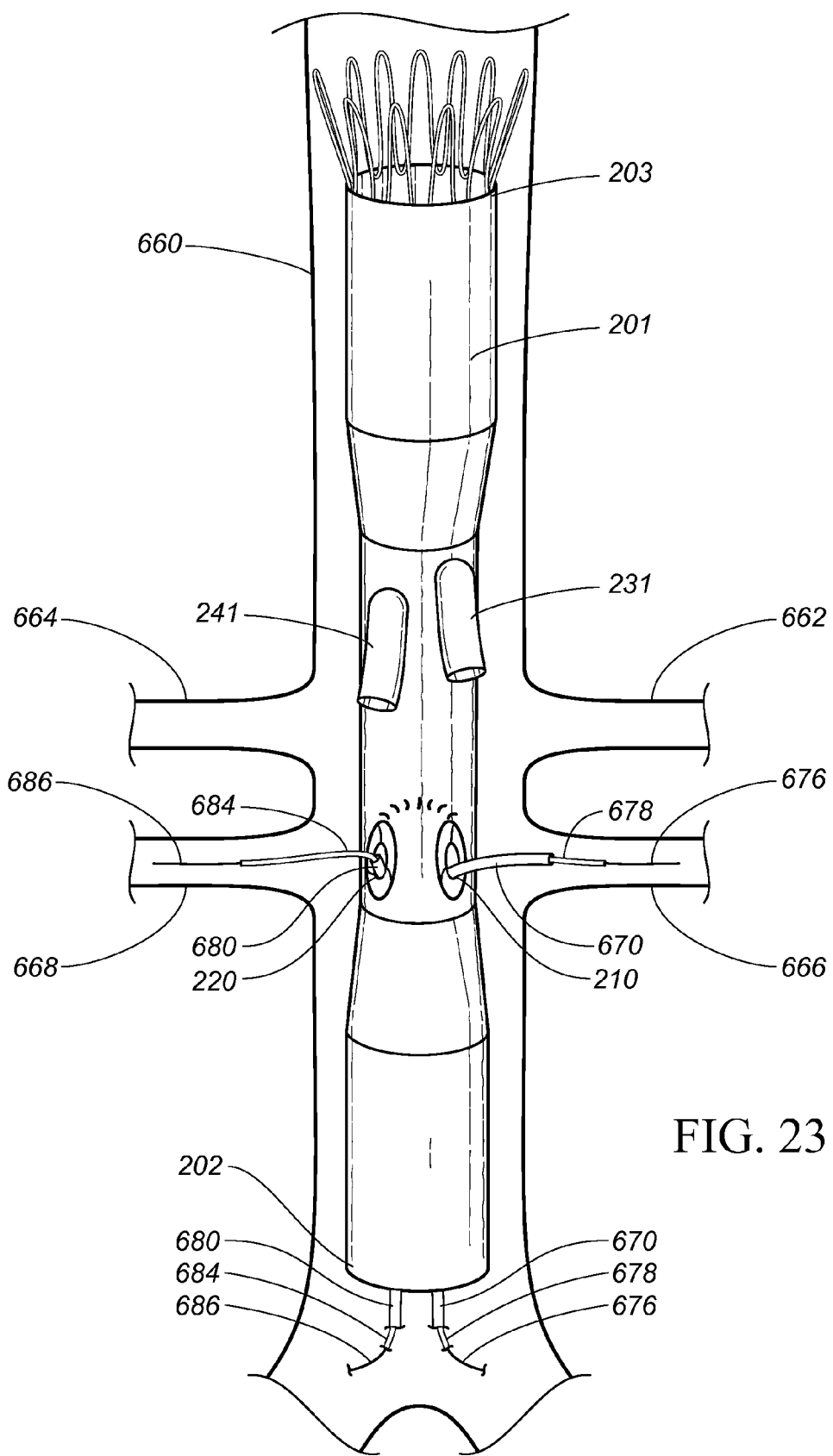
FIG. 23 illustrates one example of introducers advanced within the sheaths shown in FIGS. 19-22.

In a next stage, the sheath 670 may be advanced distally over the catheter 674 and the wire guide 676 and into the left renal artery 666 as shown in FIG. 23. With the sheath 670 in place within the left renal artery 666, the catheter 674 may be retracted proximally relative to the sheath 670 and removed from the patient's body. The wire guide 676 may remain in place within the left renal artery 666. The position of the sheath 670 and the wire guide 676 in the left renal artery 666 may enable delivery of a branch prosthesis into the left renal artery using any suitable endovascular technique.

Figure 24:
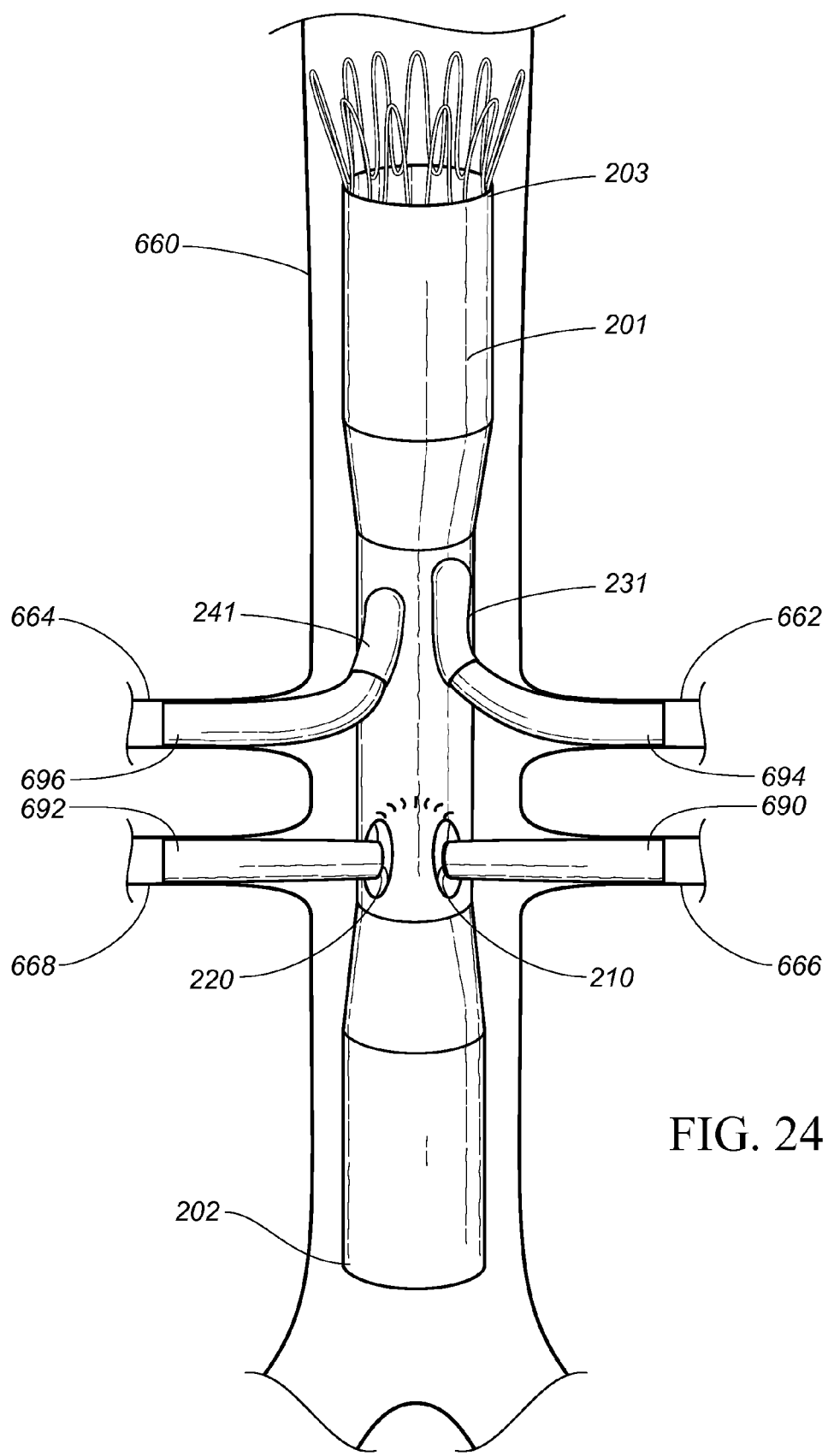
FIG. 24 illustrates the prosthesis shown in FIG. 18 with exemplary branch extension prostheses deployed in the fenestrations and branches of the prosthesis.

In a next stage, a branch prosthesis 690 may be deployed in the left renal artery 666. The branch prosthesis 690 (and the branch prostheses 692, 694, 696 described below) may be formed of biocompatible materials and may be configured as covered stents. Alternatively, the branch prostheses may be configured as bare stents. The covered or bare stents may be either self-expanding or balloon expandable. In one embodiment, a branch prosthesis may have both self-expanding and balloon expandable components. The branch prosthesis 690 may be compressed into a delivery state and delivered using a suitable deployment system or introducer (e.g., the interventional catheters 98A, 98B described above with reference to FIG. 12). For example, an introducer 678 may include a delivery catheter and an outer sheath. In another example, the outer sheath may be omitted from the introducer. The branch prosthesis 690 may be radially compressed onto the delivery catheter of the introducer and covered by the outer sheath. The introducer 678 may be introduced over the wire guide 676 and through the sheath 670 in a distal direction from the femoral artery and ultimately into the left renal artery 666 as shown in FIG. 23. With the introducer 678 in place within the left renal artery 666, the sheath 670 may be retracted proximally relative to the introducer 678 and removed from the left renal artery. The branch prosthesis 690 may be deployed from the introducer 678. Upon deployment, the branch prosthesis 690 may extend from the first fenestration 210 into the left renal artery 666 as shown in FIG. 24. Upon deployment, the branch prosthesis 690 and the first fenestration 210 may be mated. Optionally, the devices may be expanded for about 30 seconds using a suitably sized balloon dilation catheter. At this time, the branch prosthesis 690 may provide patent fluid flow through the prosthesis 200 into the left renal artery 666. The introducer 678, the wire guide 676, and the sheath 670 then may be withdrawn proximally out of the patient's body via the femoral artery.

The branch prosthesis 692 may be deployed in the right renal artery 668 in a similar manner. For example, the branch prosthesis 692 may be radially compressed onto a delivery catheter of an introducer, which may be configured as described above with reference to the introducer 678. The introducer may be introduced over the wire guide 686 and through the sheath 680 in a distal direction from the femoral artery and ultimately into the right renal artery 668. With the introducer in place within the right renal artery 668, the sheath 680 may be retracted proximally relative to the introducer and removed from the right renal artery. The branch prosthesis 692 may be deployed from the introducer. Upon deployment, the branch prosthesis 692 may extend from the second fenestration 220 into the right renal artery 668 as shown in FIG. 24. Upon deployment, the branch prosthesis 692 and the second fenestration 220 may be mated. Optionally, the devices may be expanded for about 30 seconds using a suitably sized balloon dilation catheter. At this time, the branch prosthesis 692 may provide patent fluid flow through the prosthesis 200 into the right renal artery 668. The introducer, the wire guide 686, and the sheath 680 then may be withdrawn proximally out of the patient's body via the femoral artery.

The branch prosthesis 694 may be deployed in the celiac artery 662, and the branch prosthesis 696 may be deployed in the superior mesenteric artery 664 using any suitable endovascular technique. Upon deployment, the branch prosthesis 694 may extend from the first branch 231 into the celiac artery 662, and the branch prosthesis 696 may extend from the second branch 241 into the superior mesenteric artery 664 as shown in FIG. 24.

The branch prostheses described herein may be deployed in any order. For example, the branch prosthesis 690 may be deployed in the left renal artery 666 prior to deployment of the branch prosthesis 692 in the right renal artery 668, or vice versa. The branch prostheses 694, 696 may be deployed in the celiac artery 662 and the superior mesenteric artery 664, respectively, before, after, or at approximately the same time as deployment of the branch prostheses 690, 692 in the left renal artery 666 and the right renal artery 668, respectively.

It will be appreciated that the exact number, orientation, and placement of the various branches and/or fenestrations along the tubular body of the prosthesis may be varied without departing from the spirit of this disclosure. Moreover, while one exemplary procedure has been described with reference to the abdominal aorta and its branches, a prosthesis having multiple branches and/or fenestrations as described herein may be used in other procedures, and particularly those that may benefit from a preloaded arrangement to facilitate insertion of delivery components into the various openings of the prosthesis.

FIG. 25 illustrates another example of the guide wire 150 received within the prosthesis 200 in a preloaded configuration. In this example, the prosthesis 200 may be substantially free of guide wire openings as described above with reference to FIG. 17. The first end segment 152 of the guide wire 150 may extend distally from the proximal end of the delivery device. The first end segment 152 may enter the lumen 204 through the proximal end 202 of the prosthesis 200. The first end segment 152 may extend distally within the lumen 204 and exit the tubular body 201 of the prosthesis 200 through the first fenestration 210.

The intermediate segment 156 of the guide wire 150 may extend between the first fenestration 210 and the second fenestration 220 of the prosthesis 200. The intermediate segment 156 may extend distally external of the tubular body 201 toward the first branch 231. The intermediate segment 156 may enter the lumen 234 of the first branch 231 at the second end 233, extend distally within the first branch, and enter the lumen 204 through the third fenestration 230. The intermediate segment may enter the lumen 244 of the second branch 241 through the fourth fenestration 240, extend proximally within the second branch, and exit the second branch at the second end 243. The intermediate segment 156 may extend proximally external of the tubular body 201 toward the second fenestration 220.

The second end segment 154 of the guide wire 150 may enter the tubular body 201 of the prosthesis 200 through the second fenestration 220. The second end segment 154 may extend proximally within the lumen 204 and exit the lumen 204 through the proximal end 202 of the prosthesis 200. The second end segment 154 of the guide wire 150 may extend proximally to the proximal end of the delivery device. The first end segment 152 of the guide wire 150 may enable introduction of a branch prosthesis into each of the first fenestration 210 and the second branch 241 to couple the prosthesis 200 to the left renal artery and the superior mesenteric artery, and the second end segment 154 of the guide wire 150 may enable introduction of a branch prosthesis into each of the second fenestration 220 and the first branch 231 to couple the prosthesis to the right renal artery and the celiac artery as further described below.

The intermediate segment 156 of the guide wire 150 may be substantially U-shaped with the opening of the U-shaped intermediate segment facing proximally as shown in FIG. 25. One leg of the U-shaped intermediate segment 156 may extend distally away from the first fenestration 210 and through the first branch 231 and the third fenestration 230. The other leg may extend proximally through the fourth fenestration 240 and the second branch 241 and toward the second fenestration 220. The curved portion of the U-shaped intermediate segment 156 may be positioned within the lumen 204 as shown in FIG. 25. Additionally, or alternatively, the curved portion of the U-shaped intermediate segment 156 may be positioned longitudinally distal of the third and fourth fenestrations 230, 240 and proximal of the distal end 203 of the prosthesis 200. Additionally, or alternatively, the guide wire 150 may be positioned such that no portion of the guide wire extends distally beyond the distal end 203 of the prosthesis 200.

FIGS. 26-31 illustrate an exemplary method of using the prosthesis 200 of FIG. 25 to treat a condition (e.g., an aneurysm) in the area of an abdominal aorta and/or branch vessels of a patient. In a first step, the prosthesis 200 may be provided with the guide wire 150 coupled to the prosthesis in the preloaded configuration as shown in FIG. 25. The prosthesis 200 may be compressed into a delivery state and delivered into the abdominal aorta 660 of a patient using any suitable deployment system or introducer (e.g., the delivery catheter 1 described above with reference to FIGS. 1-12) as described above with reference to FIG. 18.

Figure 26:
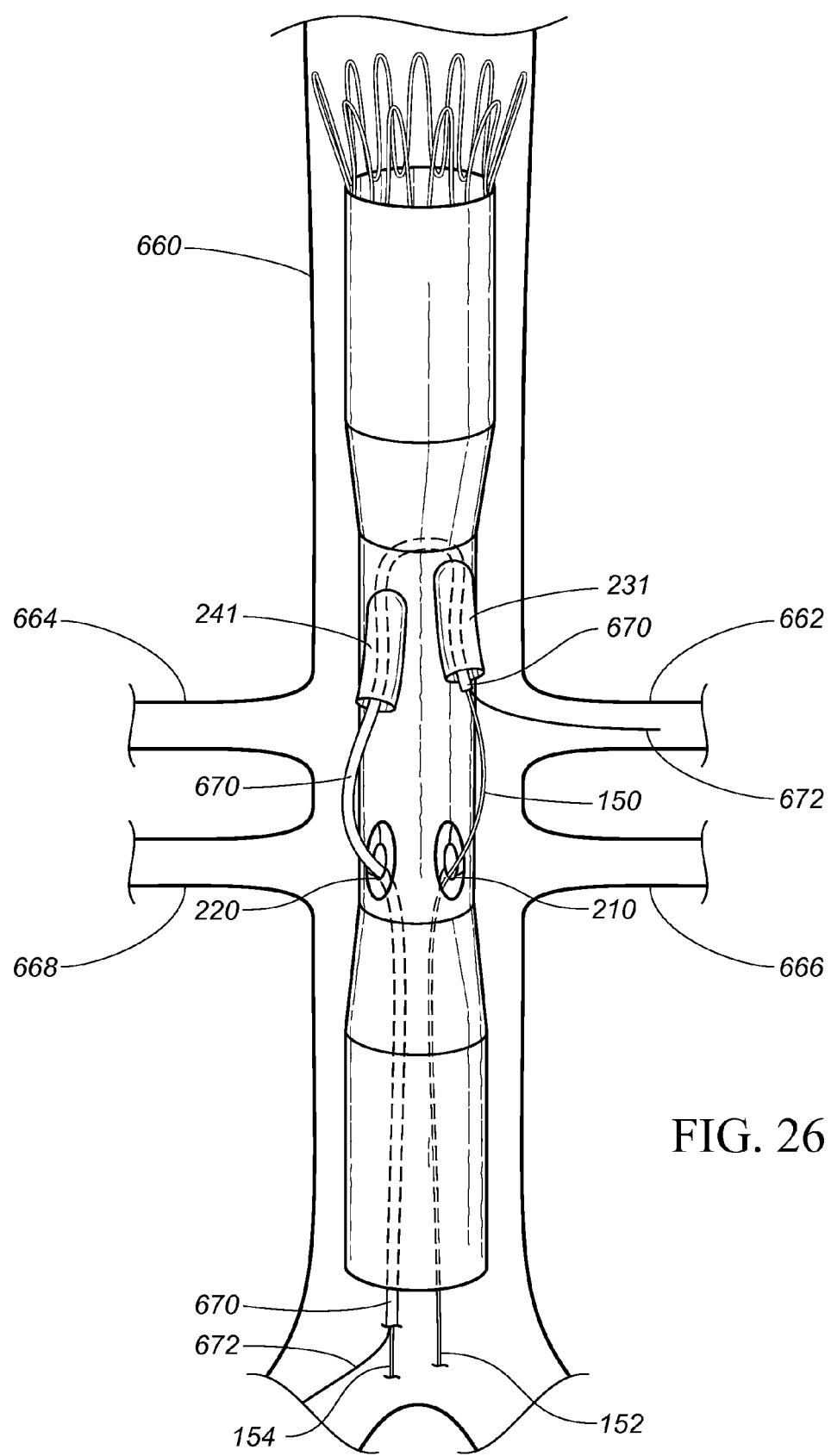
FIG. 26 illustrates one example of a sheath introduced over a segment of the guide wire, and through each of a fenestration and two branches of the prosthesis shown in FIG. 25.

With the prosthesis 200 positioned within the abdominal aorta 660, each of the left renal artery 666, the right renal artery 668, the celiac artery 662, and the superior mesenteric artery 664 may be cannulated. To that end, the sheath 670 may be advanced over the second end segment 154 of the guide wire 150 in a distal direction as shown in FIG. 26. The sheath 670 may be advanced distally through the lumen 204 of the prosthesis 200 and out through the second fenestration 220. The sheath 670 may be further advanced distally through the lumen 244 of the second branch 241 and the fourth fenestration 240 into the lumen 204 of the prosthesis 200. The sheath 670 may be further advanced over the curved portion of the intermediate segment 156 of the guide wire 150 and proximally through the third fenestration 230 and the lumen 234 of the first branch 231. The sheath 670 may exit the first branch 231 through the second end 233 as shown in FIG. 26. At this stage, the distal end of the sheath 670 may be positioned adjacent to the celiac artery 662.

The wire guide 672 may be introduced via the sheath 670. The wire guide 672 may be advanced within the sheath 670 until the distal end of the wire guide 672 exits the sheath 670 and enters the celiac artery 662 as shown in FIG. 26. In this manner, the preloaded wire guide 150 may be used to cannulate the celiac artery 662 with the wire guide 672. The wire guide 672 may be received within a catheter as described above with reference to FIG. 20. The wire guide 672 may be replaced with the relatively stiffer wire guide 676A as described above with reference to FIGS. 20-21 to aid in deploying a branch prosthesis in the first branch 231 as further described below.

Figure 27:
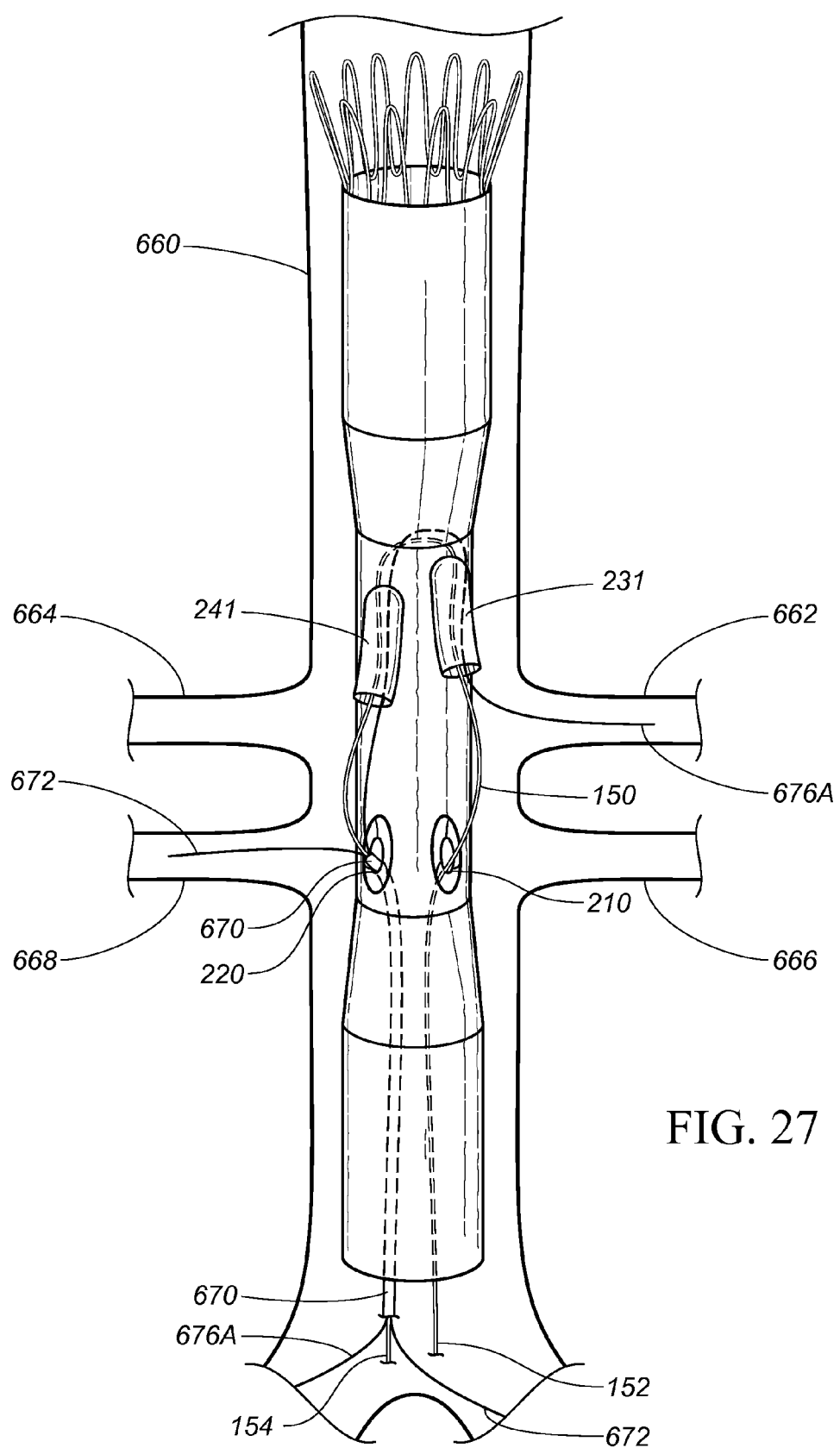
FIG. 27 illustrates the sheath shown in FIG. 26 retracted out of the two branches of the prosthesis shown in FIG. 25.

The sheath 670 may be retracted over the guide wire 150. For example, the proximal end of the sheath 670 may be retracted proximally over the second end segment 154 of the guide wire 150 to retract the distal end of the sheath distally through the first branch 231 and the third fenestration 230, over the curved portion of the intermediate segment of the guide wire 150, and proximally through the fourth fenestration 240 and the second branch 241. The sheath 670 may be retracted a sufficient distance such that the distal end of the sheath 670 is positioned adjacent to the right renal artery 668 as shown in FIG. 27.

Figure 28:
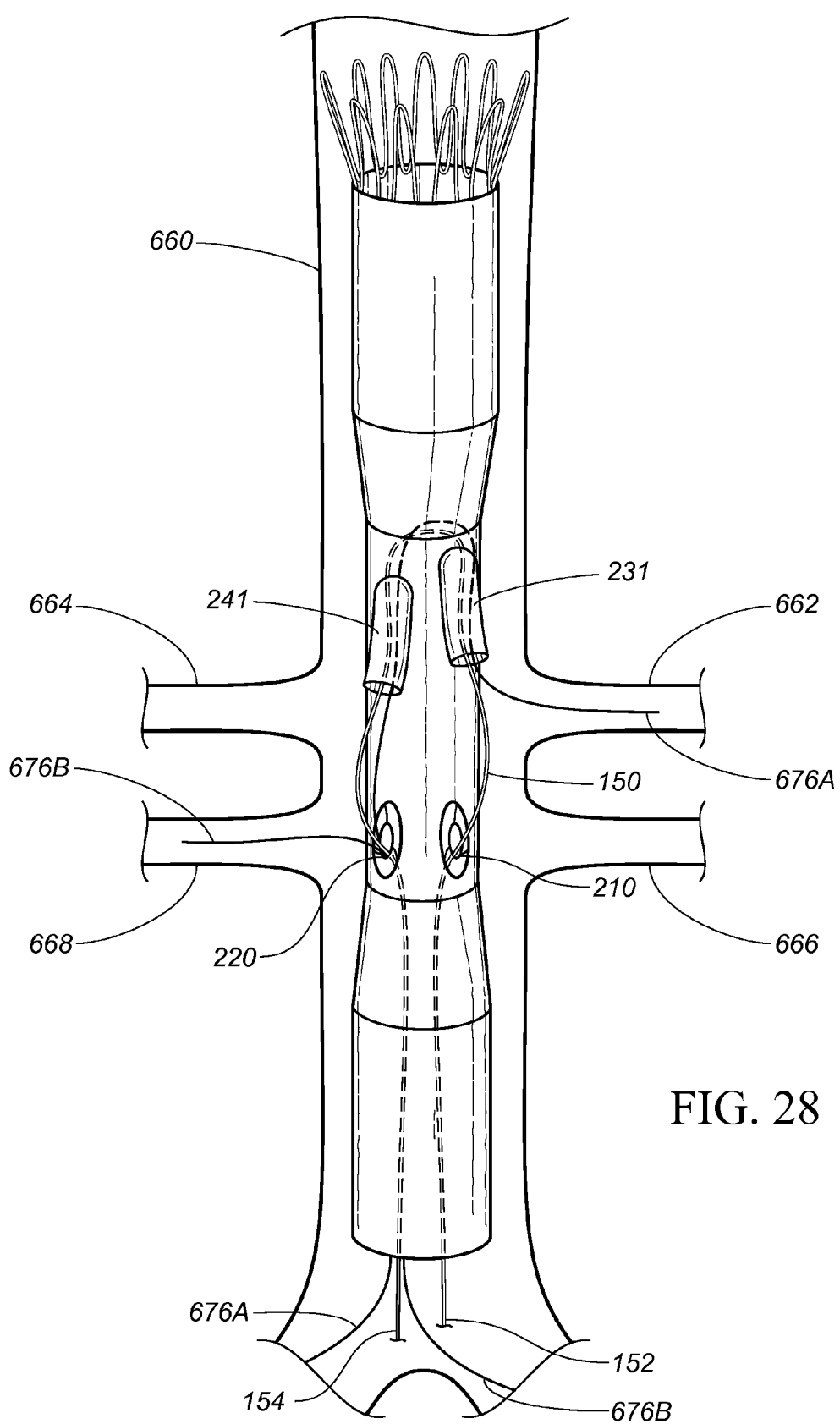
FIG. 28 illustrates the prosthesis of FIG. 25 with one fenestration and one branch cannulated with exemplary wire guides.

In a next stage, the sequence described above with reference to FIG. 26 may be repeated to cannulate the right renal artery 668. For example, the wire guide 672, or another wire guide, may be introduced via the sheath 670 and advanced within the sheath 670, within the prosthesis 200, and out the second fenestration 220 to exit the sheath 670 and enter the right renal artery 668 as shown in FIG. 27. The wire guide 672 may be received within a catheter as described above with reference to FIG. 20. The wire guide 672 may be replaced with a relatively stiffer wire guide 676B to aid in deploying a branch prosthesis in the second fenestration 220 as further described below. With each of the celiac artery 662 and the right renal artery 668 cannulated as shown in FIG. 28, the sheath 670 may be retracted proximally over the second end segment 154 of the guide wire 150 and removed from the patient's body.

Figure 29:
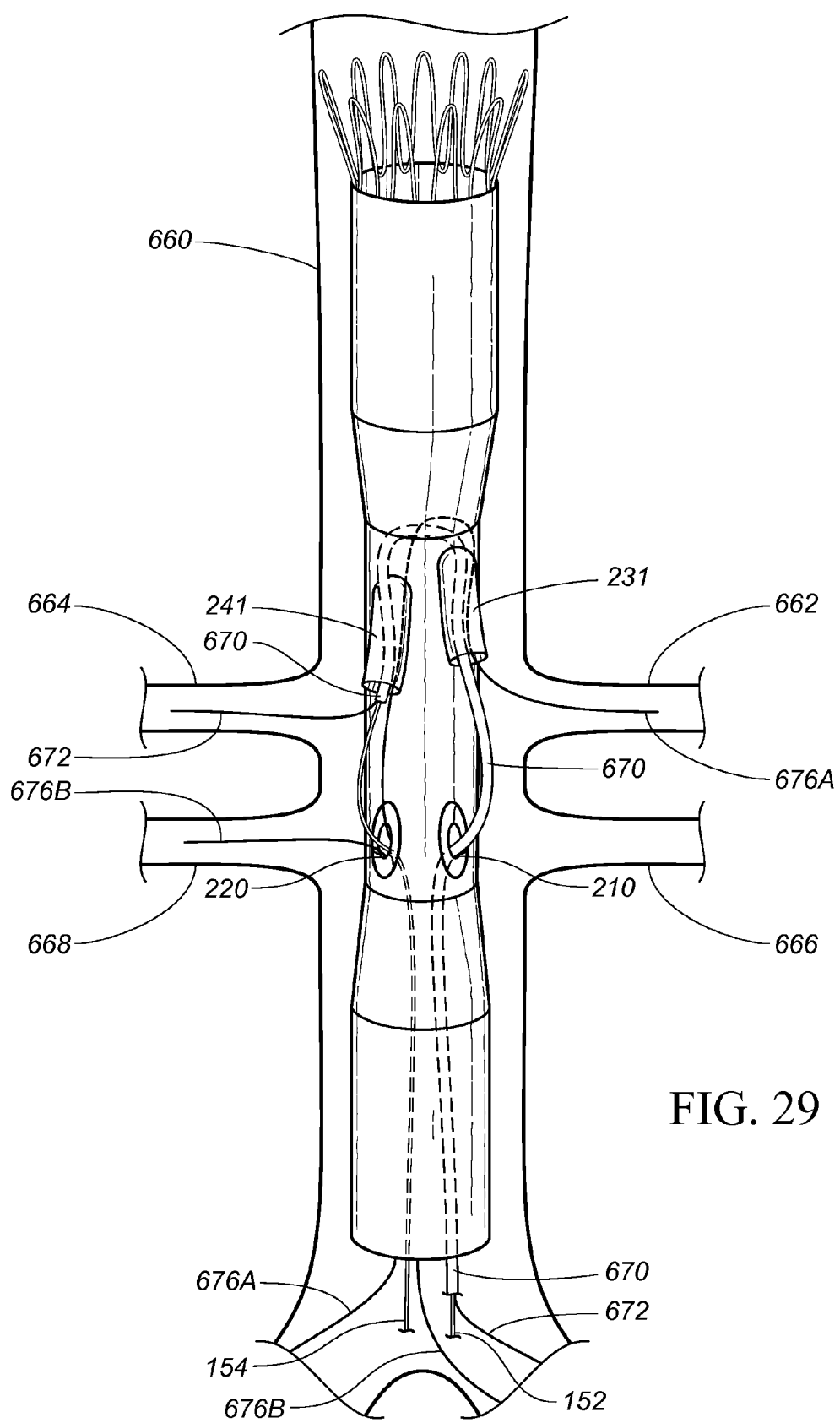
FIG. 29 illustrates on example of a sheath introduced over another segment of the guide wire, and through each of a fenestration and two branches of the prosthesis shown in FIG. 25.

In a next stage, the sheath 670, or another sheath, may be advanced over the first end segment 152 of the guide wire 150 in a distal direction as shown in FIG. 29. The sheath 670 may be advanced distally through the lumen 204 of the prosthesis 200 and out through the first fenestration 210. The sheath 670 may be further advanced distally through the lumen 234 of the first branch 231 and the third fenestration 230 into the lumen 204 of the prosthesis 200. The sheath 670 may be further advanced over the curved portion of the intermediate segment 156 of the guide wire 150 and proximally through the fourth fenestration 240 and the lumen 244 of the second branch 241. The sheath 670 may exit the second branch 241 through the second end 243 as shown in FIG. 29. At this stage, the distal end of the sheath 670 may be positioned adjacent to the superior mesenteric artery 664.

The wire guide 672, or another wire guide, may be introduced via the sheath 670. The wire guide 672 may be advanced within the sheath 670 until the distal end of the wire guide 672 exits the sheath 670 and enters the superior mesenteric artery 664 as shown in FIG. 29. In this manner, the preloaded guide wire 150 may be used to cannulate the superior mesenteric artery 664 with the wire guide 672. The wire guide 672 may be received within a catheter as described above with reference to FIG. 20. The wire guide 672 may be replaced with the relatively stiffer wire guide 676C as described above with reference to FIGS. 20-21 to aid in deploying a branch prosthesis in the second branch 241 as further described below.

The sheath 670 may be retracted over the guide wire 150. For example, the proximal end of the sheath 670 may be retracted proximally over the first end segment 152 of the guide wire 150 to retract the distal end of the sheath distally through the second branch 241 and the fourth fenestration 240, over the curved portion of the intermediate segment of the guide wire 150, and proximally through the third fenestration 230 and the first branch 231. The sheath 670 may be retracted a sufficient distance such that the distal end of the sheath 670 is positioned adjacent to the left renal artery 666 as shown in FIG. 30.

Figure 30:
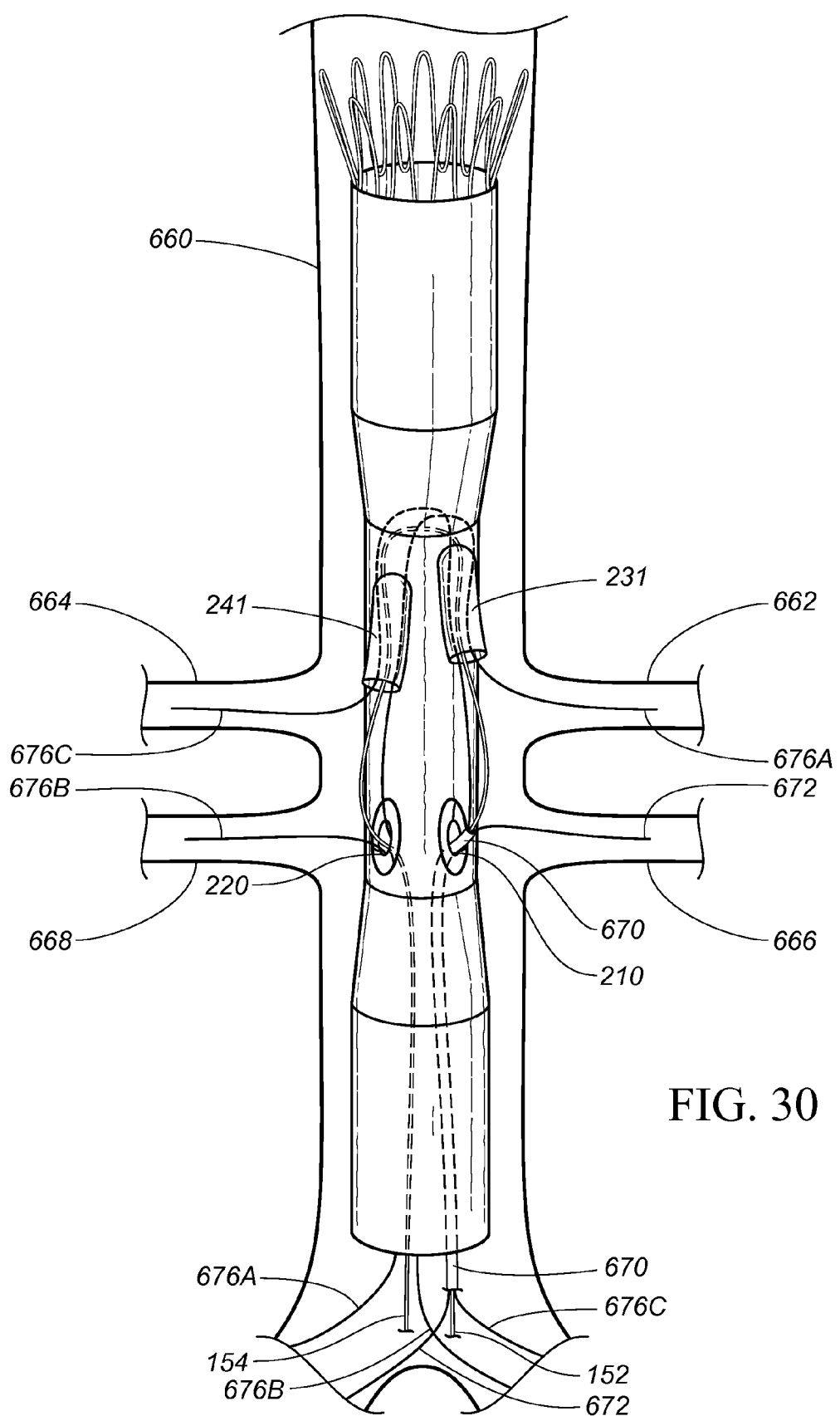
FIG. 30 illustrates the sheath shown in FIG. 29 retracted out of the two branches of the prosthesis shown in FIG. 25.
Figure 31:
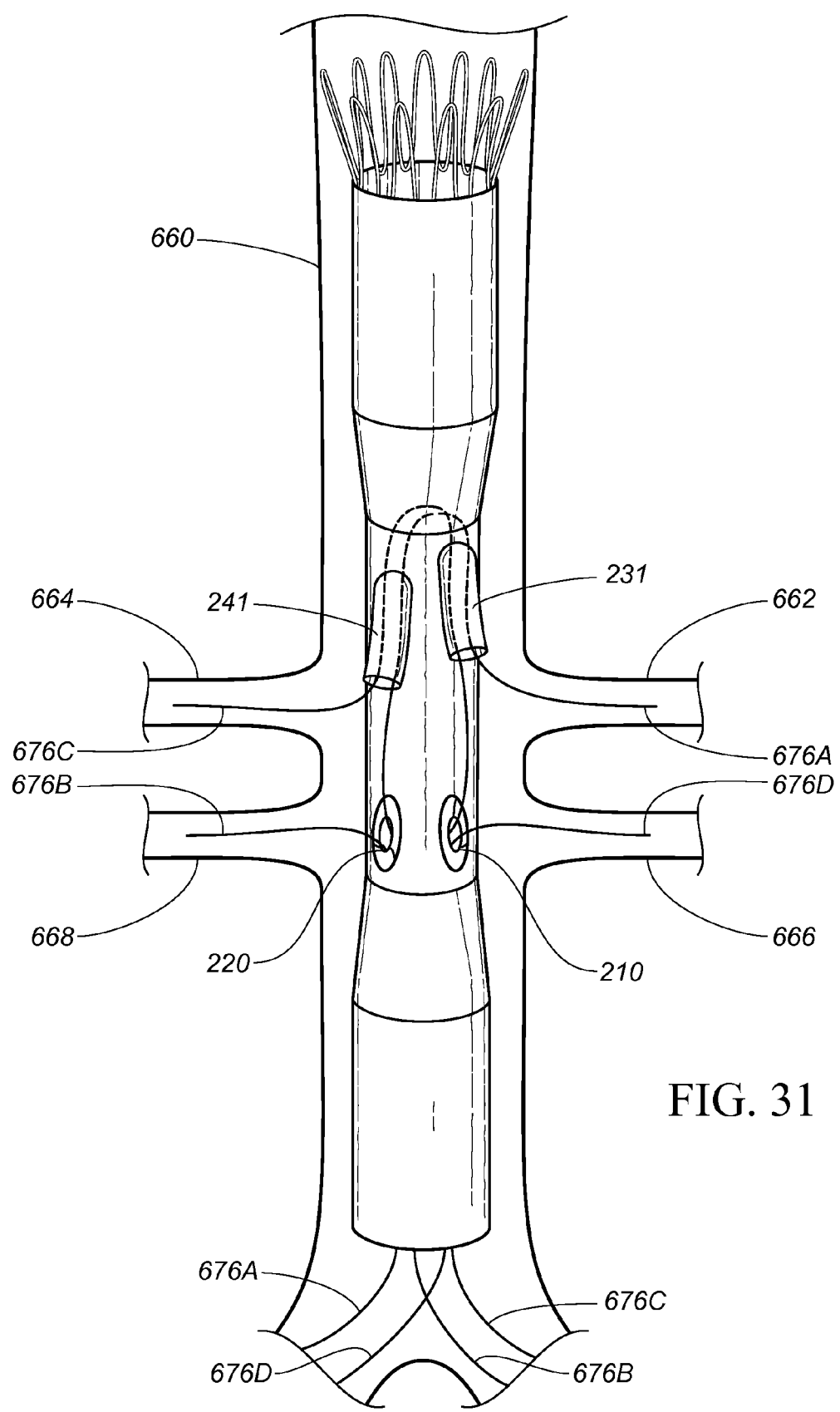
FIG. 31 illustrates the prosthesis of FIG. 25 with two fenestrations and two branches cannulated with exemplary wire guides.

In a next stage, the sequence described above with reference to FIG. 26 may be repeated to cannulate the left renal artery 666 as shown in FIG. 30. For example, the wire guide 672, or another wire guide, may be introduced via the sheath 670 and advanced within the sheath 670, within the prosthesis 200, and out the first fenestration 210 to exit the sheath 670 and enter the left renal artery 666. The wire guide 672 may be received within a catheter as described above with reference to FIG. 20. The wire guide 672 may be replaced with a relatively stiffer wire guide 676D to aid in deploying a branch prosthesis in the first fenestration 210 as further described below. With each of the superior mesenteric artery 664 and the left renal artery 666 cannulated, the sheath 670 may be retracted proximally over the first end segment 152 of the guide wire 150 and removed from the patient's body. At this stage, the prosthesis 200 may be deployed within the aorta 660 with each of the celiac artery 662, the superior mesenteric artery 664, the left renal artery 666, and the right renal artery 668 cannulated with a respective wire guide as shown in FIG. 31.

Following cannulation of the branch vessels, the guide wire 150 may be removed from the patient's body. For example, one of the first end segment 152 and the second end segment 154 of the guide wire 150 may be retracted proximally relative to the prosthesis 200 to slide the guide wire out of engagement with the first and second branches 231, 241 and the first and second fenestrations 210, 220. The respective end segment may be retracted a sufficient distance to remove the guide wire 150 from the patient's body.

A branch prosthesis may be deployed within each of the celiac artery 662, the superior mesenteric artery 664, the left renal artery 666, and the right renal artery 668 using any suitable endovascular technique as described above with reference to FIGS. 23-24. For example, a delivery device may be introduced over the wire guide 676A and used to deploy the branch prosthesis 694 into the celiac artery 662, a delivery device may be introduced over the wire guide 676B and used to deploy the branch prosthesis 692 into the right renal artery 668, a delivery device may be introduced over the wire guide 676C and used to deploy the branch prosthesis 696 into the superior mesenteric artery 664, and a delivery device may be introduced over the wire guide 676D and used to deploy the branch prosthesis 690 into the left renal artery 666. In this manner, the first branch 231 may be mated to the celiac artery 662 with the branch prosthesis 694, the second fenestration 220 may be mated to the right renal artery 668 with the branch prosthesis 692, the second branch 241 may be mated to the superior mesenteric artery 664 with the branch prosthesis 696, and the first fenestration 210 may be mated to the left renal artery 666 with the branch prosthesis 690 as shown in FIG. 24. The branch prostheses may be deployed within the respective branch vessels in any order.

The configuration of the preloaded guide wire 150 may enable cannulation of each of the celiac artery 662, the superior mesenteric artery 664, the left renal artery 666, and the right renal artery 668 from a single access point (e.g., from a single incision into a single femoral artery). This may enable the prosthesis 200 to be deployed in a shorter amount of time than may be required using multiple access points (e.g., two femoral arteries, a femoral artery and a brachial artery, or any other multiple access points). Additionally, or alternatively, the configuration of the preloaded guide wire 150 may enable cannulation of multiple vessels simultaneously. For example, once the celiac artery 662 has been cannulated and the sheath 670 has been retracted to align with the right renal artery 668 as shown in FIG. 27, the right renal artery may be cannulated while another sheath is advanced over the first end 152 of the guide wire 150 to cannulate the superior mesenteric artery 696. In this manner, once one of the first and second branches 231, 241 of the prosthesis 200 has been cannulated, the other branch may be cannulated (e.g., by a second operator) while one of the first and second fenestrations 210, 220 is being cannulated. This may reduce the amount of time required to deploy the prosthesis 200.

While various embodiments of the invention have been described, the invention is not to be restricted except in light of the attached claims and their equivalents. Moreover, the advantages described herein are not necessarily the only advantages of the invention and it is not necessarily expected that every embodiment of the invention will achieve all of the advantages described.

We claim:

1. A system comprising:
    an endoluminal prosthesis comprising a tubular body comprising a graft material wall, a proximal end opening, a distal end opening, and a lumen extending longitudinally therein; a first fenestration in the graft material wall and a second fenestration in the graft material wall, the first fenestration and the second fenestration spaced from one another circumferentially about the tubular body; and
    a guide wire having a first end and a second end both extending from a region proximal of the proximal end opening, the guide wire entering the proximal end opening, exiting the first fenestration, partially laterally traversing an exterior surface of the prosthesis, entering the second fenestration, and exiting the proximal end opening, no portion of the guide wire extending distally beyond the distal end opening, wherein the guide wire traverses the exterior surface of the prosthesis immediately above the first and second fenestrations.

2. The system of claim 1, wherein the guide wire is attached to the exterior surface of the prosthesis.

3. The system of claim 2, wherein the guide wire is attached to the exterior surface of the prosthesis with at least one suture.

4. The system of claim 1, wherein the guide wire partially circumferentially traverses the exterior surface of the prosthesis.

5. The system of claim 4, wherein a portion of the guide wire partially circumferentially traversing the exterior surface of the prosthesis is positioned on an anterior side of the prosthesis.

6. The system of claim 1, wherein the prosthesis comprises a third fenestration in the graft material wall and a fourth fenestration in the graft material wall, and the third fenestration and the fourth fenestration are spaced from one another circumferentially about the tubular body and positioned distal of each of the first fenestration and the second fenestration.

7. The system of claim 6, wherein a portion of the guide wire partially traversing the exterior surface of the prosthesis is disposed longitudinally distal of the first fenestration and the second fenestration.

8. The system of claim 6, wherein the guide wire enters or exits the prosthesis only at the proximal end opening, the first fenestration, and the second fenestration.

9. The system of claim 8, wherein a portion of the guide wire partially circumferentially traverses the exterior surface of the prosthesis and is attached to the exterior surface of the prosthesis.

10. The system of claim 1, wherein the guide wire extends longitudinally within the lumen of the tubular body between the proximal end opening and the first fenestration and extends longitudinally within the lumen of the tubular body between the second fenestration and the proximal end opening.

11. A system comprising:
    an endoluminal prosthesis comprising a tubular body comprising a graft material wall, a proximal end opening, a distal end opening, and a lumen extending longitudinally therein; a first fenestration in the graft material wall and a second fenestration in the graft material wall and spaced circumferentially from the first fenestration; and
    a guide wire having a first end and a second end both extending proximal of the proximal end opening, the guide wire entering the proximal end opening, exiting the first fenestration, partially laterally traversing an exterior surface of the prosthesis, entering the second fenestration, and exiting the proximal end opening, a segment of the guide wire extending between the first fenestration and the second fenestration and positioned longitudinally between the proximal end opening and the distal end opening of the prosthesis,
    wherein the guide wire traverses the exterior surface of the prosthesis immediately above the first and second fenestrations.

12. The system of claim 11, wherein the segment of the guide wire extending between the first fenestration and the second fenestration partially circumferentially traverses the exterior surface of the prosthesis and is releasably attached to the exterior surface.

13. The system of claim 12, wherein the segment of the guide wire extending between the first fenestration and the second fenestration is disposed on an anterior side of the prosthesis.

14. A method of deploying a branch prosthesis in a main prosthesis, the method comprising:
    providing the main prosthesis and a guide wire, the main prosthesis comprising a tubular body comprising a graft material wall, a proximal end opening, a distal end opening, a first fenestration in the graft material wall, and a second fenestration in the graft material wall, the guide wire entering the proximal end opening, exiting the first fenestration, partially laterally traversing an exterior surface of the prosthesis, entering the second fenestration, and exiting the proximal end opening, no portion of the guide wire extending distally beyond the distal end opening;
    guiding an introducer over a first end of the guide wire and through the first fenestration of the prosthesis; and
    guiding an introducer over a second end of the guide wire and through the second fenestration of the prosthesis,
    wherein the guide wire traverses the exterior surface of the prosthesis immediately above the first and second fenestrations.

* * * * *